(12) United States Patent
Shevgoor et al.

(10) Patent No.: US 10,780,249 B2
(45) Date of Patent: Sep. 22, 2020

(54) NEEDLE CAPTURE SAFETY INTERLOCK FOR CATHETER

(71) Applicant: Becton, Dickinson and Company, Franklin Lakes, NJ (US)

(72) Inventors: Siddarth K. Shevgoor, Sandy, UT (US); John Stokes, Pleasant View, UT (US); Weston Harding, Lehi, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 481 days.

(21) Appl. No.: 15/304,375

(22) PCT Filed: Apr. 17, 2015

(86) PCT No.: PCT/US2015/026542
§ 371 (c)(1),
(2) Date: Oct. 14, 2016

(87) PCT Pub. No.: WO2015/161299
PCT Pub. Date: Oct. 22, 2015

(65) Prior Publication Data
US 2017/0035995 A1 Feb. 9, 2017

Related U.S. Application Data

(60) Provisional application No. 62/077,760, filed on Nov. 10, 2014, provisional application No. 61/981,223, (Continued)

(51) Int. Cl.
*A61M 25/06* (2006.01)
*A61M 25/00* (2006.01)
(Continued)

(52) U.S. Cl.
CPC ........ *A61M 25/0618* (2013.01); *A61M 5/158* (2013.01); *A61M 5/3202* (2013.01);
(Continued)

(58) Field of Classification Search
None
See application file for complete search history.

(56) References Cited

U.S. PATENT DOCUMENTS 3,585,996 A 6/1971 Reynolds et al.
4,332,249 A 6/1982 Joslin
(Continued)

FOREIGN PATENT DOCUMENTS

AU 2006203663 B2 2/2008
AU 2006203664 2/2008
(Continued)

OTHER PUBLICATIONS

MEDIKIT Co.,Ltd., Dual Protection Safety I.V. Catheter—Supercath 5: A New Generation of Safety I.V. Catheter, Medikit, Manufacturer TOGO MEDIKIT Co., Ltd., IVBB080001-B61G2S, Approximately 2008 '3 Pages Total).
(Continued)

*Primary Examiner* — Jason E Flick
*Assistant Examiner* — Tasnim Mehjabin Ahmed
(74) *Attorney, Agent, or Firm* — Dickinson Wright PLLC

(57) ABSTRACT

Catheter assembly (10) comprises catheter (22), needle (12) having sharp distal tip disposed in catheter (22), catheter hub (14) housing catheter (22) and needle (12), catheter hub (14) having collar (34) including notch (36), needle shield (20) connected to catheter hub (14) when needle (12) is in first position, and clip (40) disposed in needle shield (20) that cooperates with needle (12), wherein clip (40) engages catheter hub (14) in first position of needle (12), and clip (40) disengages catheter hub (14) via notch (36) when needle (12) is retracted to second position to enclose at least portion of needle (12). Clip (40) is mounted in outer housing (38) of needle shield (20) via spade (66) having outer wall
(Continued)

(70) exposed to outside of needle shield (20), in order to reduce overall width of needle shield (20).

23 Claims, 64 Drawing Sheets

Related U.S. Application Data filed on Apr. 18, 2014, provisional application No. 61/981,312, filed on Apr. 18, 2014.

(51) Int. Cl.

| | | |
|---|---|---|
| *A61M 39/24* | (2006.01) | |
| *A61M 5/32* | (2006.01) | |
| *A61M 5/158* | (2006.01) | |
| *A61M 5/34* | (2006.01) | |
| *A61M 39/06* | (2006.01) | |
| *A61M 39/22* | (2006.01) | |

(52) U.S. Cl.
CPC ........ *A61M 5/3213* (2013.01); *A61M 5/3232* (2013.01); *A61M 5/34* (2013.01); *A61M 25/0097* (2013.01); *A61M 25/0606* (2013.01); *A61M 25/0631* (2013.01); *A61M 39/24* (2013.01); *A61M 5/3273* (2013.01); *A61M 2039/064* (2013.01); *A61M 2039/066* (2013.01); *A61M 2039/0673* (2013.01); *A61M 2039/226* (2013.01)

(56) References Cited

U.S. PATENT DOCUMENTS

| | | |
|---|---|---|
| 4,387,879 A | 6/1983 | Tauschinski |
| 4,524,805 A | 6/1985 | Hoffman |
| 4,622,964 A | 11/1986 | Flynn |
| 4,762,516 A | 8/1988 | Luther et al. |
| 4,809,679 A | 3/1989 | Shimonaka et al. |
| 4,842,591 A | 6/1989 | Luther |
| 4,850,961 A | 7/1989 | Wanderer et al. |
| 4,917,668 A | 4/1990 | Haindl |
| 4,946,133 A | 8/1990 | Johnson et al. |
| 4,948,092 A | 8/1990 | Kasper et al. |
| 4,978,344 A | 12/1990 | Dombrowski et al. |
| 5,000,740 A | 3/1991 | Ducharme et al. |
| 5,032,116 A | 7/1991 | Peterson et al. |
| 5,053,014 A | 10/1991 | Van Heugten |
| 5,092,845 A | 3/1992 | Chang |
| 5,215,525 A | 6/1993 | Sturman |
| 5,215,528 A | 6/1993 | Purdy et al. |
| 5,228,453 A | 7/1993 | Sepetka |
| 5,290,246 A | 3/1994 | Yamamoto et al. |
| 5,328,482 A | 7/1994 | Sircom et al. |
| 5,348,544 A | 9/1994 | Sweeney et al. |
| 5,391,152 A | 2/1995 | Patterson |
| 5,405,323 A | 4/1995 | Rogers et al. |
| 5,417,569 A | 5/1995 | Perisse |
| 5,419,766 A | 5/1995 | Chang et al. |
| 5,423,766 A | 6/1995 | Di Cesare |
| 5,458,658 A | 10/1995 | Sircom |
| 5,501,675 A | 3/1996 | Erskine |
| 5,533,974 A | 7/1996 | Gaba |
| 5,538,508 A | 7/1996 | Steyn |
| 5,558,651 A | 9/1996 | Crawford et al. |
| 5,575,777 A | 11/1996 | Cover et al. |
| 5,584,809 A | 12/1996 | Gaba |
| 5,596,996 A | 1/1997 | Johanson |
| 5,697,907 A | 12/1997 | Gaba |
| 5,718,688 A | 2/1998 | Wozencroft |
| 5,772,636 A | 6/1998 | Brimhall et al. |
| 5,817,069 A | 10/1998 | Arnett |
| 5,851,196 A | 12/1998 | Arnett |
| 5,858,002 A | 1/1999 | Jesch |
| 5,879,337 A | 3/1999 | Kuracina et al. |
| 5,951,515 A | 9/1999 | Osterlind |
| 5,954,698 A | 9/1999 | Pike |
| 5,967,490 A | 10/1999 | Pike |
| 6,001,080 A | 12/1999 | Kuracina et al. |
| 6,042,876 A | 3/2000 | Deem |
| 6,117,108 A | 9/2000 | Woehr et al. |
| 6,213,978 B1 | 4/2001 | Voyten |
| 6,221,047 B1 | 4/2001 | Greene et al. |
| 6,224,569 B1 | 5/2001 | Brimhall et al. |
| 6,379,333 B1 | 4/2002 | Brimhall et al. |
| D459,802 S | 7/2002 | Cindrich |
| 6,425,884 B1 | 7/2002 | Wemmert et al. |
| 6,443,929 B1 | 9/2002 | Kuracina et al. |
| 6,506,181 B2 | 1/2003 | Meng et al. |
| 6,616,630 B1 | 9/2003 | Woehr et al. |
| 6,629,959 B2 | 10/2003 | Kuracina et al. |
| 6,652,486 B2 | 11/2003 | Bialecki et al. |
| 6,709,419 B2 | 3/2004 | Woehr |
| D491,266 S | 6/2004 | Cindrich et al. |
| 6,749,588 B1 | 6/2004 | Howell et al. |
| 6,860,871 B2 | 3/2005 | Kuracina et al. |
| 6,972,002 B2 | 12/2005 | Thorne |
| RE38,996 E | 2/2006 | Crawford et al. |
| 7,226,434 B2 | 6/2007 | Carlyon et al. |
| 7,374,554 B2 | 5/2008 | Menzi et al. |
| 7,500,965 B2 | 3/2009 | Menzi et al. |
| 7,530,965 B2 | 5/2009 | Villa et al. |
| 7,534,231 B2 | 5/2009 | Kuracina et al. |
| 7,597,681 B2 | 10/2009 | Sutton et al. |
| 7,651,476 B2 | 1/2010 | Kohler |
| 7,722,569 B2 | 5/2010 | Soderholm et al. |
| 7,731,687 B2 | 6/2010 | Menzi et al. |
| 7,736,332 B2 | 6/2010 | Carlyon et al. |
| 7,736,339 B2 | 6/2010 | Woehr et al. |
| 7,927,314 B2 | 4/2011 | Kuracina et al. |
| 7,988,664 B2 | 8/2011 | Fiser et al. |
| 8,235,945 B2 | 8/2012 | Baid |
| 8,308,691 B2 | 11/2012 | Woehr et al. |
| 8,328,762 B2 | 12/2012 | Woehr et al. |
| 8,333,735 B2 | 12/2012 | Woehr et al. |
| 8,337,463 B2 | 12/2012 | Woehr et al. |
| 8,348,893 B2 | 1/2013 | Carlyon |
| 8,357,119 B2 | 1/2013 | Stout et al. |
| 8,361,020 B2 | 1/2013 | Stout |
| 8,382,718 B2 | 2/2013 | Woehr |
| 8,388,583 B2 | 3/2013 | Stout et al. |
| 8,414,539 B1 | 4/2013 | Kuracina et al. |
| 8,419,688 B2 | 4/2013 | Woehr et al. |
| 8,444,605 B2 | 5/2013 | Kuracina et al. |
| 8,460,247 B2 | 6/2013 | Woehr et al. |
| 8,469,928 B2 | 6/2013 | Stout et al. |
| 8,496,623 B2 | 7/2013 | Burkholz |
| 8,540,728 B2 | 9/2013 | Woehr et al. |
| 8,545,454 B2 | 10/2013 | Kuracina et al. |
| 8,591,467 B2 | 11/2013 | Walker et al. |
| 8,591,468 B2 | 11/2013 | Woehr et al. |
| 8,597,249 B2 | 12/2013 | Woehr et al. |
| 8,764,711 B2 | 7/2014 | Kuracina et al. |
| 8,827,965 B2 | 9/2014 | Woehr et al. |
| 8,926,564 B2 | 1/2015 | King et al. |
| 9,056,188 B2 | 6/2015 | Hager et al. |
| 9,089,671 B2 | 7/2015 | Stout et al. |
| 9,114,241 B2 | 8/2015 | Stout et al. |
| 9,149,625 B2 | 10/2015 | Woehr et al. |
| 9,149,626 B2 | 10/2015 | Woehr et al. |
| 9,278,180 B2 | 3/2016 | Wong |
| 9,370,641 B2 | 6/2016 | Woehr et al. |
| 9,408,632 B2 | 8/2016 | Erskine |
| 9,592,152 B2 | 3/2017 | Griffis et al. |
| 9,717,886 B2 | 8/2017 | Kuehn et al. |
| 2001/0053895 A1 | 12/2001 | Vaillancourt |
| 2002/0128604 A1 | 9/2002 | Nakajima |
| 2002/0169418 A1 | 11/2002 | Menzi et al. |
| 2003/0060771 A1 | 3/2003 | Bialecki et al. |
| 2004/0116856 A1 | 6/2004 | Woehr et al. |
| 2004/0204689 A1 | 10/2004 | Lynn |
| 2004/0225260 A1 | 11/2004 | Villa et al. |
| 2005/0010176 A1 | 1/2005 | Dikeman et al. |

(56) References Cited

U.S. PATENT DOCUMENTS

| | | |
|---|---|---|
| 2005/0043684 A1 | 2/2005 | Basta et al. |
| 2005/0075609 A1 | 4/2005 | Latona |
| 2005/0113755 A1 | 5/2005 | Greene et al. |
| 2006/0074384 A1 | 4/2006 | Kohler |
| 2006/0155245 A1 | 7/2006 | Woehr |
| 2006/0178635 A1 | 8/2006 | Callaway |
| 2006/0200080 A1 | 9/2006 | Abulhaj |
| 2007/0038186 A1 | 2/2007 | Sutton et al. |
| 2007/0129689 A1 | 6/2007 | Woehr et al. |
| 2007/0176414 A1 | 8/2007 | McBee et al. |
| 2007/0270754 A1* | 11/2007 | Soderholm ....... A61M 25/0637 604/164.08 |
| 2008/0097343 A1 | 4/2008 | Woehr |
| 2008/0140011 A1 | 6/2008 | Hager et al. |
| 2008/0208132 A1 | 8/2008 | Funamura et al. |
| 2008/0243086 A1 | 10/2008 | Hager et al. |
| 2009/0137958 A1 | 5/2009 | Erskine |
| 2009/0182280 A1 | 7/2009 | Glowacki et al. |
| 2009/0312711 A1 | 12/2009 | Brimhall |
| 2010/0137815 A1 | 6/2010 | Kuracina et al. |
| 2010/0191189 A1 | 7/2010 | Harding et al. |
| 2010/0204648 A1 | 8/2010 | Stout et al. |
| 2010/0204660 A1 | 8/2010 | McKinnon et al. |
| 2010/0217208 A1 | 8/2010 | Snow |
| 2011/0054402 A1 | 3/2011 | Tanabe et al. |
| 2011/0054403 A1* | 3/2011 | Tanabe .................. A61M 5/158 604/164.01 |
| 2011/0060286 A1 | 3/2011 | Tanabe et al. |
| 2011/0160662 A1 | 6/2011 | Stout et al. |
| 2011/0160671 A1 | 6/2011 | Tanabe et al. |
| 2011/0288482 A1 | 11/2011 | Farrell et al. |
| 2011/0301551 A1 | 12/2011 | Koehler et al. |
| 2012/0078200 A1 | 3/2012 | Woehr et al. |
| 2012/0123354 A1 | 5/2012 | Woehr |
| 2012/0136311 A1 | 5/2012 | Knutsson et al. |
| 2012/0220957 A1 | 8/2012 | Kuracina et al. |
| 2012/0238966 A1* | 9/2012 | Kuracina ............ A61M 5/3273 604/263 |
| 2012/0277679 A1 | 11/2012 | Steube |
| 2013/0030370 A1 | 1/2013 | Walker et al. |
| 2013/0090607 A1 | 4/2013 | McKinnon et al. |
| 2013/0096504 A1 | 4/2013 | Walker et al. |
| 2013/0184645 A1* | 7/2013 | Baid ................. A61M 25/0618 604/164.08 |
| 2013/0226141 A1 | 8/2013 | King et al. |
| 2013/0245567 A1 | 9/2013 | Tremblay |
| 2013/0253443 A1 | 9/2013 | Woehr et al. |
| 2013/0324930 A1 | 12/2013 | Fuchs et al. |
| 2014/0012203 A1 | 1/2014 | Woehr et al. |
| 2014/0018738 A1 | 1/2014 | Steube |
| 2014/0058329 A1 | 2/2014 | Walker et al. |
| 2014/0276434 A1 | 9/2014 | Woehr et al. |
| 2014/0303561 A1 | 10/2014 | Li |
| 2014/0364809 A1 | 12/2014 | Isaacson et al. |
| 2015/0151088 A1 | 6/2015 | Lim et al. |
| 2015/0238733 A1 | 8/2015 | bin Abdulla |
| 2016/0106959 A1 | 4/2016 | Woehr |
| 2016/0158503 A1 | 6/2016 | Woehr |
| 2016/0158526 A1 | 6/2016 | Woehr |

FOREIGN PATENT DOCUMENTS

| | | |
|---|---|---|
| CA | 2133053 A1 | 3/1995 |
| CN | 202682467 U | 1/2013 |
| CN | 203196075 U | 9/2013 |
| CN | 203493994 U | 3/2014 |
| CN | 106470607 A | 3/2017 |
| EP | 0352928 A1 | 1/1990 |
| EP | 2204204 A1 | 7/2010 |
| EP | 2228093 A1 | 9/2010 |
| EP | 2343095 A1 | 7/2011 |
| EP | 2489393 A1 | 8/2012 |
| EP | 2566543 A1 | 3/2013 |
| JP | H1057497 | 3/1998 |
| JP | 2002126080 A | 5/2002 |
| JP | 2002263197 A | 9/2002 |
| JP | 2008-173206 A | 7/2008 |
| JP | 2010099534 A | 5/2010 |
| JP | 2011-115630 A | 6/2011 |
| JP | 3170612 U | 8/2011 |
| JP | 2013-192868 A | 9/2013 |
| WO | WO-1993005840 A2 | 4/1993 |
| WO | WO-1995022364 A1 | 8/1995 |
| WO | WO-2001012249 A1 | 2/2001 |
| WO | 0193940 A2 | 12/2001 |
| WO | 0195958 A1 | 12/2001 |
| WO | WO-0193940 A2 | 12/2001 |
| WO | WO-2003011381 A1 | 2/2003 |
| WO | WO-2004004819 A1 | 1/2004 |
| WO | WO-2005042073 A1 | 5/2005 |
| WO | 2008064332 A2 | 5/2008 |
| WO | WO-2009142878 A1 | 11/2009 |
| WO | WO-2013/014639 A1 | 1/2013 |
| WO | WO-2013016373 A1 | 1/2013 |
| WO | WO-2013/051242 A1 | 4/2013 |
| WO | WO-2013052666 A1 | 4/2013 |
| WO | WO-2013137348 A1 | 9/2013 |
| WO | WO-2014/054166 A1 | 4/2014 |
| WO | WO-2014126865 A1 | 8/2014 |
| WO | WO-2014197656 A1 | 12/2014 |
| WO | WO-2015024904 A1 | 2/2015 |

OTHER PUBLICATIONS

US 5,755,409, 08/1979, Sigmund (withdrawn)
Singapore Office Action dated Nov. 12, 2019 in Singapore Patent Application No. 11201708371S.
Brazilian Office Action dated Feb. 4, 2020 in Brazilian Patent Application No. 112015030658-6.
Singapore Office Action dated Jan. 29, 2020 in Singapore Patent Application No. 11201706370P.
Japanese Office Action dated Jan. 28, 2020 in Japanese Patent Application No. 2017-554341.

\* cited by examiner

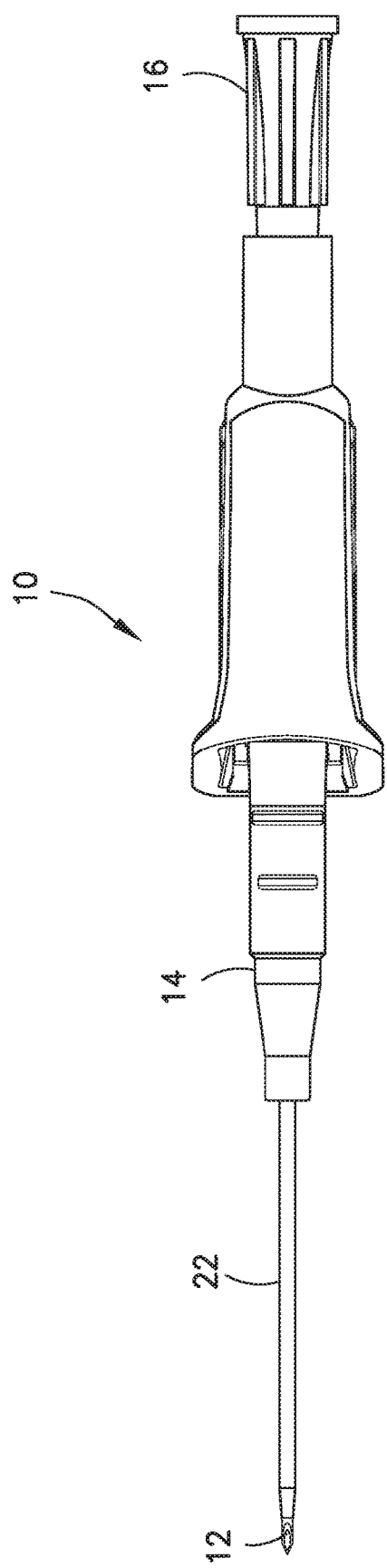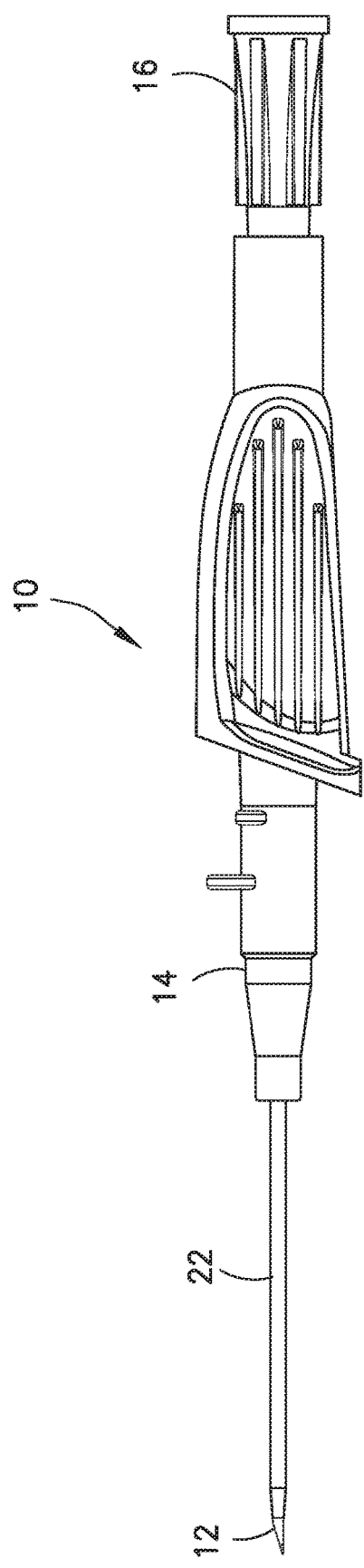

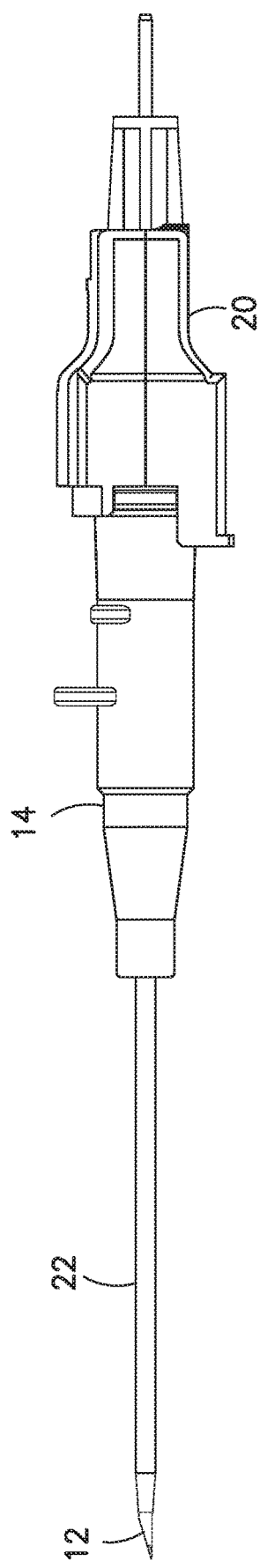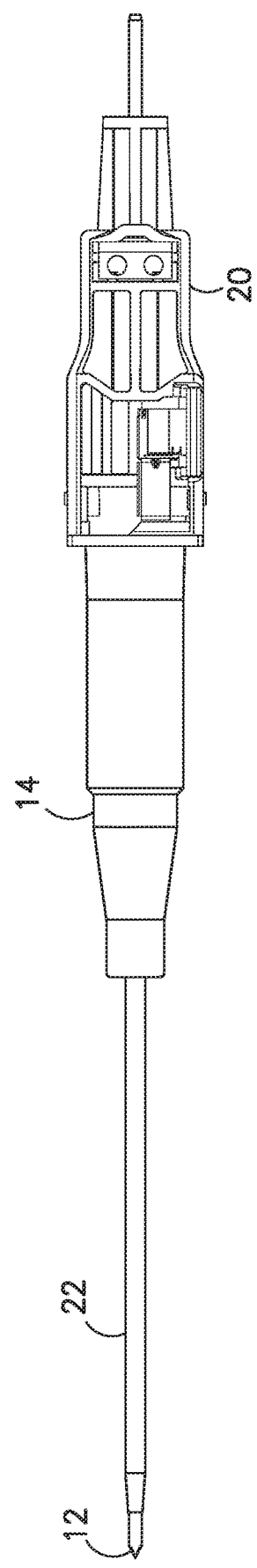

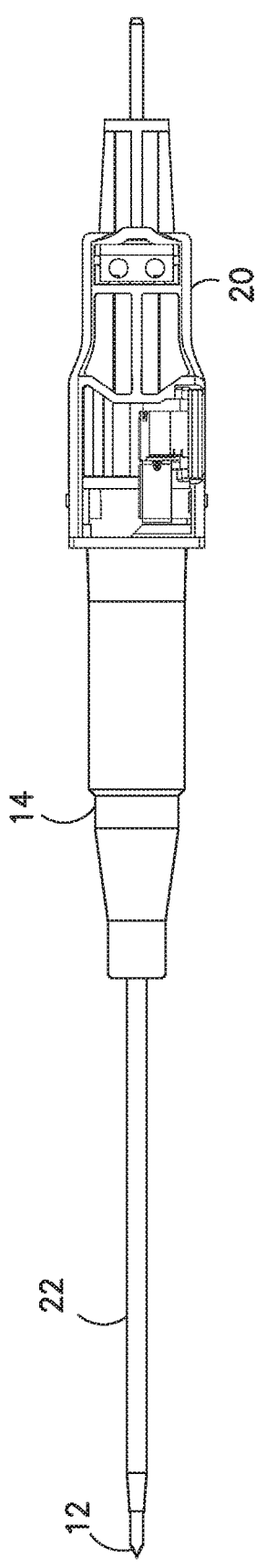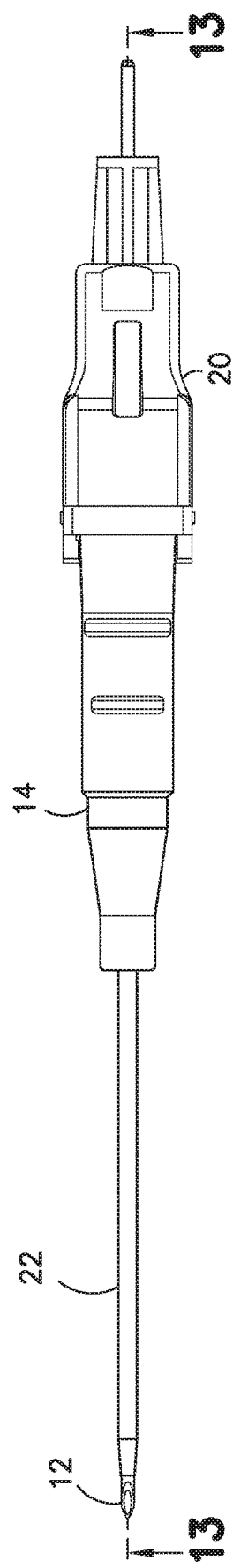
FIG. 11
FIG. 12

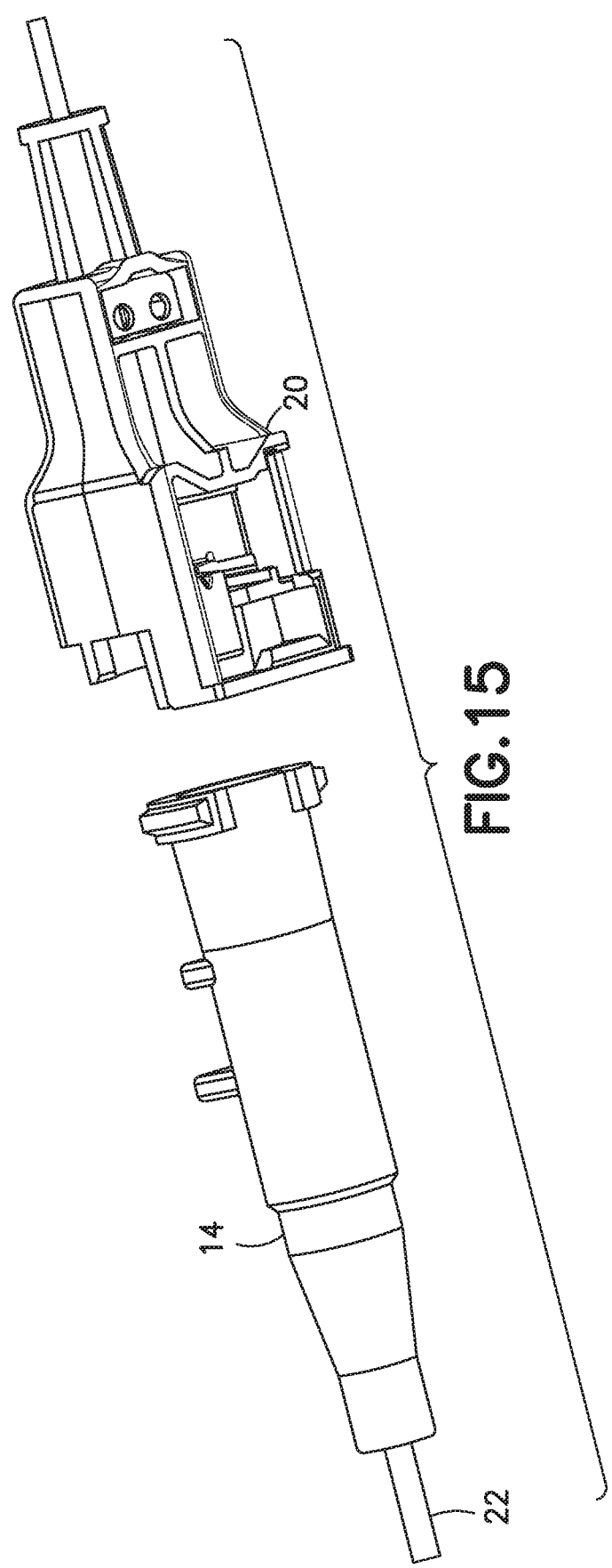

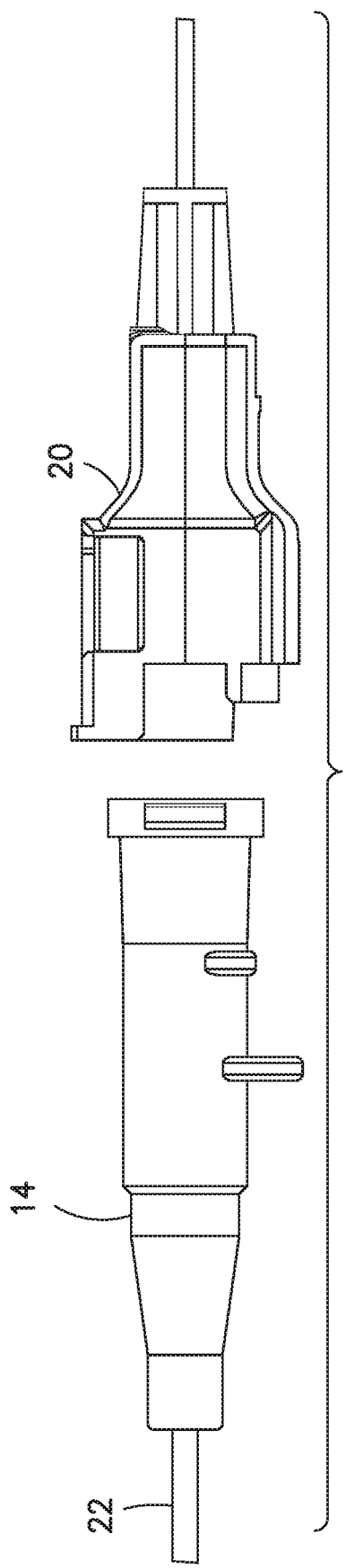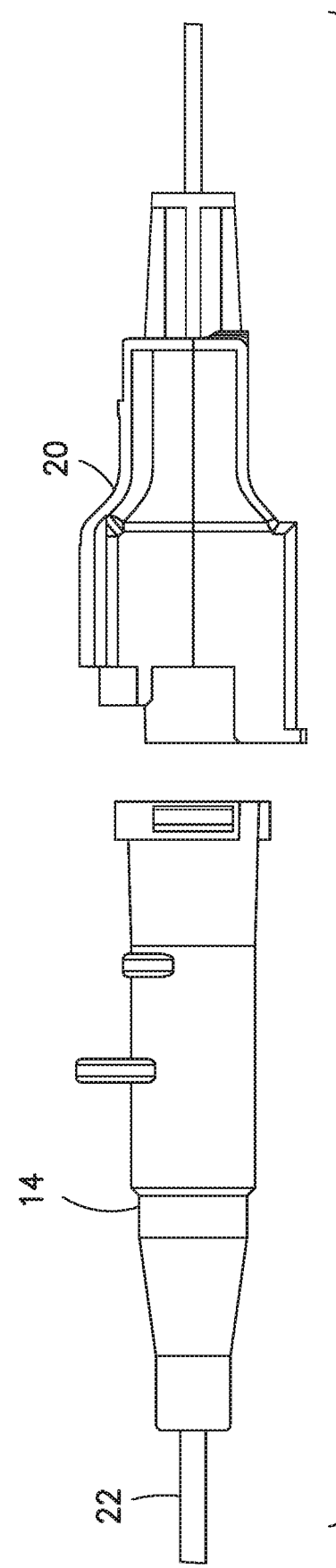

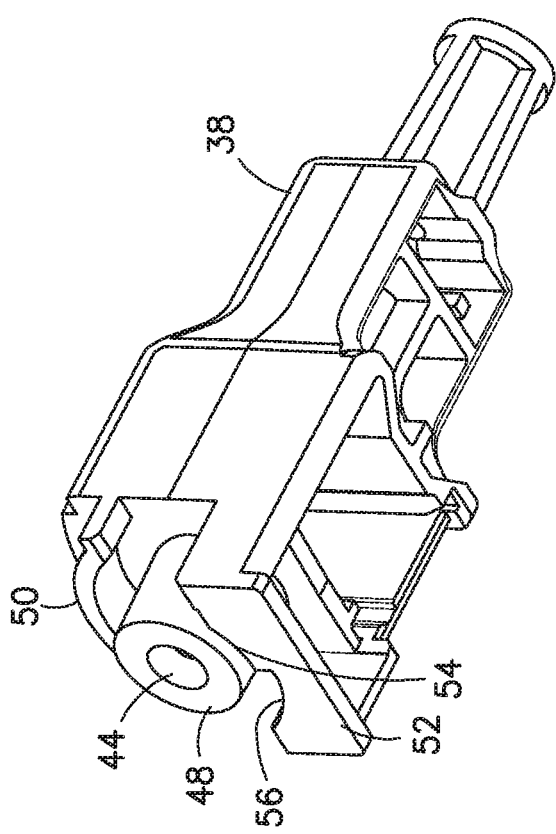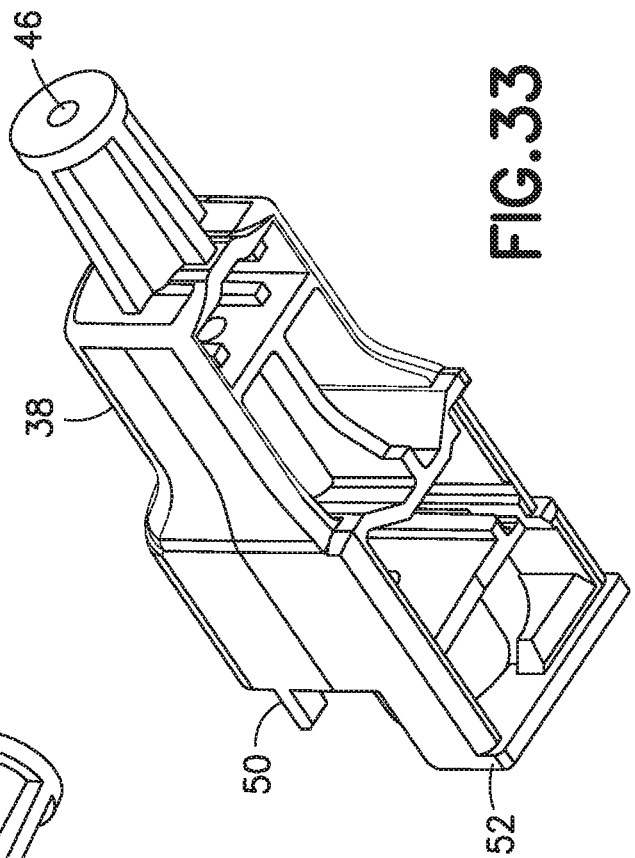

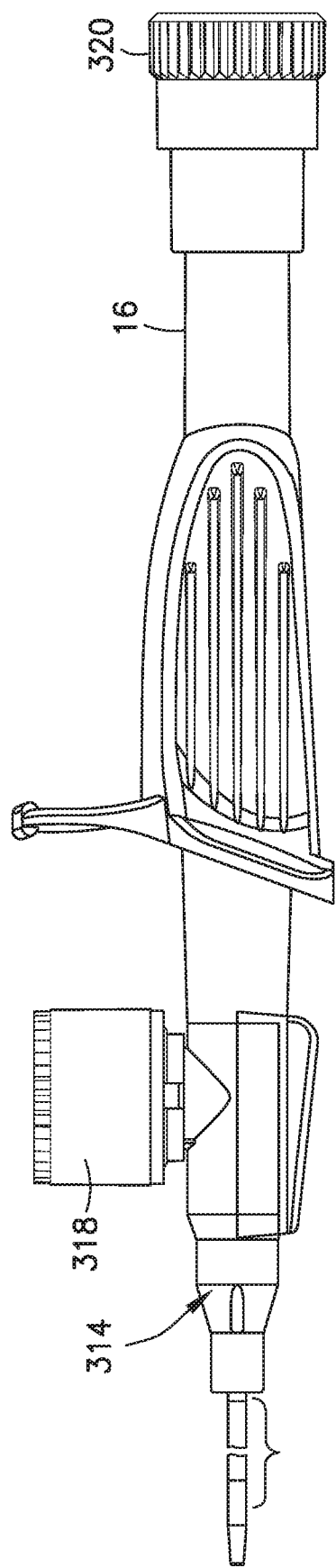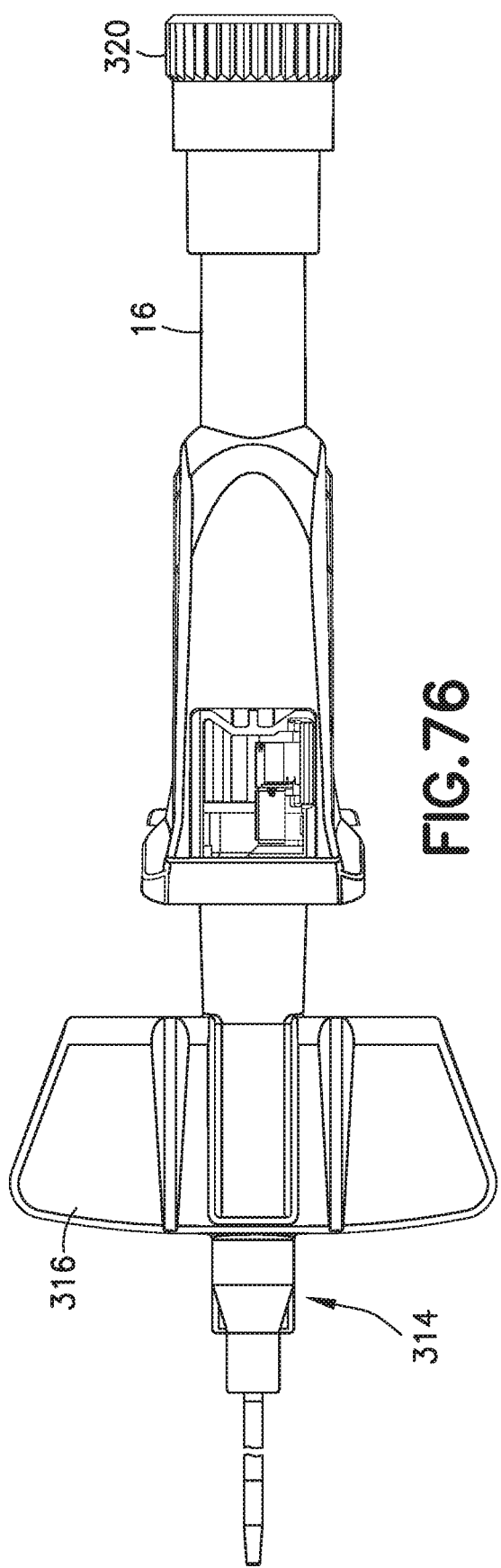

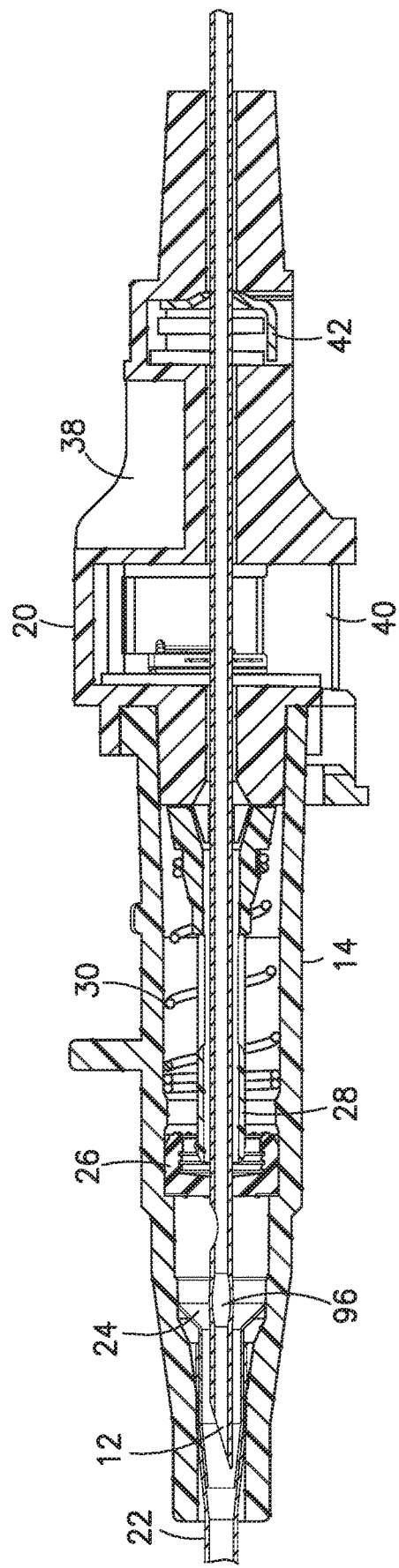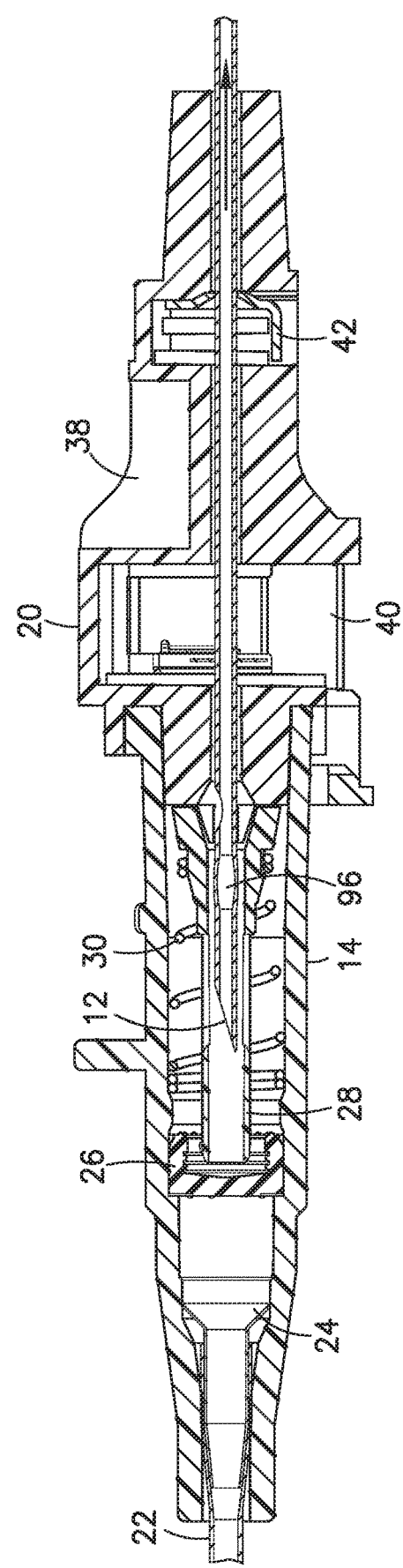

NEEDLE CAPTURE SAFETY INTERLOCK FOR CATHETER

RELATED APPLICATIONS

This application claims the benefit under 35 U.S.C. § 119(e) of U.S. Provisional Patent Application Ser. 61/981,223, filed on Apr. 18, 2014, U.S. Provisional Application 61/981,312, filed on Apr. 18, 2014, and U.S. Provisional Patent Application Ser. No. 62/07,760, filed on Nov. 10, 2014. Each of the above applications is hereby incorporated by reference in its entirety.

FIELD

Various exemplary embodiments of the invention relate to catheters.

BACKGROUND

Catheter assemblies are used to place a catheter properly into the vascular system of a patient. Once in place, catheters such as intravenous catheters may be used to infuse fluids including normal saline, medicinal compounds, and/or nutritional compositions into a patient in need of such treatment. Catheters additionally enable the removal of fluids from the circulatory system and monitoring of conditions within the vascular system of the patient.

SUMMARY OF THE INVENTION

It is an aspect of the present invention to provide a catheter assembly in which an improved clip and needle shield are used for needle protection. The improved arrangement is more compact, provides increased needle protection, and reduces the size and complexity of the catheter assembly. The addition of a release notch in a collar of a catheter hub and disengagement of the clip via the notch allows the needle shield to be more compact than in the prior art. In the prior art, without the notch, the clip has to travel a longer distance to disengage the catheter hub. In addition, the width of the needle shield is reduced by an improved attachment interface between the clip and the needle shield. Specifically, a spade attaches the clip to the needle shield with an outer surface of the spade exposed to an outside of the needle shield.

The foregoing and/or other aspects of the present invention can be achieved by providing a catheter assembly comprising a catheter, a needle having a sharp distal tip disposed in the catheter, a catheter hub housing the catheter and the needle, the catheter hub having a notch, a needle shield connected to the catheter hub when the needle is in a first position, and a clip disposed in the needle shield that cooperates with the needle, wherein the clip engages the collar in the first position of the needle, the clip disengages the collar via the notch when the needle is retracted to a second position to enclose at least a portion of the needle.

The foregoing and/or other aspects of the present invention can be achieved by also providing a catheter assembly comprising a catheter, a needle having a sharp distal tip disposed in the catheter, a catheter hub housing the catheter and the needle, a needle shield configured to be connected to the catheter hub, and a clip disposed in the needle shield that cooperates with the needle, the clip including a spade that attaches the clip to the needle shield, wherein an outer surface of the spade is exposed to an outside of the catheter assembly.

The foregoing and/or other aspects of the present invention can be achieved by further providing a method of operating a catheter assembly comprising disposing a needle having a sharp distal tip in a catheter, biasing a clip when the needle is in use in a first position, removing the needle from a catheter hub having a notch, releasing the clip when the needle is in a second position to enclose at least a portion of the needle, and disengaging the clip from the collar via the notch when the needle is in the second position.

BRIEF DESCRIPTION OF THE DRAWINGS

The above aspects and features of the present invention will be more apparent from the description for the exemplary embodiments of the present invention taken with reference to the accompanying drawings, in which:

FIG. 4 illustrates a top plan view of the catheter assembly;

FIG. 5 illustrates a right side elevation view of the catheter assembly;

FIG. 9 illustrates a right side elevation view of the assembled catheter hub, needle shield, and needle of the catheter assembly;

FIG. 10 illustrates a bottom plan view of the assembled catheter hub, needle shield, and needle of the catheter assembly;

FIG. 11 illustrates a bottom plan view of the assembled catheter hub, needle shield, and needle of the catheter assembly;

FIG. 12 illustrates a top plan view of the assembled catheter hub, needle shield, and needle of the catheter assembly;

FIG. 15 illustrates a right perspective view of the separated catheter hub, needle shield, and needle of the catheter assembly;

FIG. 16 illustrates a right side elevation view of the separated catheter hub, needle shield, and needle of the catheter assembly;

FIG. 17 illustrates a second right side elevation view of the separated catheter hub, needle shield, and needle of the catheter assembly;

FIG. 32 illustrates a second left perspective view of the needle shield outer housing of the catheter assembly;

FIG. 33 illustrates a second right perspective view of the needle shield outer housing of the catheter assembly;

FIG. 75 illustrates a right side view of the alternative side port catheter hub assembly with a needle shield and needle hub;

FIG. 76 illustrates a bottom plan view of the alternative side port catheter hub assembly with a needle shield and needle hub;

FIG. 77 illustrates a cross sectional view of the catheter assembly of FIGS. 1-12 as the introducer needle is being withdrawn;

FIG. 78 illustrates a second cross sectional view of the catheter assembly of FIGS. 1-12 as the introducer needle is being withdrawn;

DETAILED DESCRIPTION OF EXEMPLARY EMBODIMENTS

Figure 1:
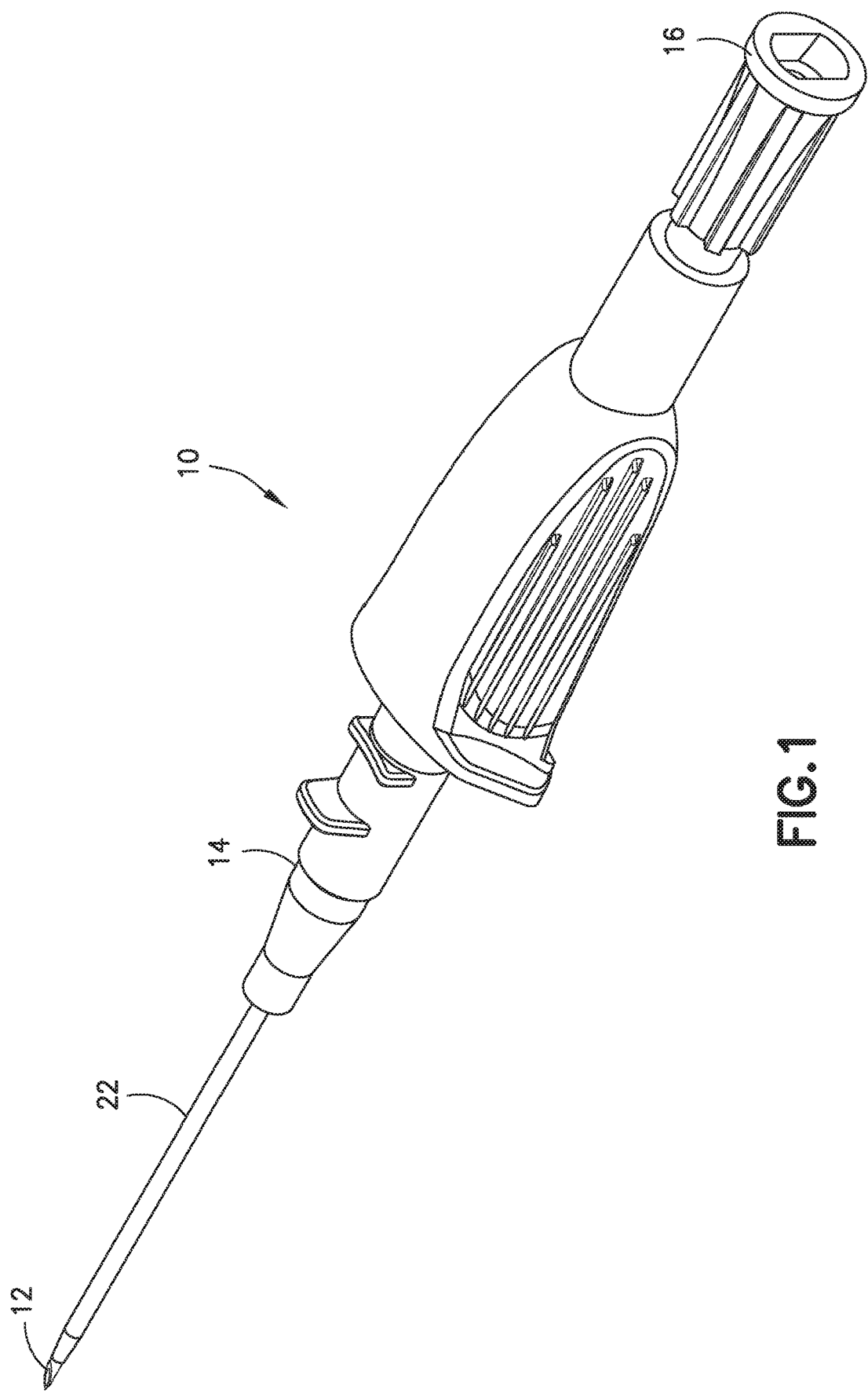
FIG. 1 illustrates a top left perspective view of a catheter assembly in accordance with an embodiment of the present invention.
Figure 2:
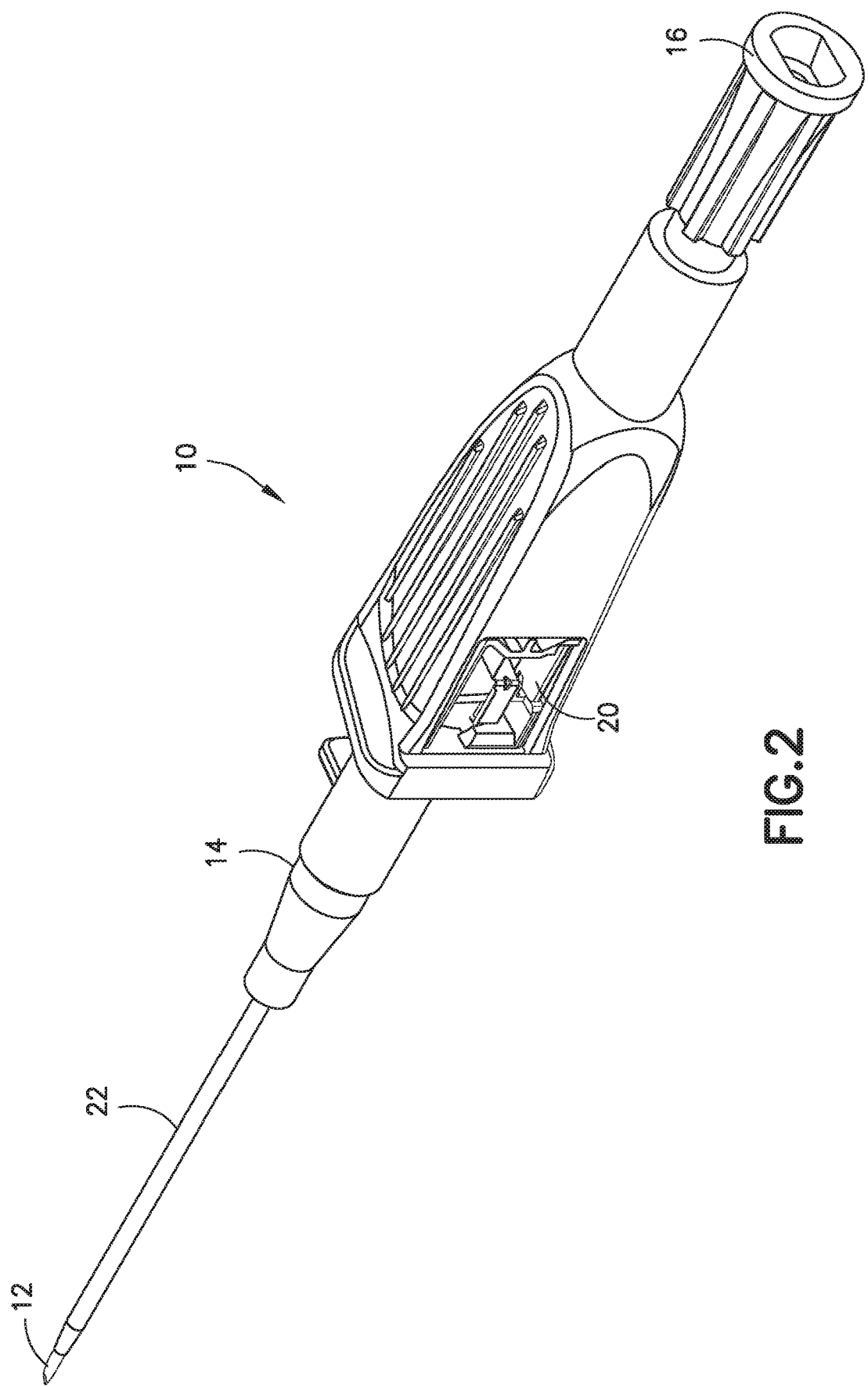
FIG. 2 illustrates a side left perspective view of a catheter assembly.
Figure 3:
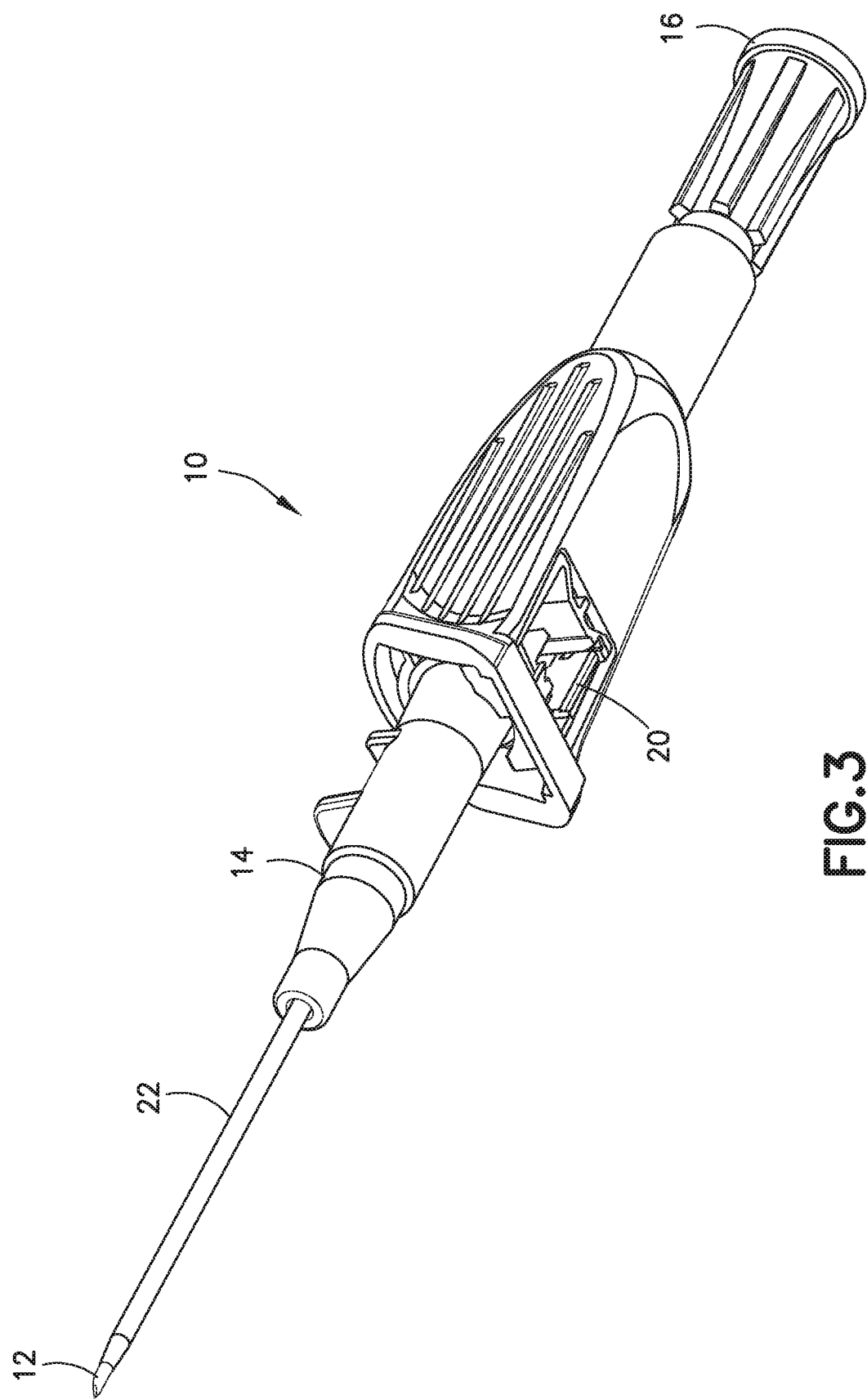
FIG. 3 illustrates an alternate side left perspective view of a catheter assembly.
Figure 6:
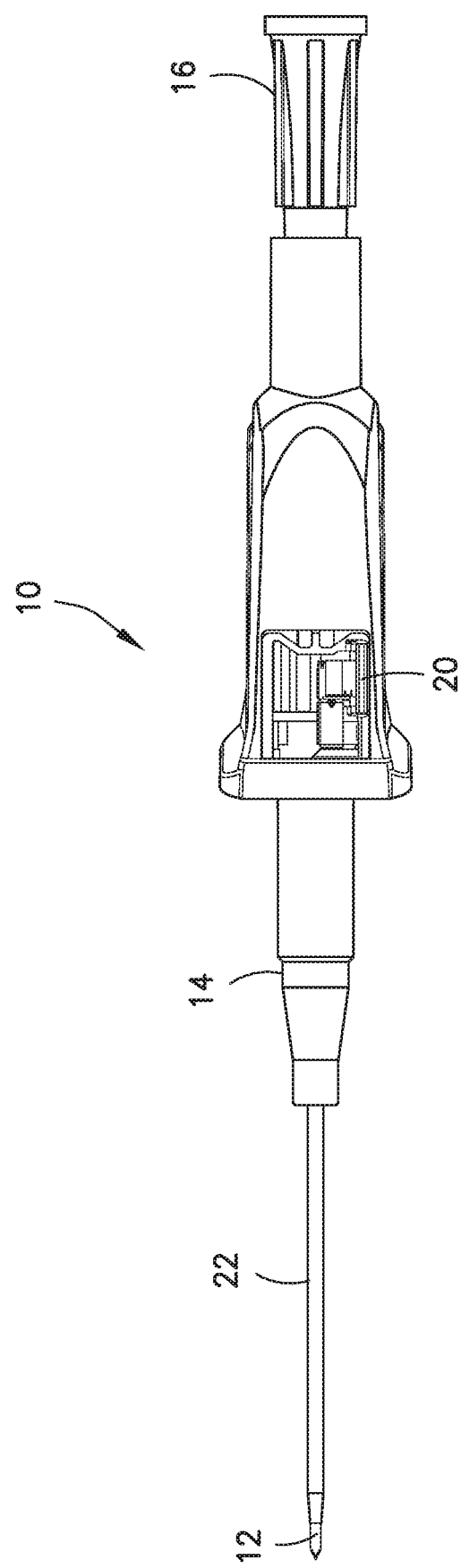
FIG. 6 illustrates a bottom plan view of the catheter assembly.
Figure 7:
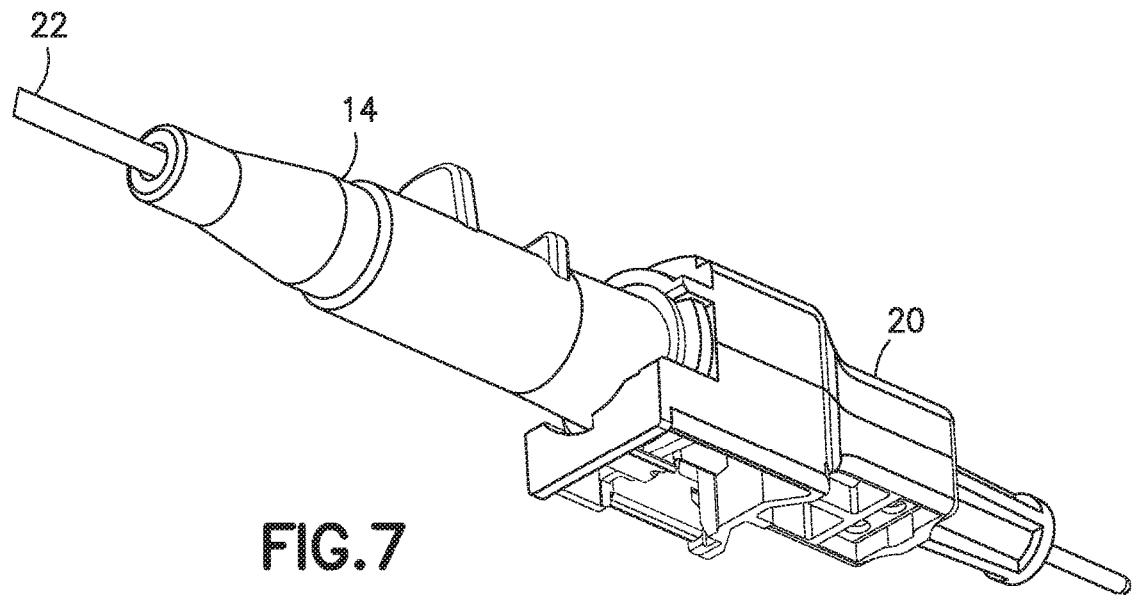
FIG. 7 illustrates a left perspective view of the assembled catheter hub, needle shield, and needle of the catheter assembly.
Figure 8:
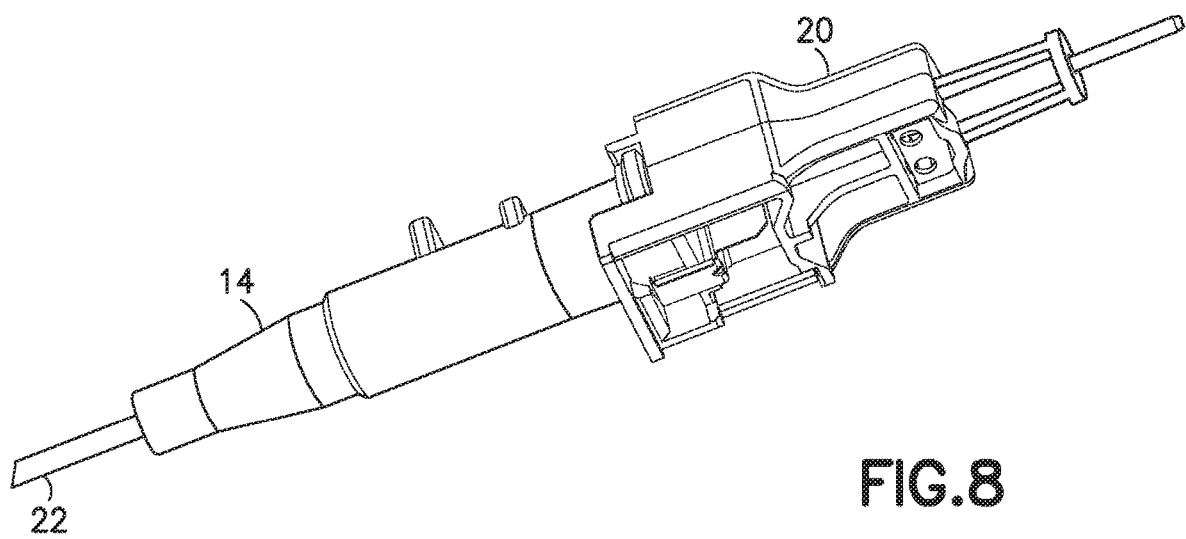
FIG. 8 illustrates a right perspective view of the assembled catheter hub, needle shield, and needle of the catheter assembly.
Figure 13:
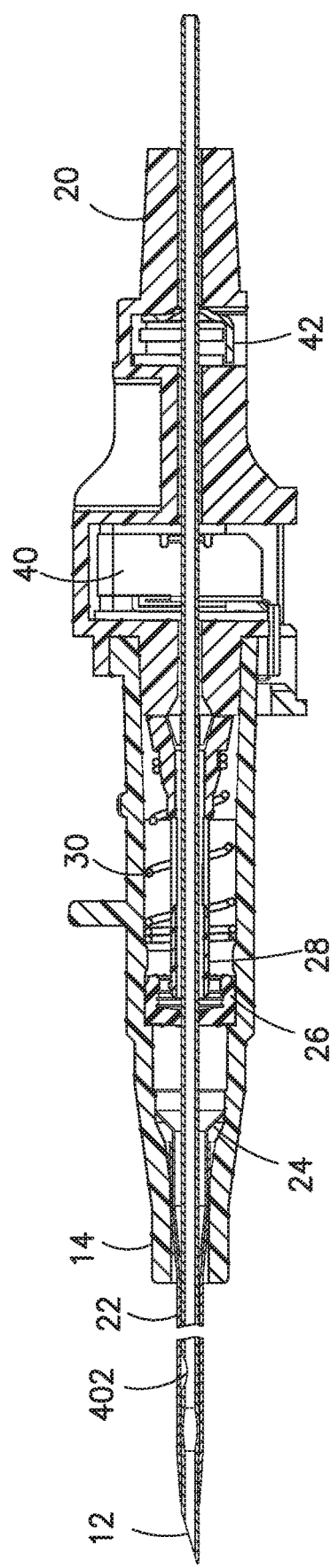
FIG. 13 illustrates a cross sectional view of a right side elevation view of the assembled catheter hub, needle shield, and needle of the catheter assembly.
Figure 14:
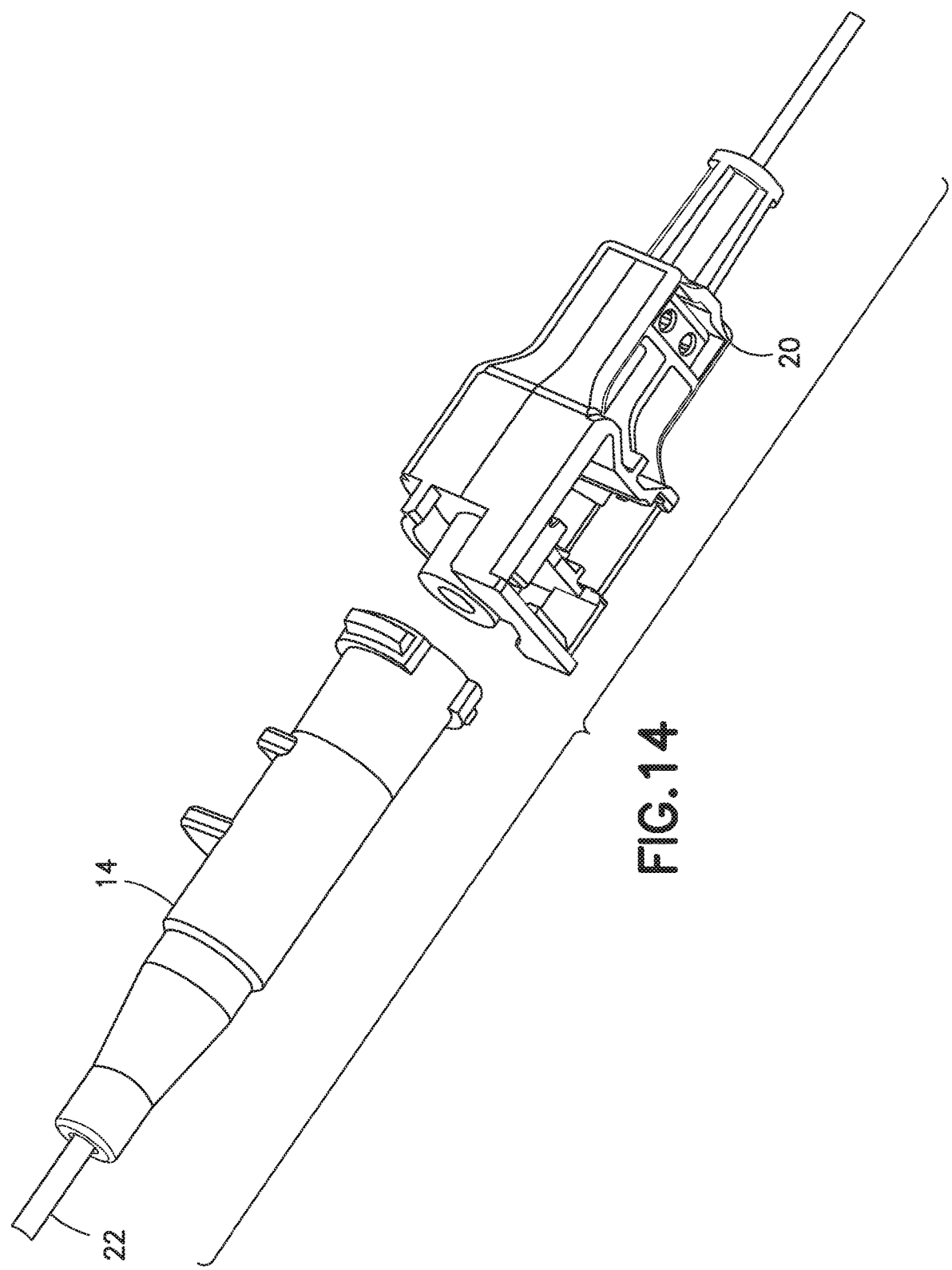
FIG. 14 illustrates a left perspective view of the separated catheter hub, needle shield, and needle of the catheter assembly.
Figure 18:
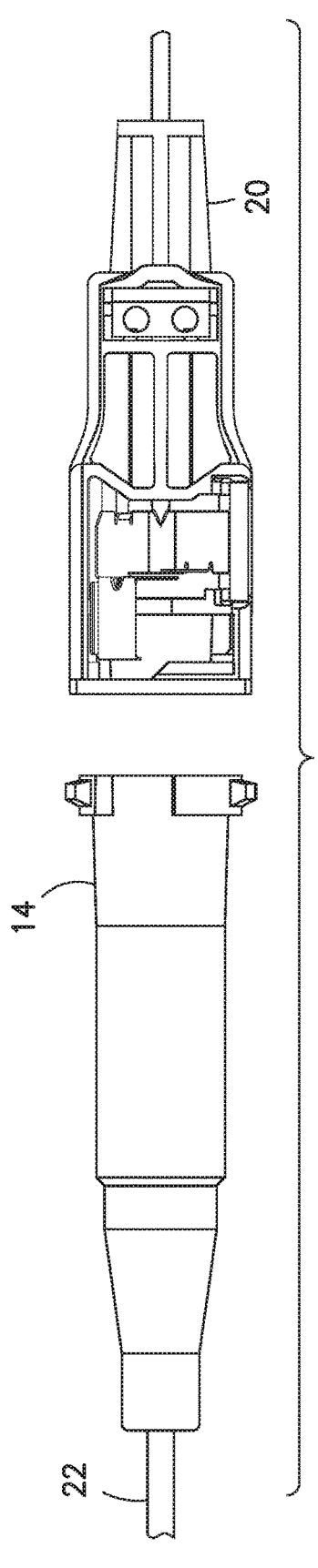
FIG. 18 illustrates a bottom plan view of the separated catheter hub, needle shield, and needle of the catheter assembly.
Figure 19:
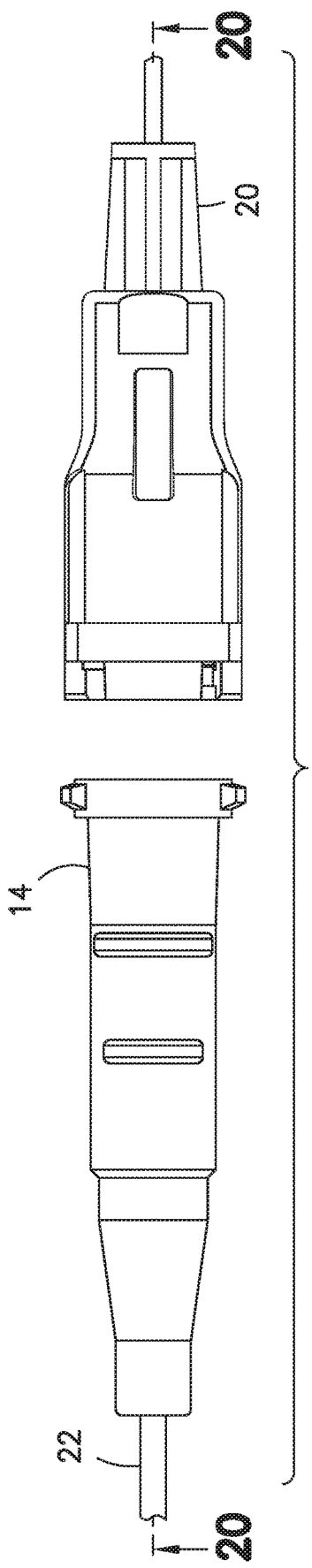
FIG. 19 illustrates a top plan view of the separated catheter hub, needle shield, and needle of the catheter assembly.
Figure 20:
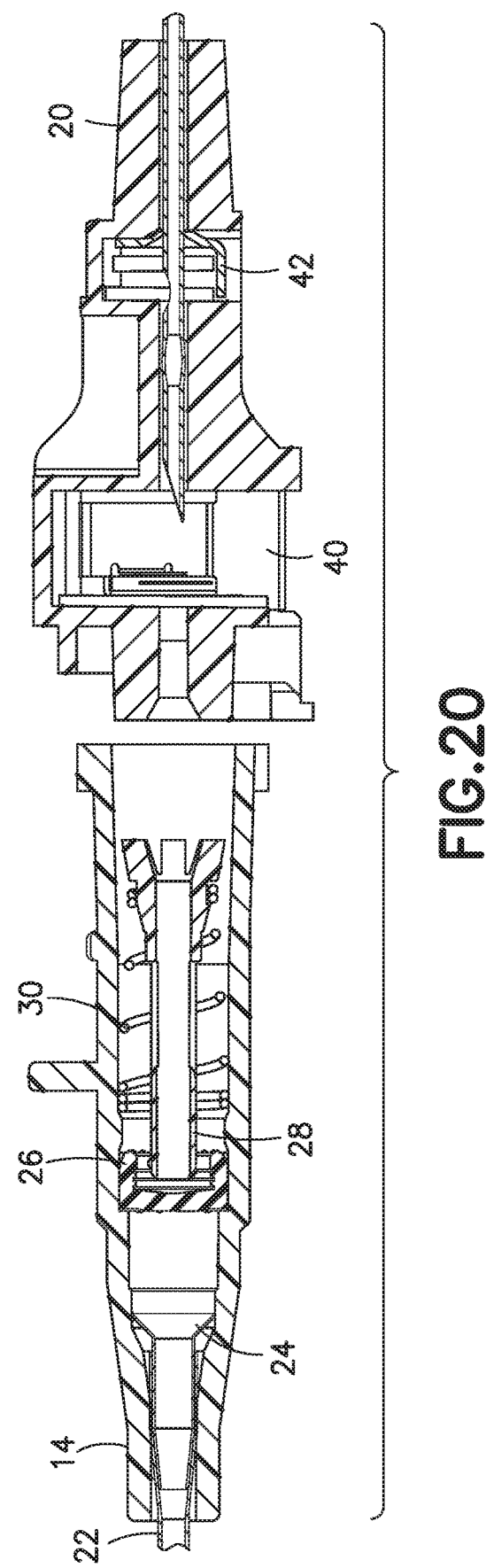
FIG. 20 illustrates a cross sectional view of a right side elevation view of the separated catheter hub, needle shield, and needle of the catheter assembly.
Figure 21:
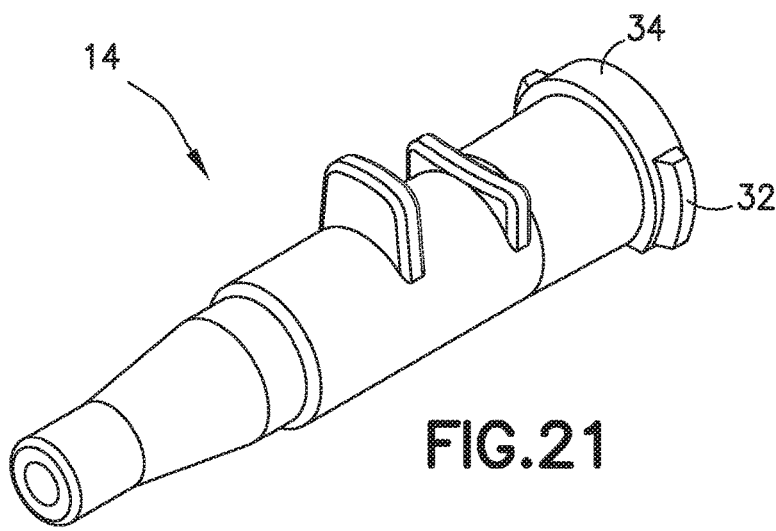
FIG. 21 is a right perspective view of the catheter hub of the catheter assembly.
Figure 22:
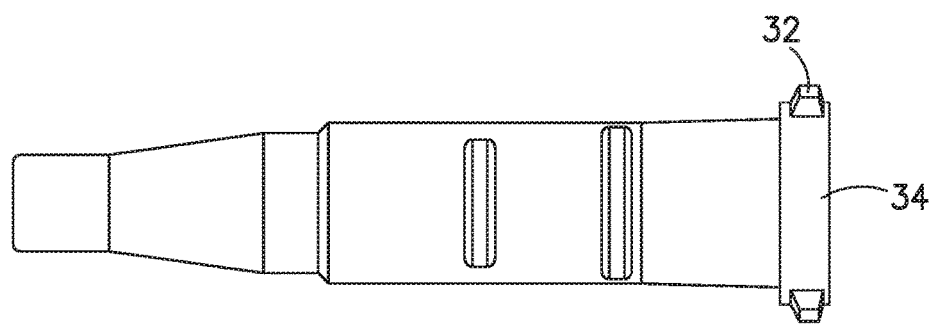
FIG. 22 is a top plan view of the catheter hub of the catheter assembly.
Figure 23:
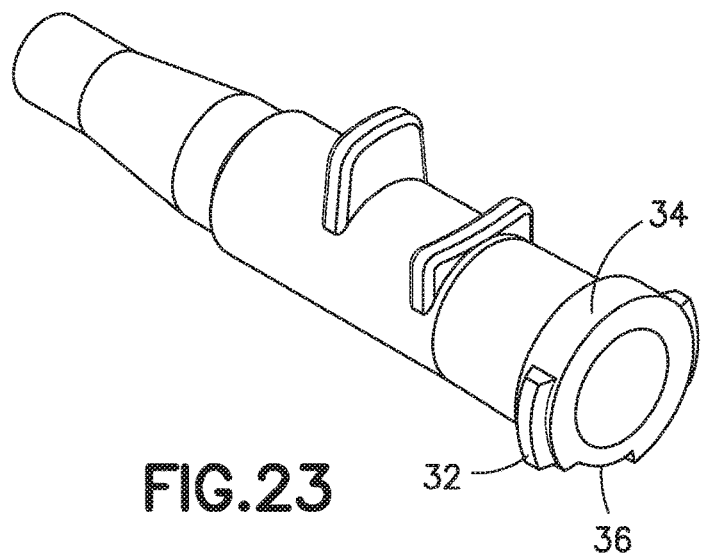
FIG. 23 is a left perspective view of the catheter hub of the catheter assembly.
Figure 24:
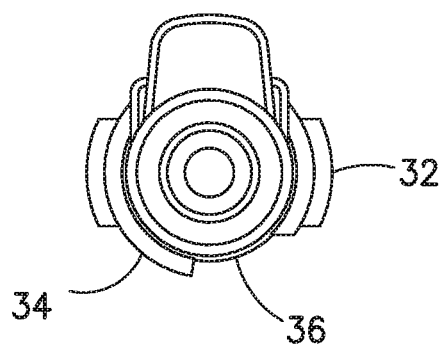
FIG. 24 is a front side view of the catheter hub of the catheter assembly.
Figure 25:
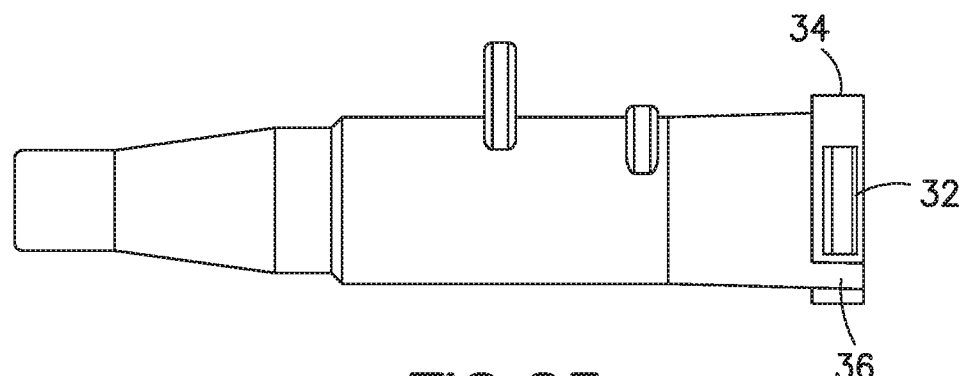
FIG. 25 is a right side view of the catheter hub of the catheter assembly.
Figure 26:
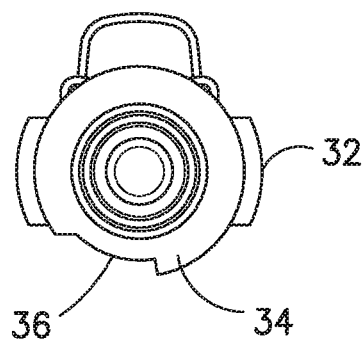
FIG. 26 is a rear side view of the catheter hub of the catheter assembly.
Figure 27:
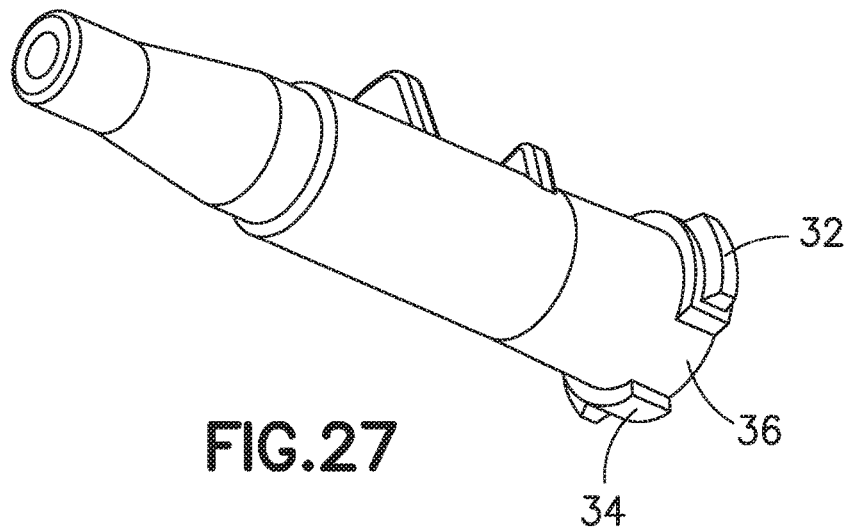
FIG. 27 is a left perspective view of the catheter hub of the catheter assembly.
Figure 28:
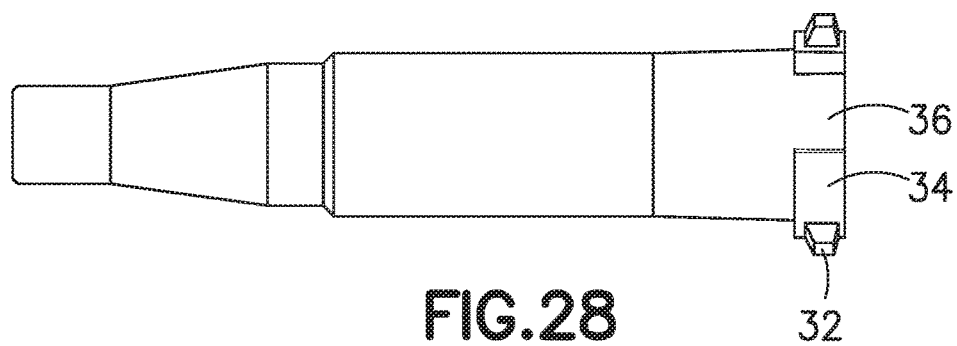
FIG. 28 is a bottom plan view of the catheter hub of the catheter assembly.
Figure 29:
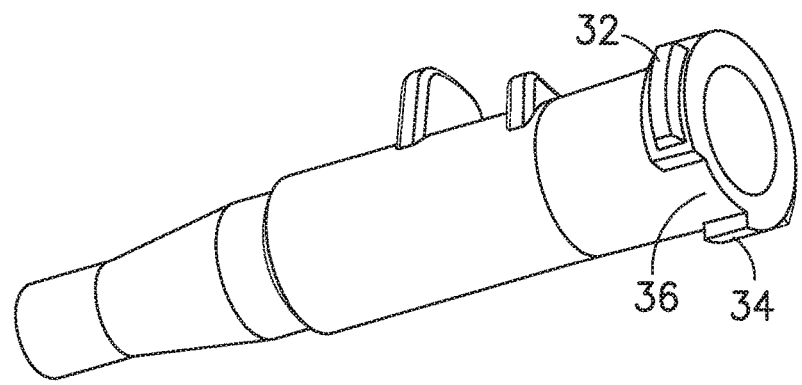
FIG. 29 is a right perspective view of the catheter hub of the catheter assembly.
Figure 30:
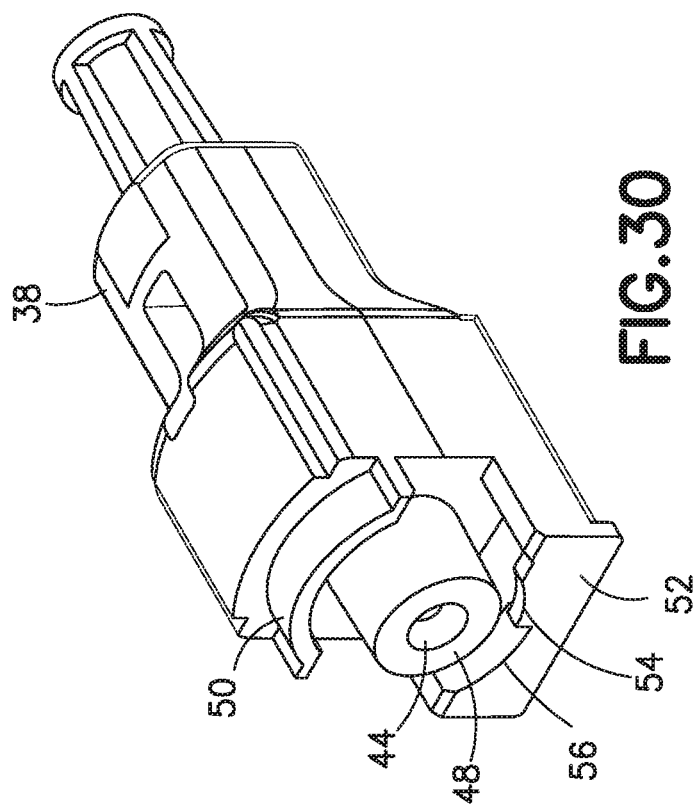
FIG. 30 illustrates a right perspective view of the needle shield outer housing of the catheter assembly.
Figure 31:
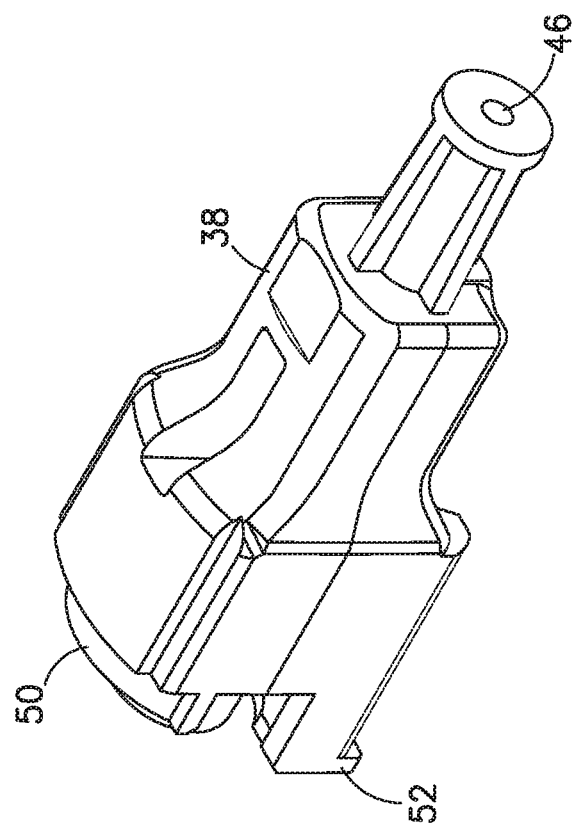
FIG. 31 illustrates a left perspective view of the needle shield outer housing of the catheter assembly.
Figure 34:
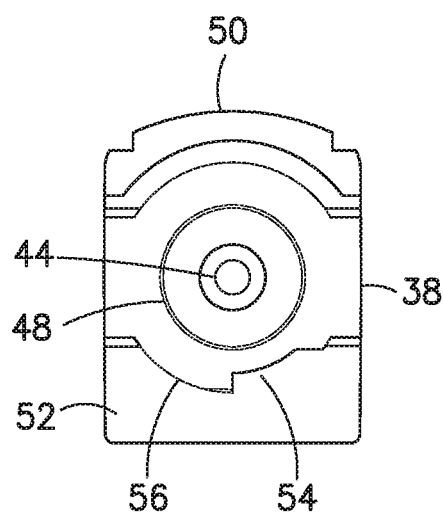
FIG. 34 illustrates a front side elevation view of the needle shield outer housing of the catheter assembly.
Figure 35:
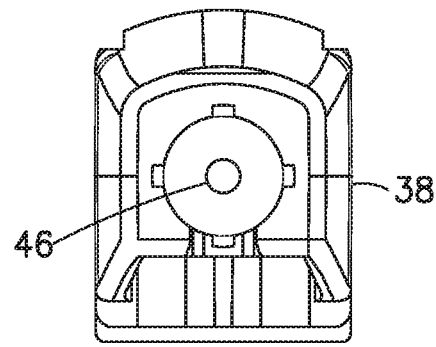
FIG. 35 illustrates a rear side elevation view of the needle shield outer housing of the catheter assembly.
Figure 36:
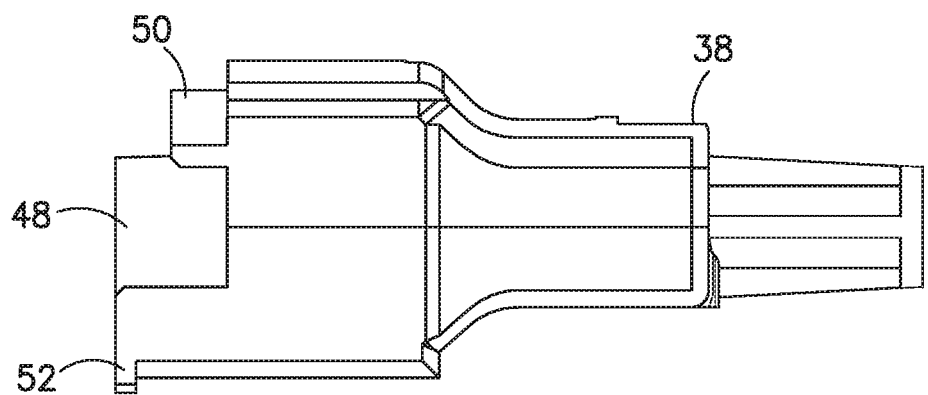
FIG. 36 illustrates a right side elevation view of the needle shield outer housing of the catheter assembly.
Figure 37:
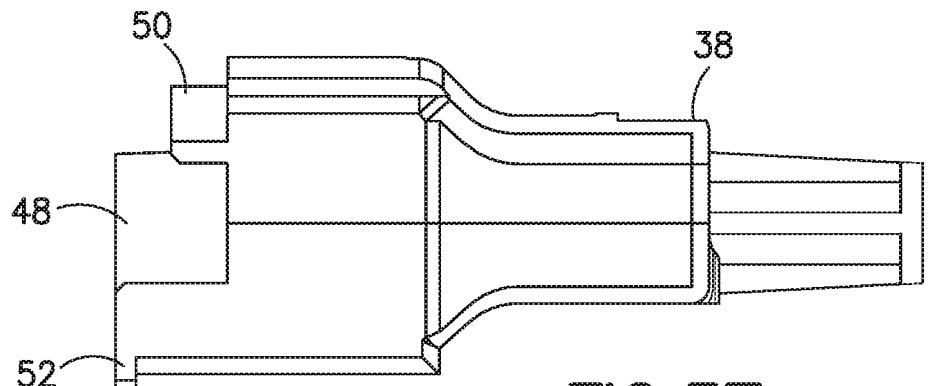
FIG. 37 illustrates a right side elevation view of the needle shield outer housing of the catheter assembly.
Figure 38:
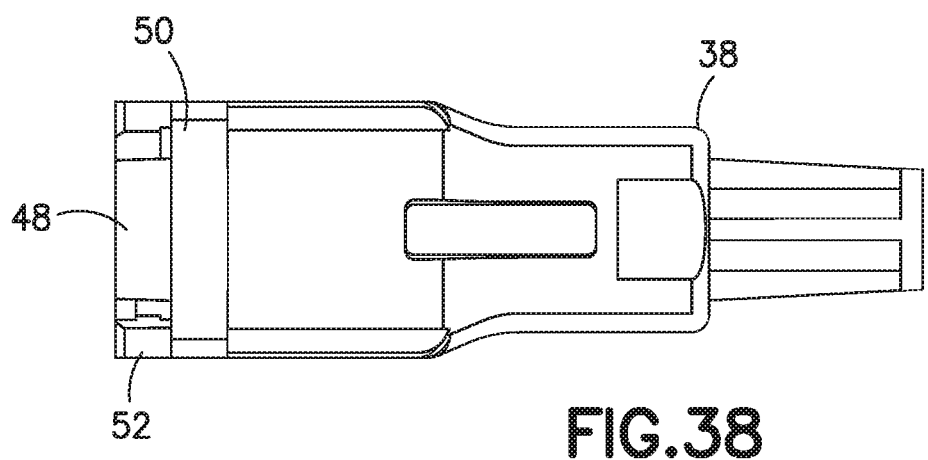
FIG. 38 illustrates a top plan view of the needle shield outer housing of the catheter assembly.
Figure 39:
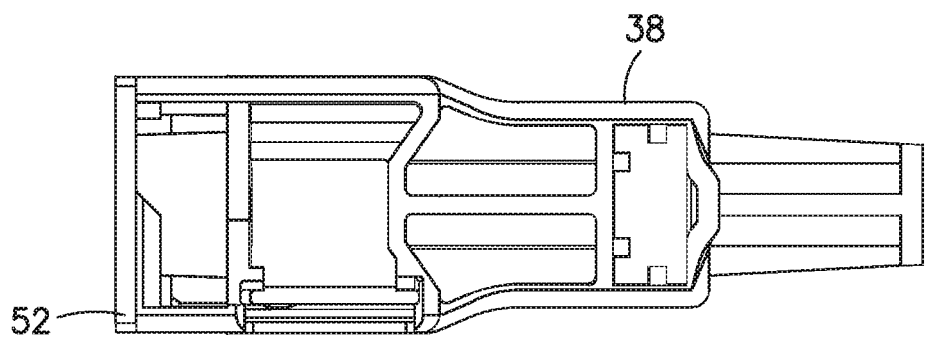
FIG. 39 illustrates a bottom plan view of the needle shield outer housing of the catheter assembly.
Figure 40:
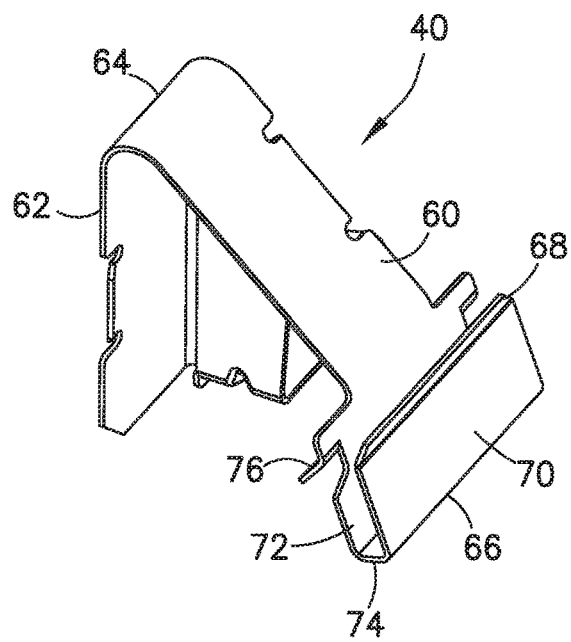
FIG. 40 illustrates a left perspective view of the V-shaped metal clip of the catheter assembly.
Figure 41:
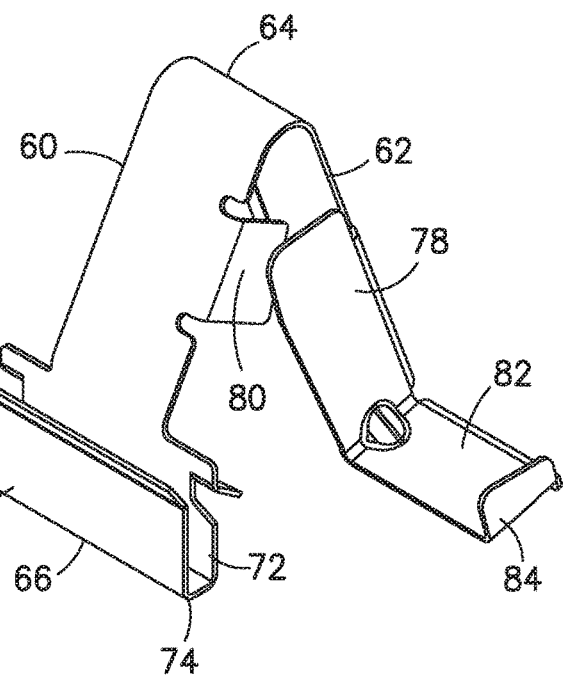
FIG. 41 illustrates a right perspective view of the V-shaped metal clip of the catheter assembly.
Figure 42:
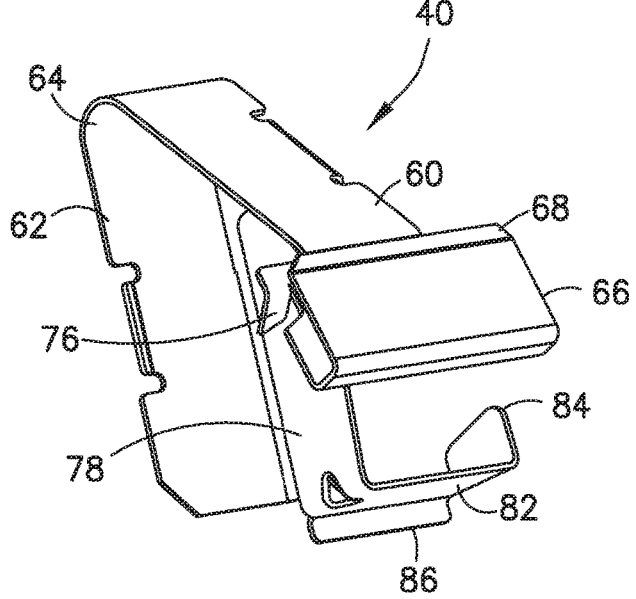
FIG. 42 illustrates a second right perspective view of the V-shaped metal clip of the catheter assembly.
Figure 43:
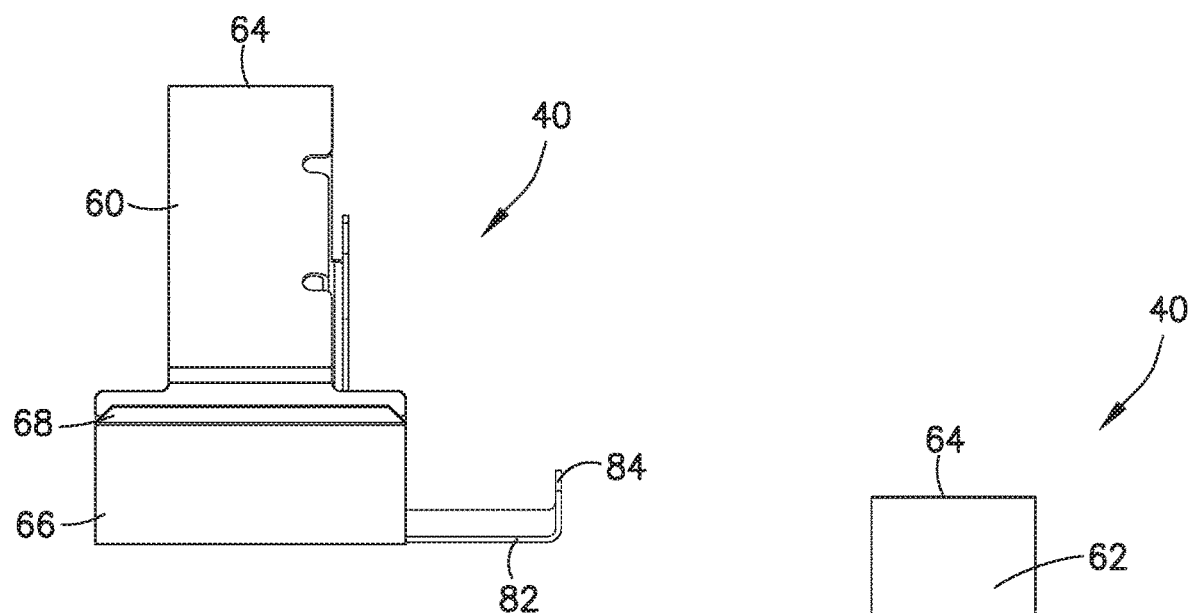
FIG. 43 illustrates a front elevation view of the V-shaped metal clip of the catheter assembly.
Figure 44:
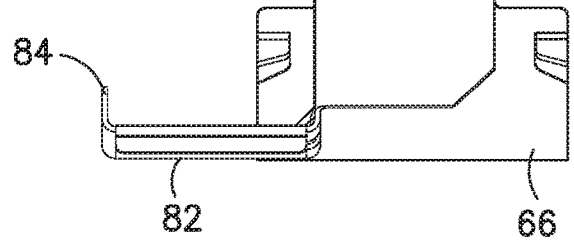
FIG. 44 illustrates a rear elevation view of the V-shaped metal clip of the catheter assembly.
Figure 45:
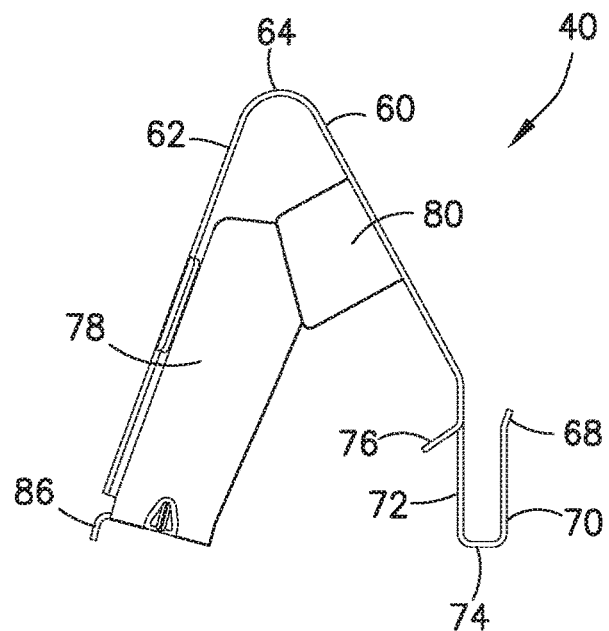
FIG. 45 illustrates a left side elevation view of the V-shaped metal clip of the catheter assembly.
Figure 46:
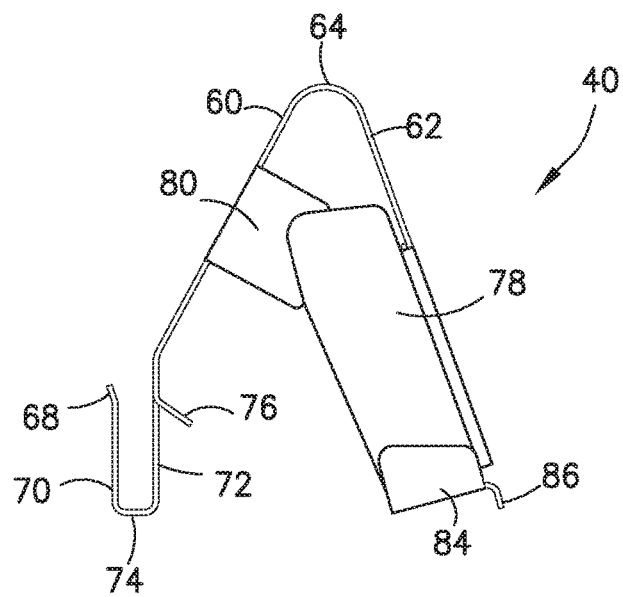
FIG. 46 illustrates a right side elevation view of the V-shaped metal clip of the catheter assembly.
Figure 47:
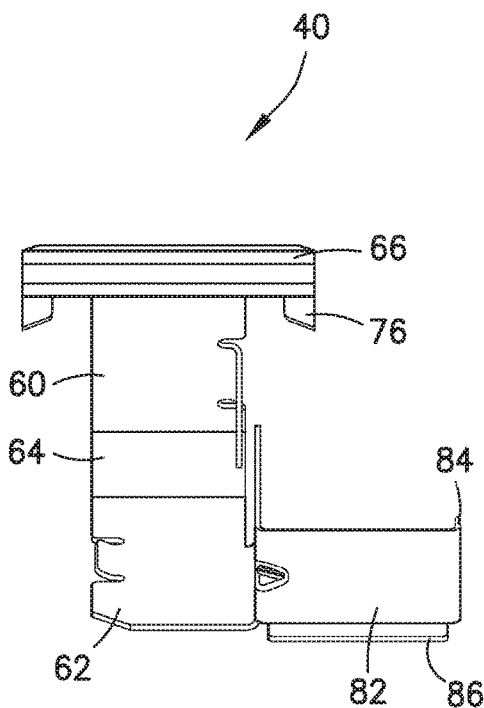
FIG. 47 illustrates a top plan view of the V-shaped metal clip of the catheter assembly.
Figure 48:
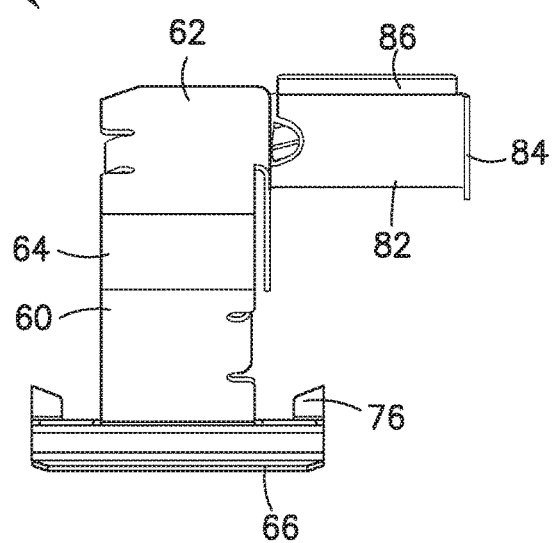
FIG. 48 illustrates a bottom plan view of the V-shaped metal clip of the catheter assembly.
Figure 50:
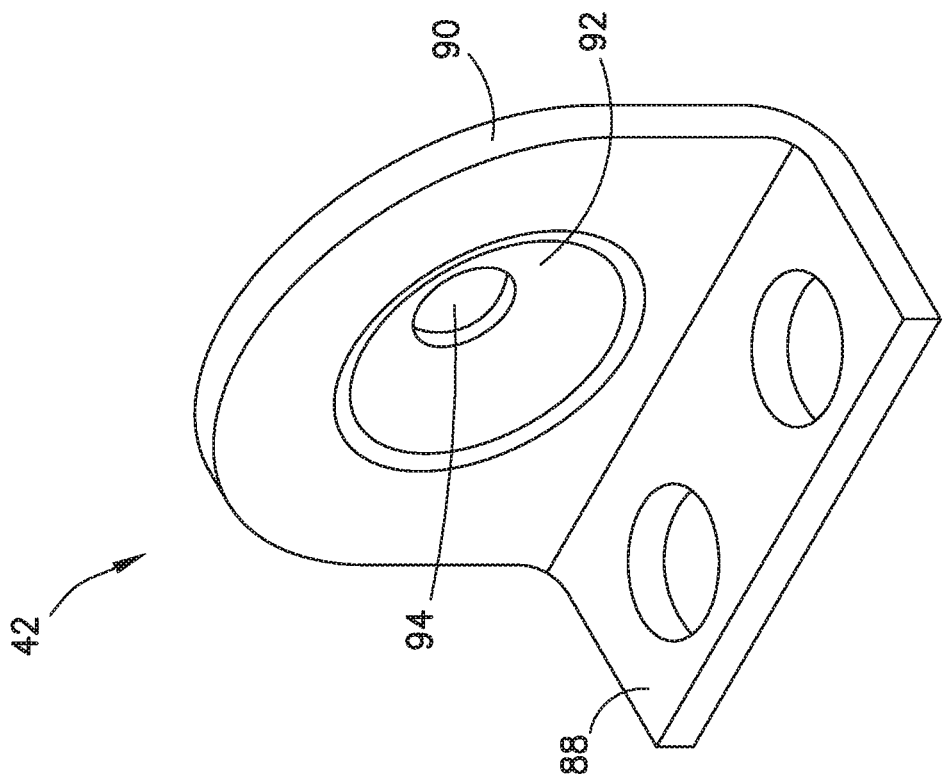
FIG. 50 illustrates a left perspective view of the washer of the catheter assembly.
Figure 49:
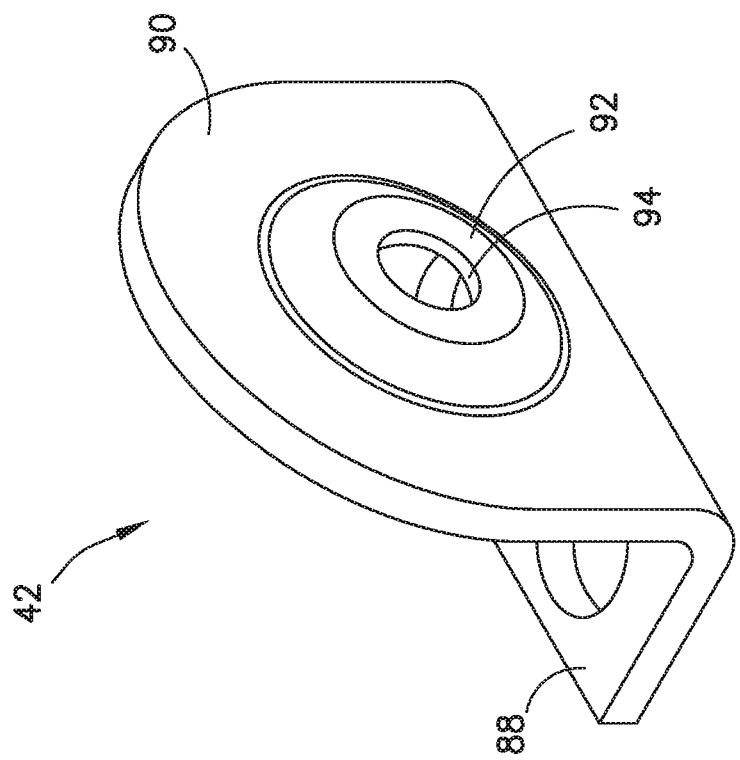
FIG. 49 illustrates a right perspective view of the washer of the catheter assembly.
Figure 51:
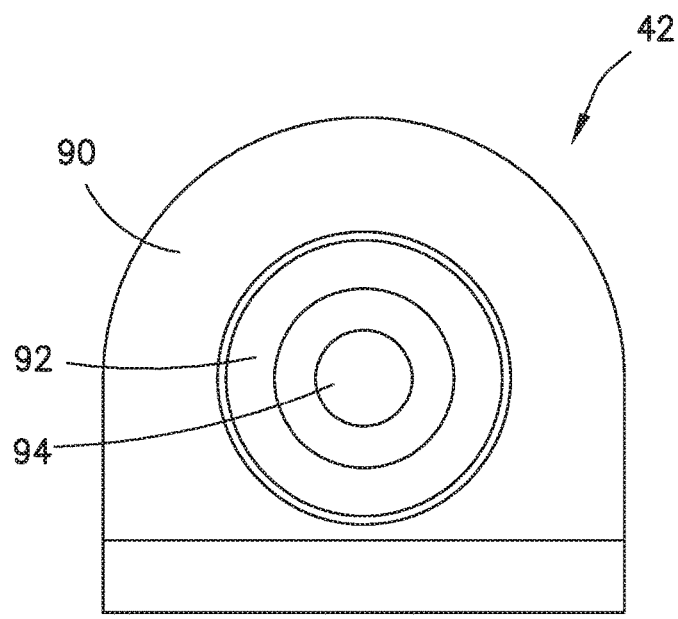
FIG. 51 illustrates a front elevation view of the washer of the catheter assembly.
Figure 52:
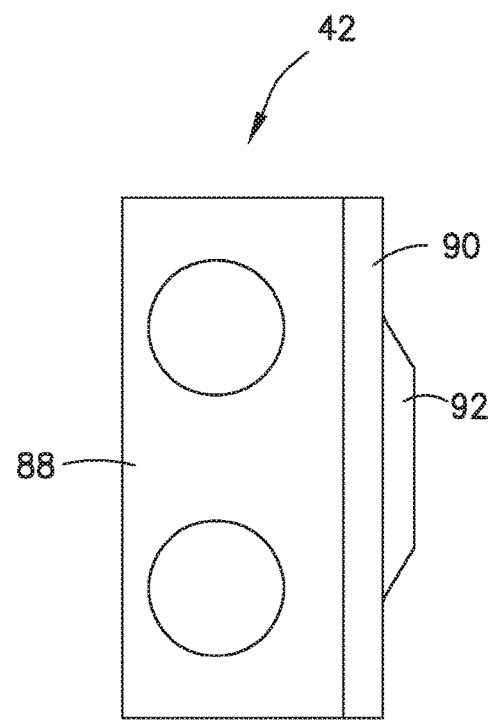
FIG. 52 illustrates a bottom plan view of the washer of the catheter assembly.
Figure 53:
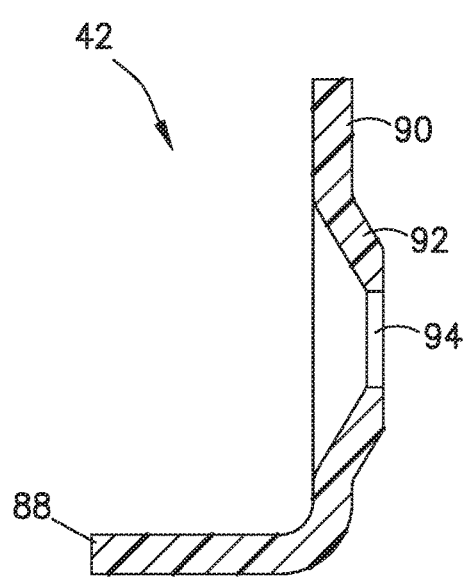
FIG. 53 illustrates a cross sectional view of a left side elevation view of the washer of the catheter assembly.
Figure 54:
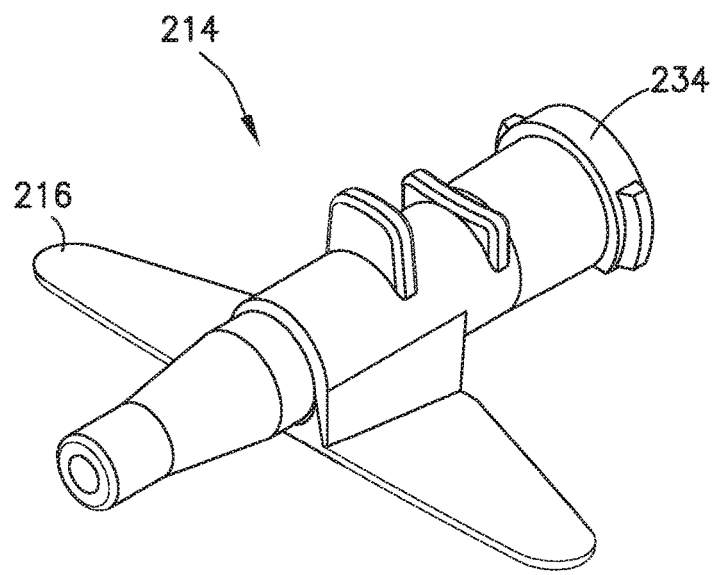
FIG. 54 illustrates a right perspective view of an alternative catheter hub with wings.
Figure 55:
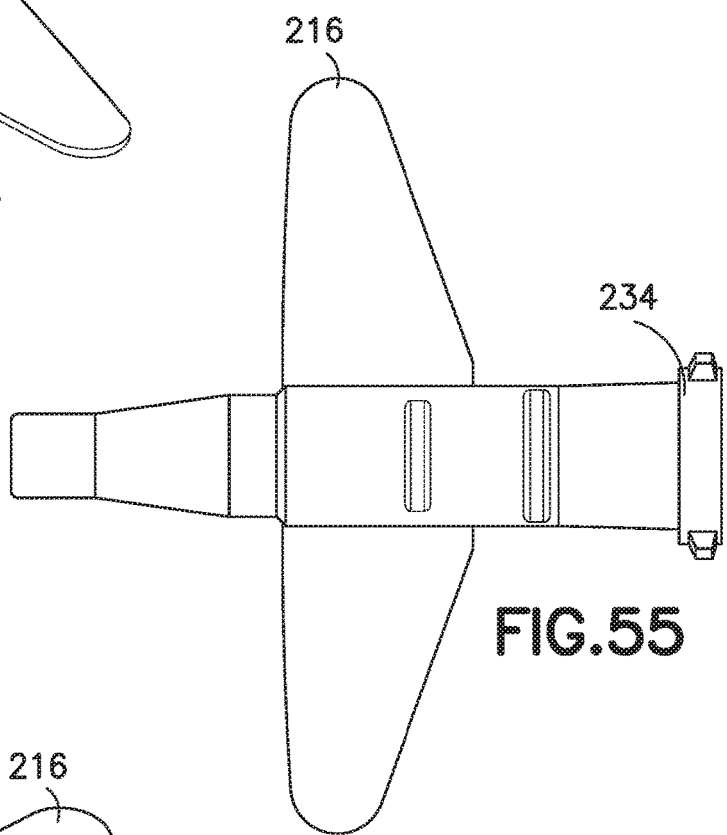
FIG. 55 illustrates a top plan view of the catheter hub with wings.
Figure 56:
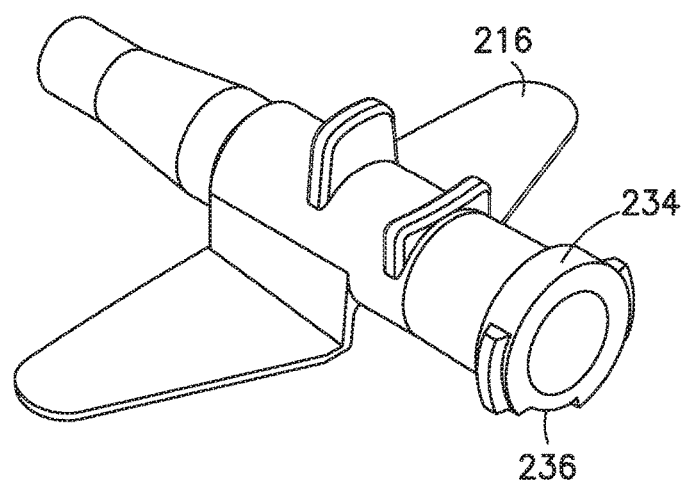
FIG. 56 illustrates a left perspective view of the catheter hub with wings.
Figure 57:
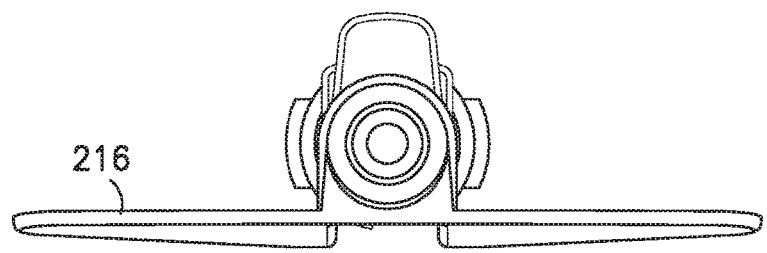
FIG. 57 illustrates a front view of the catheter hub with wings.
Figure 58:
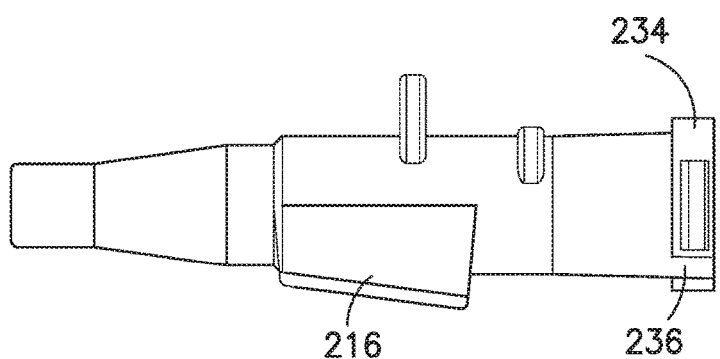
FIG. 58 illustrates a left side elevation view of the catheter hub with wings.
Figure 59:
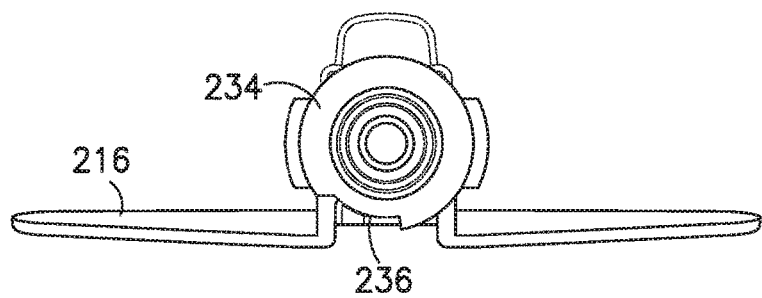
FIG. 59 illustrates a rear elevation view of the catheter hub with wings.
Figure 60:
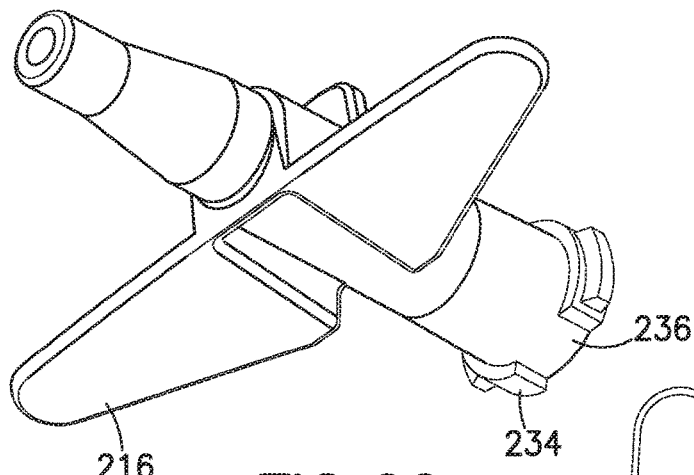
FIG. 60 illustrates a left perspective view of the catheter hub with wings.
Figure 61:
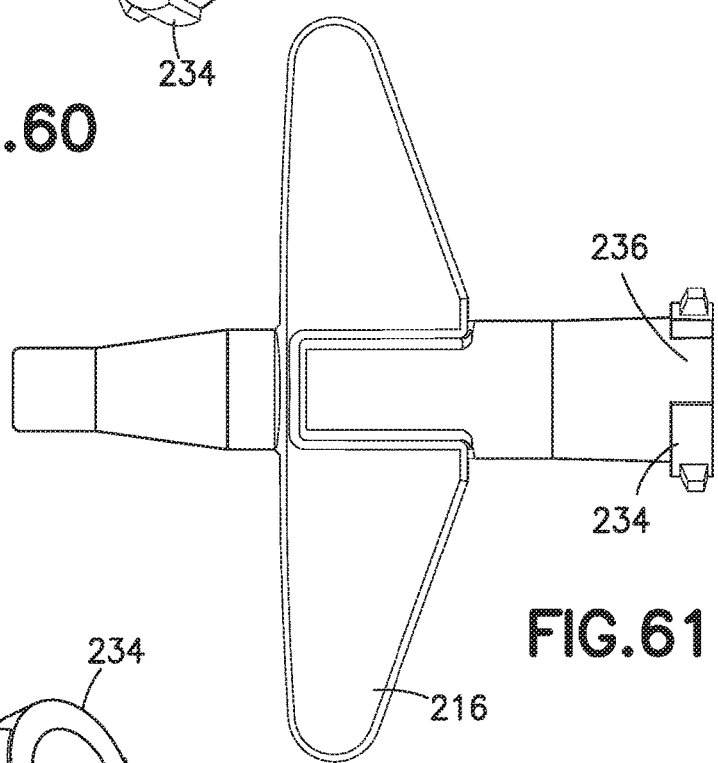
FIG. 61 illustrates a bottom plan view of the catheter hub with wings.
Figure 62:
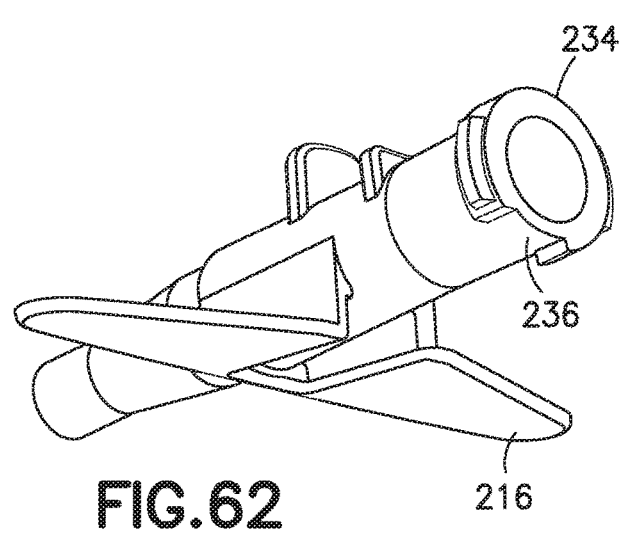
FIG. 62 illustrates a second right perspective view of the catheter hub with wings.
Figure 63:
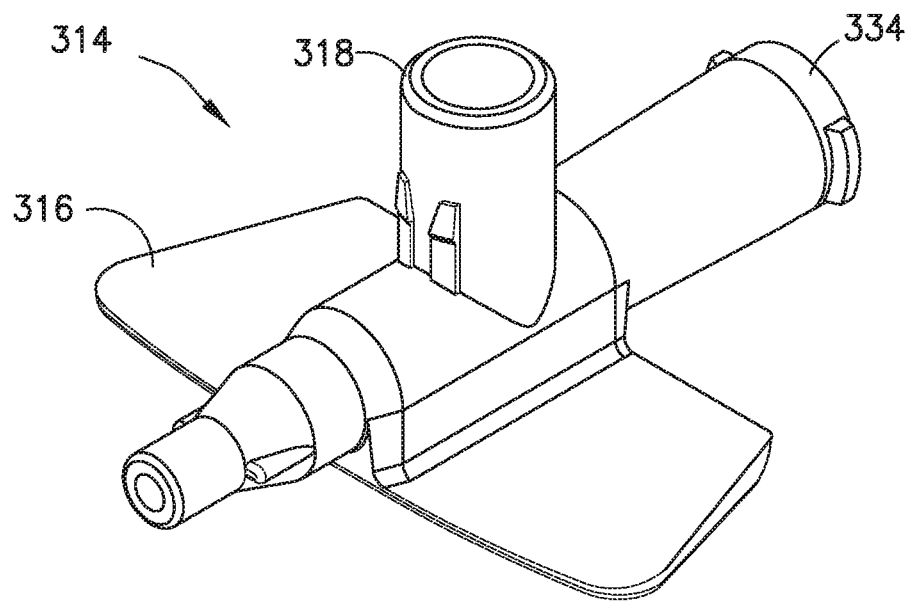
FIG. 63 illustrates a right perspective view of an alternative side port catheter hub.
Figure 64:
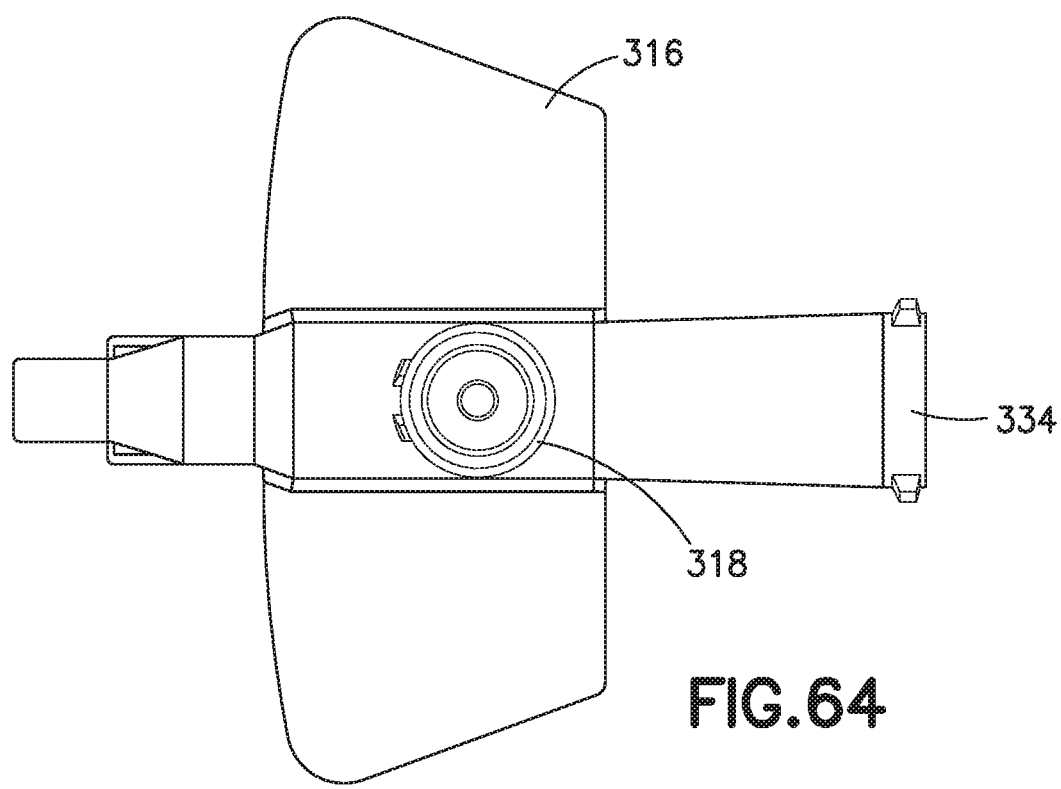
FIG. 64 illustrates a top plan view of the side port catheter hub.
Figure 65:
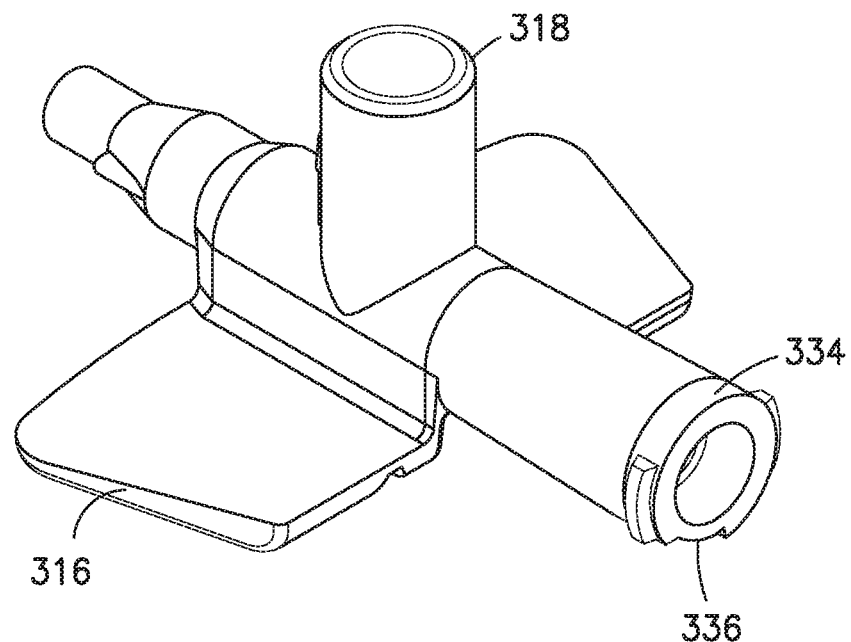
FIG. 65 illustrates a left perspective view of the side port catheter hub.
Figure 66:
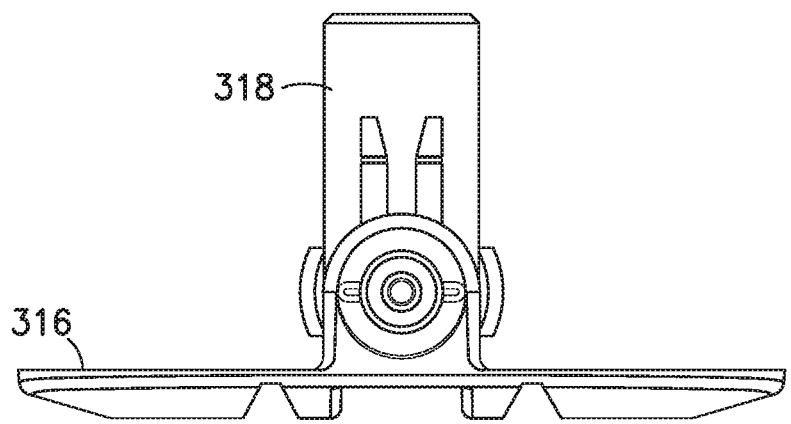
FIG. 66 illustrates a front elevation view of the side port catheter hub.
Figure 67:
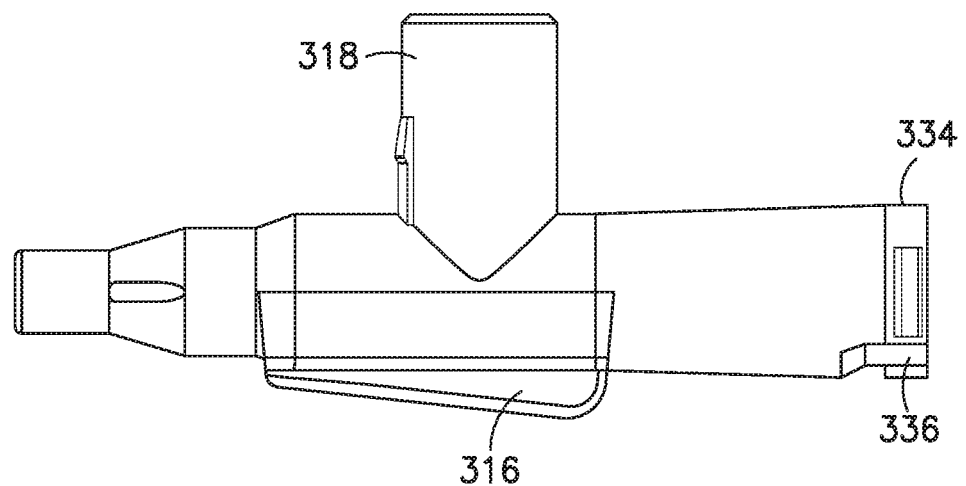
FIG. 67 illustrates a right side elevation view of the side port catheter hub.
Figure 68:
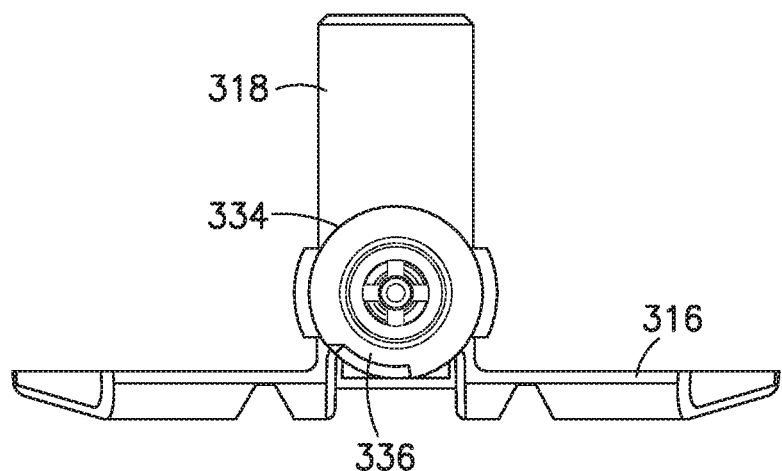
FIG. 68 illustrates a rear elevation view of the side port catheter hub.
Figure 69:
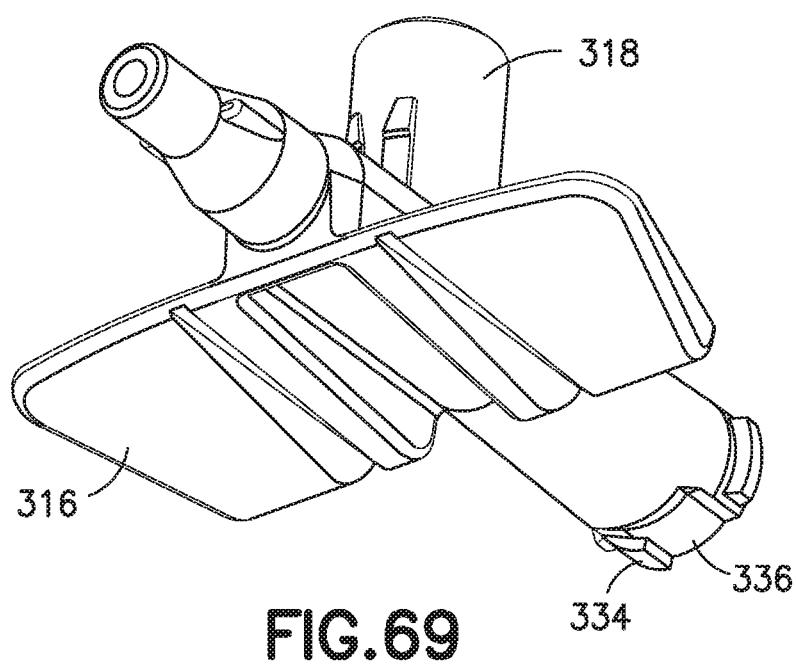
FIG. 69 illustrates a second left perspective view of the side port catheter hub.
Figure 70:
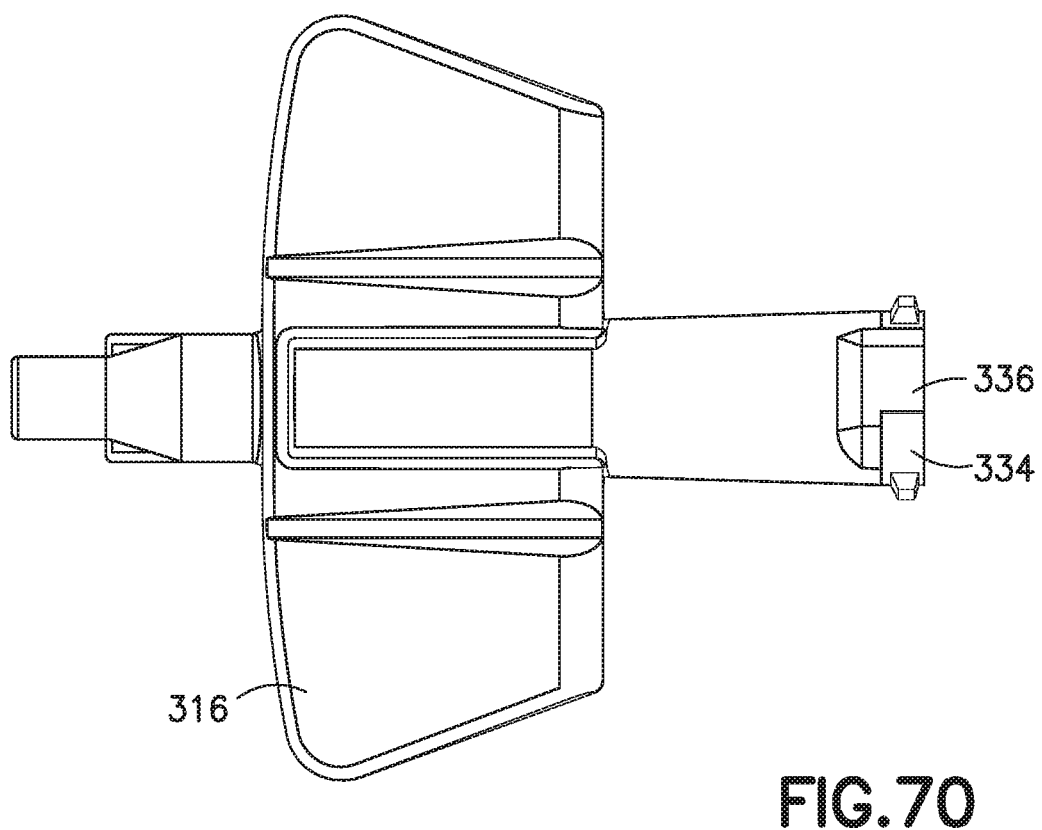
FIG. 70 illustrates a bottom plan view of the side port catheter hub.
Figure 71:
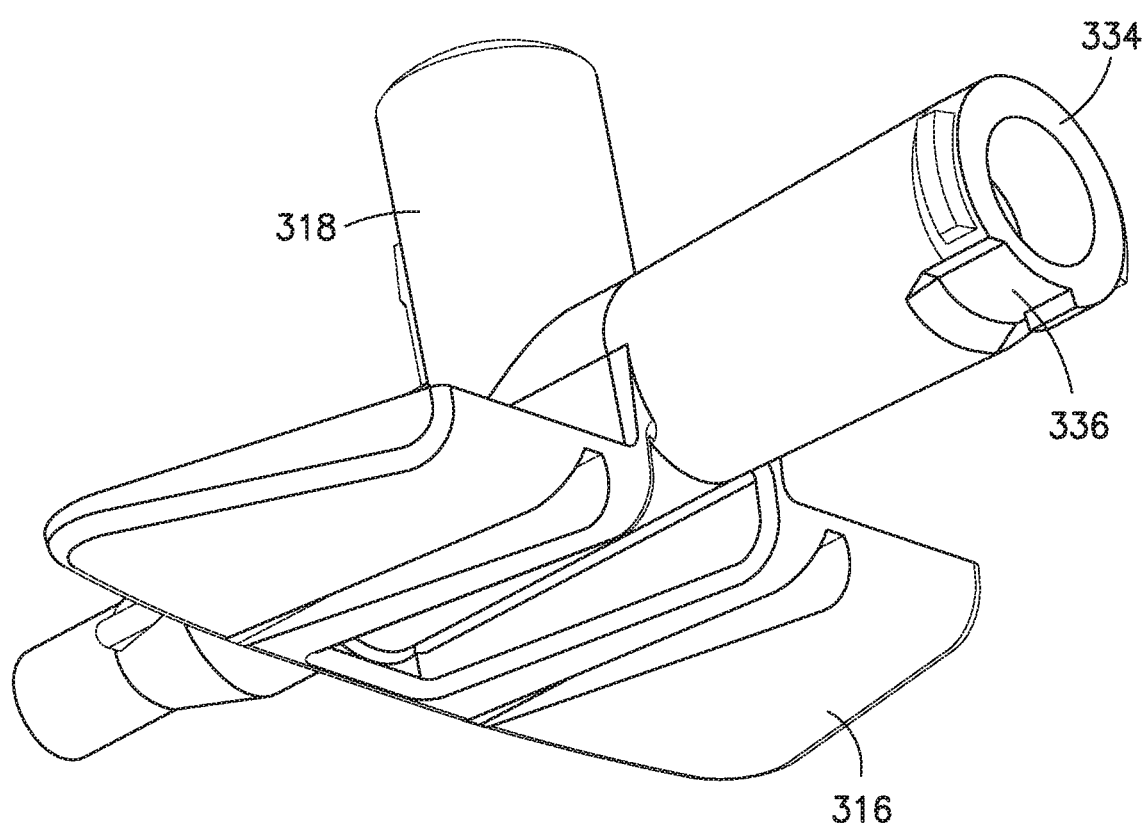
FIG. 71 illustrates a second right perspective view of the side port catheter hub.
Figure 72:
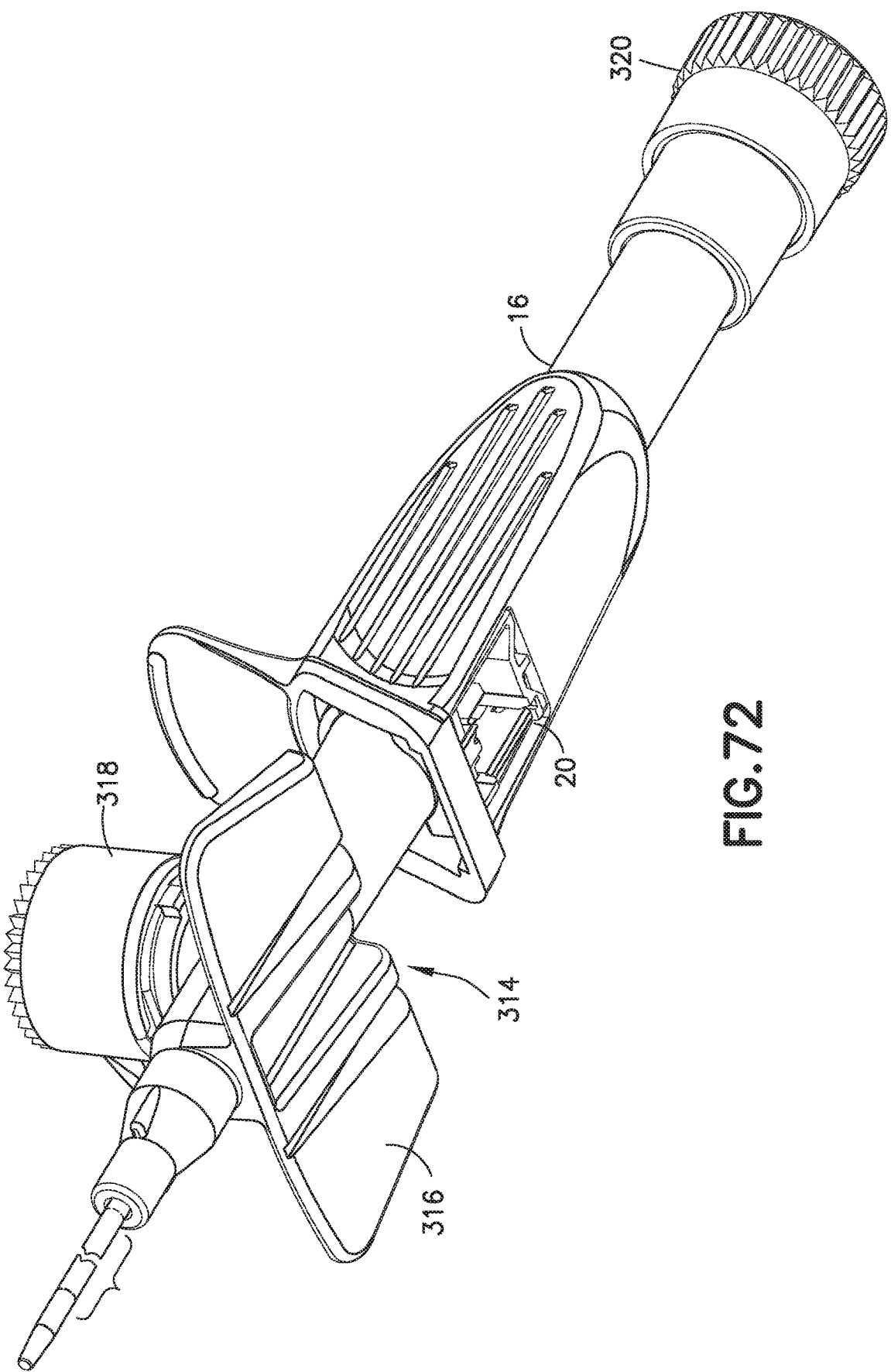
FIG. 72 illustrates a left perspective view of the alternative side port catheter hub assembly with a needle shield and needle hub.
Figure 73:
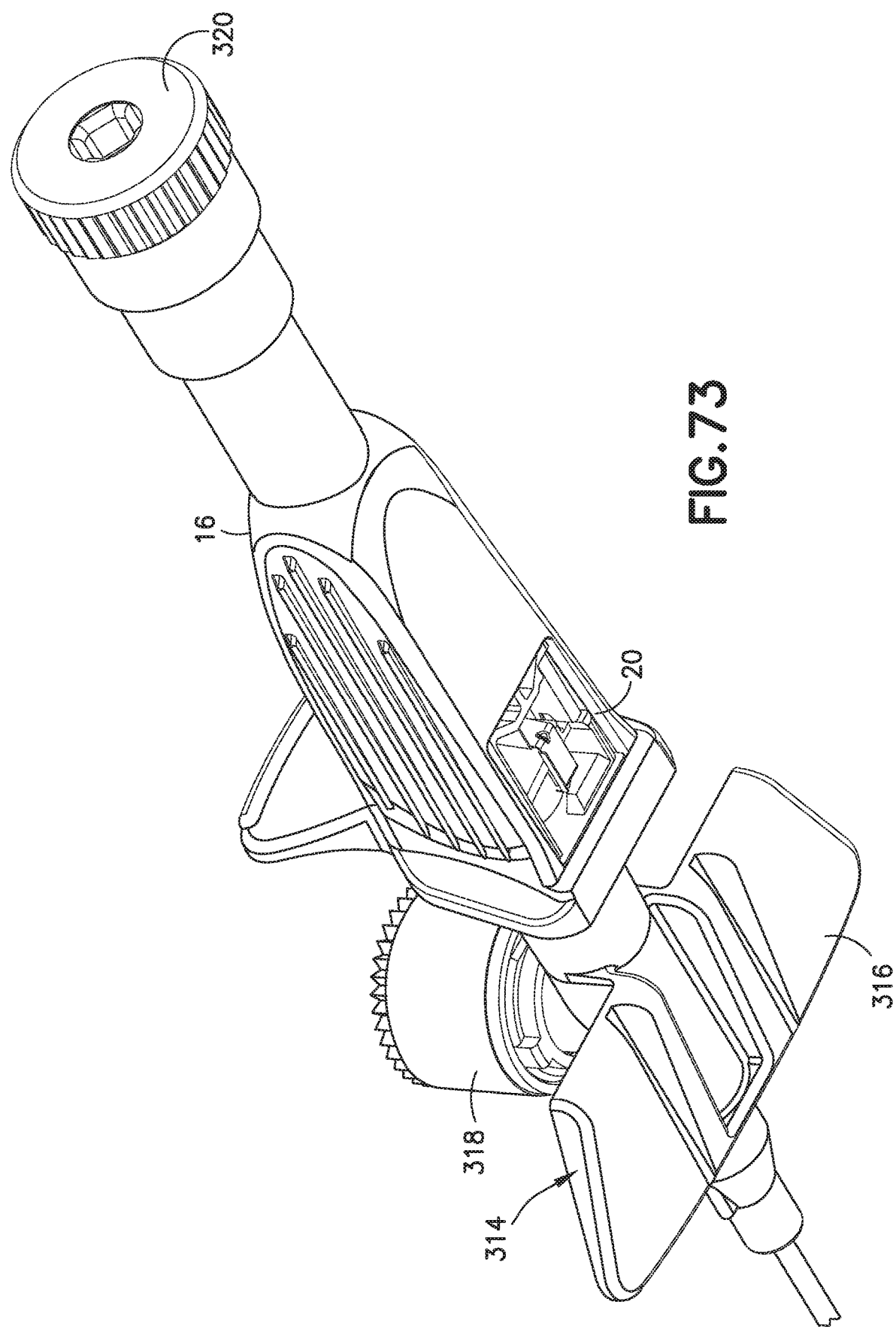
FIG. 73 illustrates a right perspective view of the alternative side port catheter hub assembly with a needle shield and needle hub.
Figure 74:
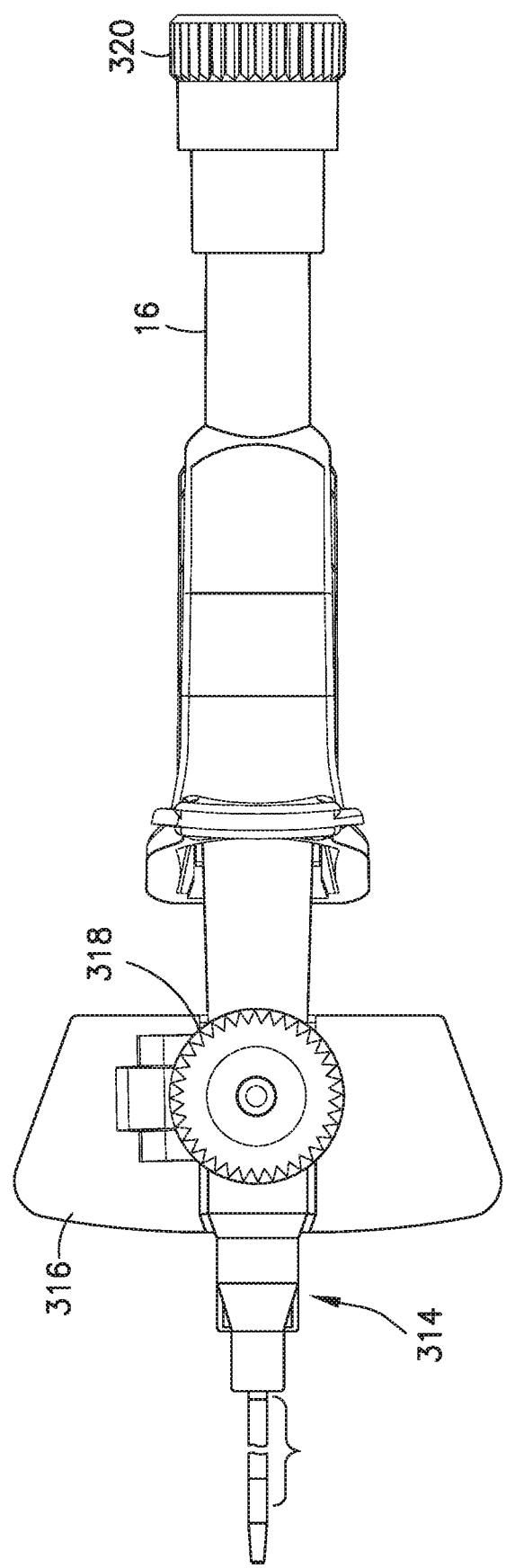
FIG. 74 illustrates a top plan view of the alternative side port catheter hub assembly with a needle shield and needle hub.
Figure 79:
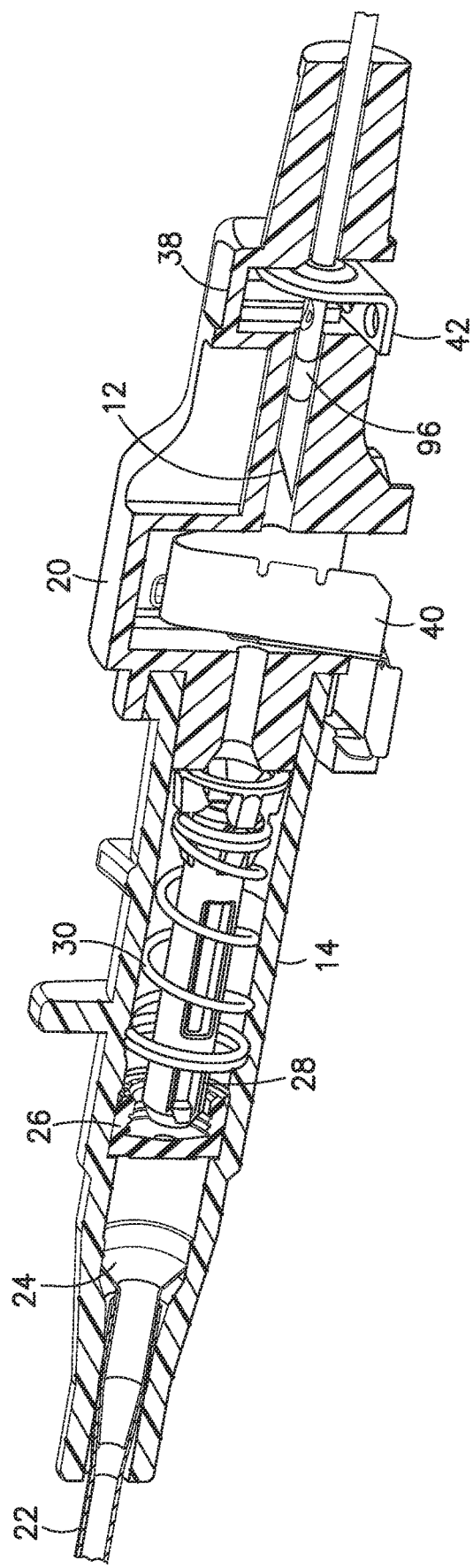
FIG. 79 illustrates a cross sectional view of the catheter assembly of FIGS. 1-16 as the introducer needle is moved past the V-shaped metal clip and the needle shield is separated from the catheter hub.

The catheter assembly disclosed herein is an improvement over that disclosed in commonly owned U.S. Patent Application Publication No. 2014/0364809, which is incorporated herein by reference.

FIGS. 1-12 illustrate a catheter assembly 10 includes a hollow metal introducer needle 12, a catheter hub 14, a needle hub 16, and a needle shield 20. The needle 12 has a sharpened and beveled distal end and initially extends through the needle shield 20 and the catheter hub 14. A flexible catheter tube 22 extends from the distal end of the catheter hub 14, with the introducer needle 12 passing through the catheter tube 22. Initially, the needle 12 is inserted into a patient's vein. The catheter tube 22 is carried by the needle 12 into the vein. After the catheter tube 22 is inserted, the needle 12 is removed from the patient's vein and the catheter hub 14. The needle shield 20 encloses the tip of the needle 12 and provides protection from being stuck by the needle 12 during and after the needle's retraction from the catheter hub 14. The needle shield 20 can be used with a variety of different catheters.

As illustrated in FIGS. 12-20, the catheter assembly includes the catheter hub 14 and the flexible catheter tube 22 extending from the catheter hub 14. A metal wedge 24 is positioned in the catheter hub 14 to retain the catheter tube 22. A resilient septum 26 is positioned to control fluid flow through the catheter hub 14. An actuator 28 is moveably positioned in the catheter hub 14 to engage the septum 26. A biasing member 30 engages the actuator 28 to bias the actuator 28 in the proximal direction.

The resilient septum 26 has one or more pre-formed slits which are normally closed to selectively prevent unwanted fluid flow through the septum 26. For example, the septum 26 can have three slits forming three triangular flaps that open when engaged by the actuator 28. The septum 26 is made from an elastic material, for example silicone rubber, that provides the resilient closing force for the slits. Other septum 26 configurations may be used as would be understood by one of ordinary skill in the art.

The actuator 28 and the biasing member 30, for example a metal or plastic compression spring, are positioned in the catheter hub 14. The actuator 28 engages the septum 26 to open the slits and permit fluid flow through the catheter hub 14. The biasing member 30 is capable of returning the actuator 28 to a position that allows the slits to close, preventing fluid flow through the catheter hub 14.

As best shown in the exemplary embodiment of FIGS. 21-29, the catheter hub 14 includes a proximal end having external Luer thread 32 and a notched collar 34. The collar 34 extends around at least a portion of the catheter hub 14 and is preferably disposed at a proximal end of the catheter hub 14. The collar 34 has a break, opening or notch 36 separating first and second ends of the collar 34.

A portion of the collar 34 includes an outer diameter that is greater than a portion of an outer diameter of the catheter hub 14 adjacent to the collar 34. Specifically, a portion of the outer diameter of the collar 34 is elevated with respect to the adjacent outer diameter surface of the catheter hub 14. Additionally, the opening 36 of the collar 34 has an outer diameter substantially equal to or greater than a portion of an outer diameter of the catheter hub 14 adjacent to the collar 34.

In an exemplary embodiment, the needle shield 20 includes an outer housing 38, a resilient clip 40, and a washer 42. The outer housing 38 includes an aperture having a distal opening 44 and a proximal opening 46 to receive the needle 12. The outer housing 38 connects to the catheter hub 14 and surrounds the clip 40 and the washer 42. As best shown in FIGS. 30-39, the distal end of the outer housing 38 includes a nose 48, a top flange 50, and a base 52. When the needle shield 20 is connected to the catheter hub 14, the nose 48 extends into the interior of the catheter hub 14.

In an exemplary embodiment, the nose 48 is sized to be slightly smaller than the interior of the catheter hub 14 so as to fit with a loose tolerance. The top flange 50 is spaced from the base 52 by a pair of side recesses that receive the Luer threads 32 and prevent rotation of the catheter hub 14 with respect to the needle shield 20 when assembled. The base 52 includes a projection 54 having a curved top surface and curved cut-out portion 56. The projection 54 is sized to fit in the opening 3601 the collar 34 and the cut-out portion 56 is sized to allow the collar 34 to pass therethrough.

According to an exemplary embodiment illustrated in FIGS. 40-48, the clip 40 is a substantially V-shaped resilient clip 40 having a first leg 60 and a second leg 62 connected by an angled or curved V section 64. The first leg 60 includes a substantially U-shaped spade 66 having an angled lead-in portion 68. The spade 66 includes an outer wall 70 and an inner wall 72 connected by a bottom 74. A pair of barbs 76 extends outwardly from the inner wall 72 of the spade 66. A first flag 78 extends from the second leg 62 toward the first leg 60 and a second flag 80 extends from the first leg 60 toward the second leg 62. A foot 82 extends outwardly from the first flag 78 away from the first and second legs 60, 62, and a latch 84 extends upwardly from the foot 84 and is positioned between the first and second legs 60, 62. Specifically, the latch 84 is disposed between a plane representing the first leg 60 and a plane representing the second let 62. Such a configuration is desired to create a more compact clip 40. An optional stiffener 86 can extend downwardly from the foot 82.

The clip 40 is connected to the outer housing 38 with the spade 66 being positioned around an exterior wall of the outer housing 38. The spade 66 is attached to the exterior wall of the outer housing 38 so that the outer wall 70 of the spade 66 is exposed to the outside of the needle shield 20. This configuration advantageously reduces the width of the needle shield 20, compared to an arrangement wherein the spade 66 is received within an internal cavity of the outer housing 38 such that the outer wall 70 is not exposed to the outside of the outer housing 38. As best shown in FIGS. 79-85, the inner wall 72 of the spade 66 is positioned in a recess and the two barbs 76 extend away from the inner wall 72 to engage a pair of projections 89 in the needle shield 20. The two barbs 76 aid in securely fastening the clip 40 to an inner surface of the needle shield 20. The clip 40 may be formed from a metal, elastomer, polymer, or composite material. In various exemplary embodiments, the clip 40 is formed from a thin piece of resilient metal, such as stainless steel.

According to an exemplary embodiment illustrated in FIGS. 49-53, the washer 42 includes a base 88 and a side wall 90 connected together in a substantially L-shape. The side wall 90 includes a funnel 92 and an opening 94. The needle 12 includes a deformation 96, for example a crimp or protrusion formed near the distal end of the needle 12. The opening 94 in the washer 42 is sized to allow passage of the needle shaft, but not the deformation 96. The funnel 92 makes it easier for the proximal end of the needle 12 to be initially inserted through the washer 42 during assembly.

FIGS. 54-62 depict an alternative exemplary catheter hub 214 having a pair of stabilization wings 216. FIGS. 63-76 depict another alternative exemplary side port catheter hub 314 having a pair of stabilization wings 316 and a side port 318. The side port communicates with an internal tubular valve (not shown) as described in U.S. Pat. No. 4,231,367, which is incorporated herein by reference. The alternative catheter hubs 214, 314 each have a collar 234, 334 with an opening 236, 336 to receive the latch 84 of the needle shield 20.

The catheter assemblies can include a plug 320 that is initially attached to the needle hub 16. After the needle hub 16 and needle shield 20 have been removed from the catheter hub, the plug 320 can be removed from the needle hub 16 and attached to the open, proximal end of the catheter hub. Although depicted with only the side port catheter 314, the plug 320 can be used with any of the catheter hubs 14, 214, 314.

Figure 80:
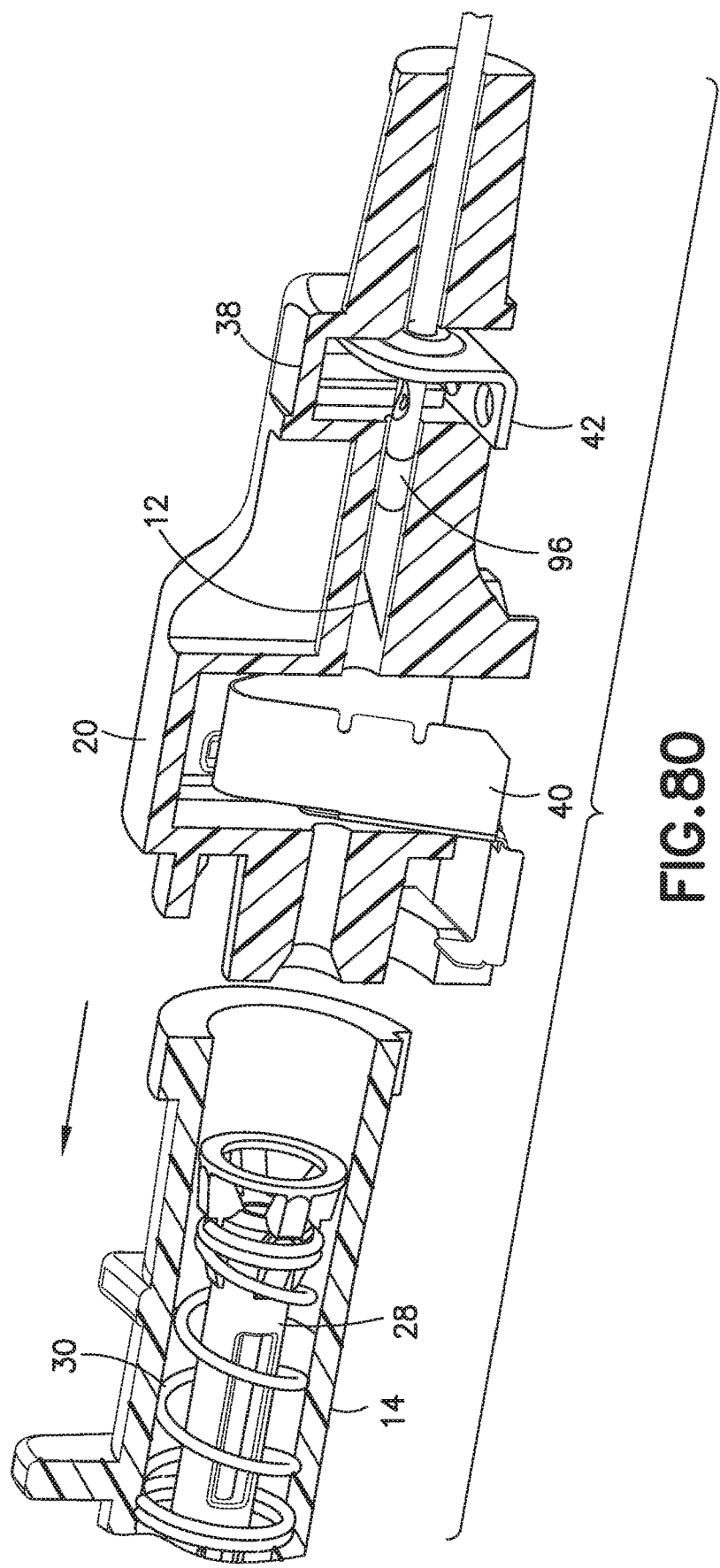
FIG. 80 illustrates a second cross sectional view of the catheter assembly of FIGS. 1-16 as the introducer needle is moved past the V-shaped metal clip and the needle shield is separated from the catheter hub.
Figure 81:
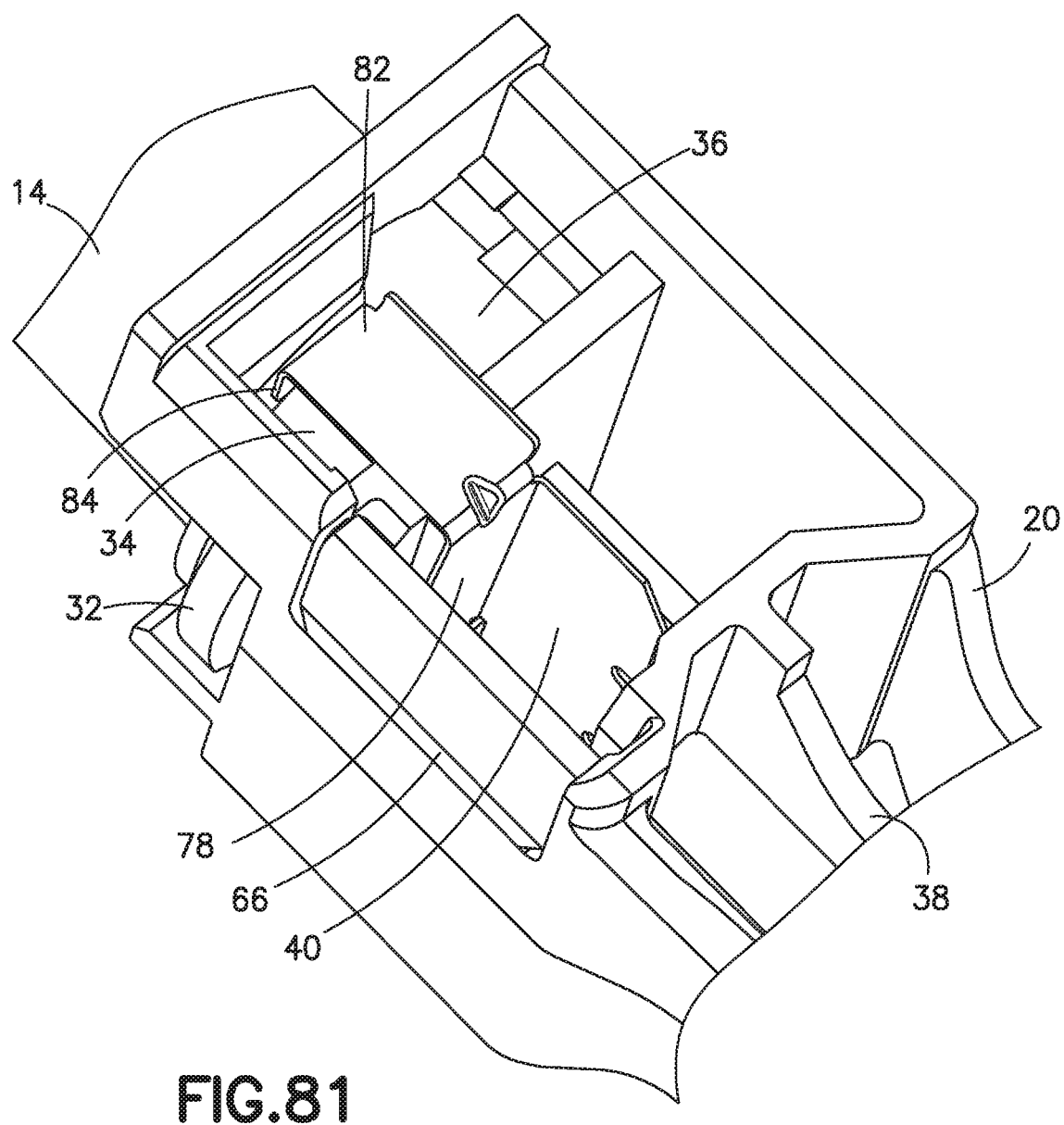
FIG. 81 illustrates a latch of the V-shaped metal clip engaged with the catheter hub.
Figure 82:
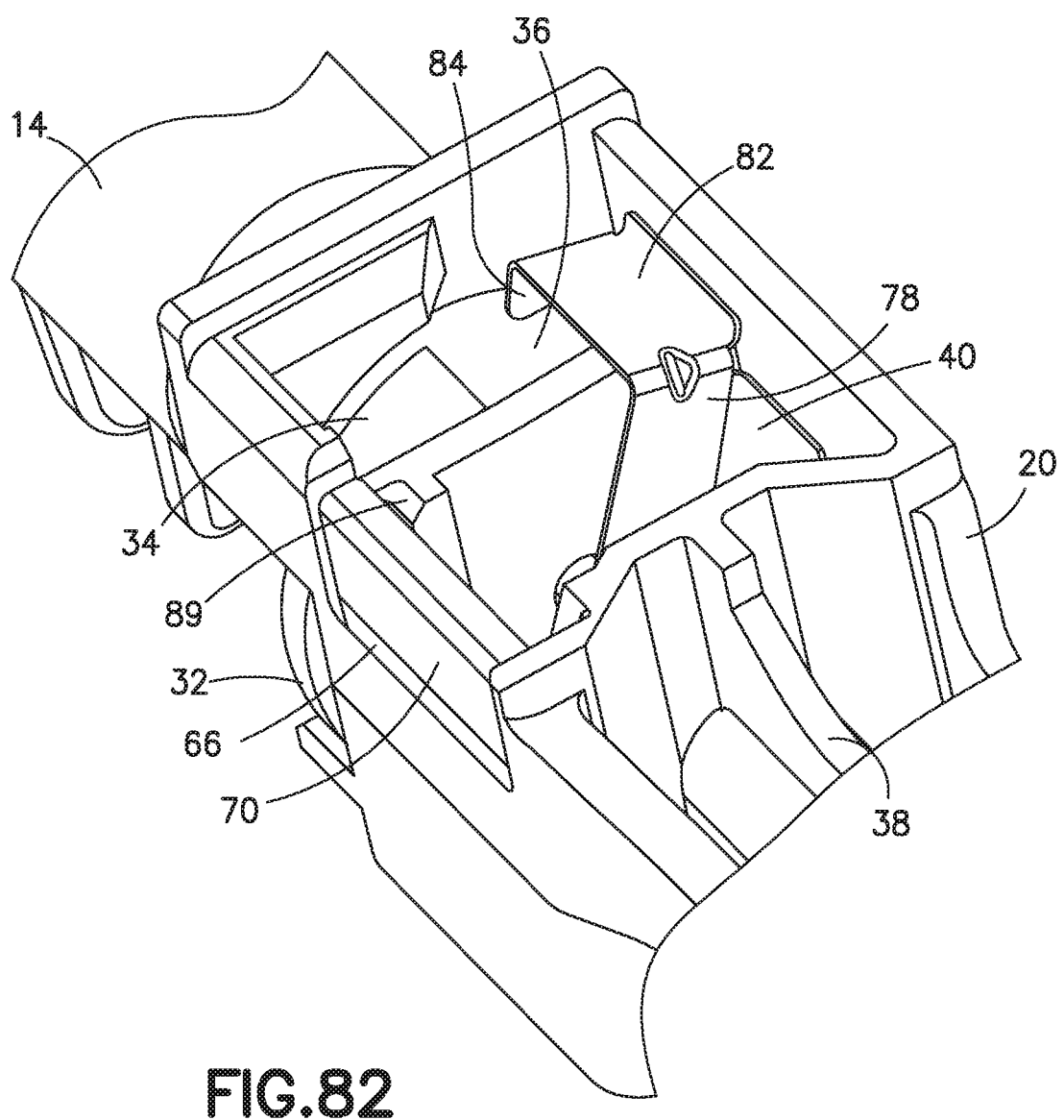
FIG. 82 illustrates the latch of the V-shaped metal clip disengaged from the catheter hub.
Figure 83:
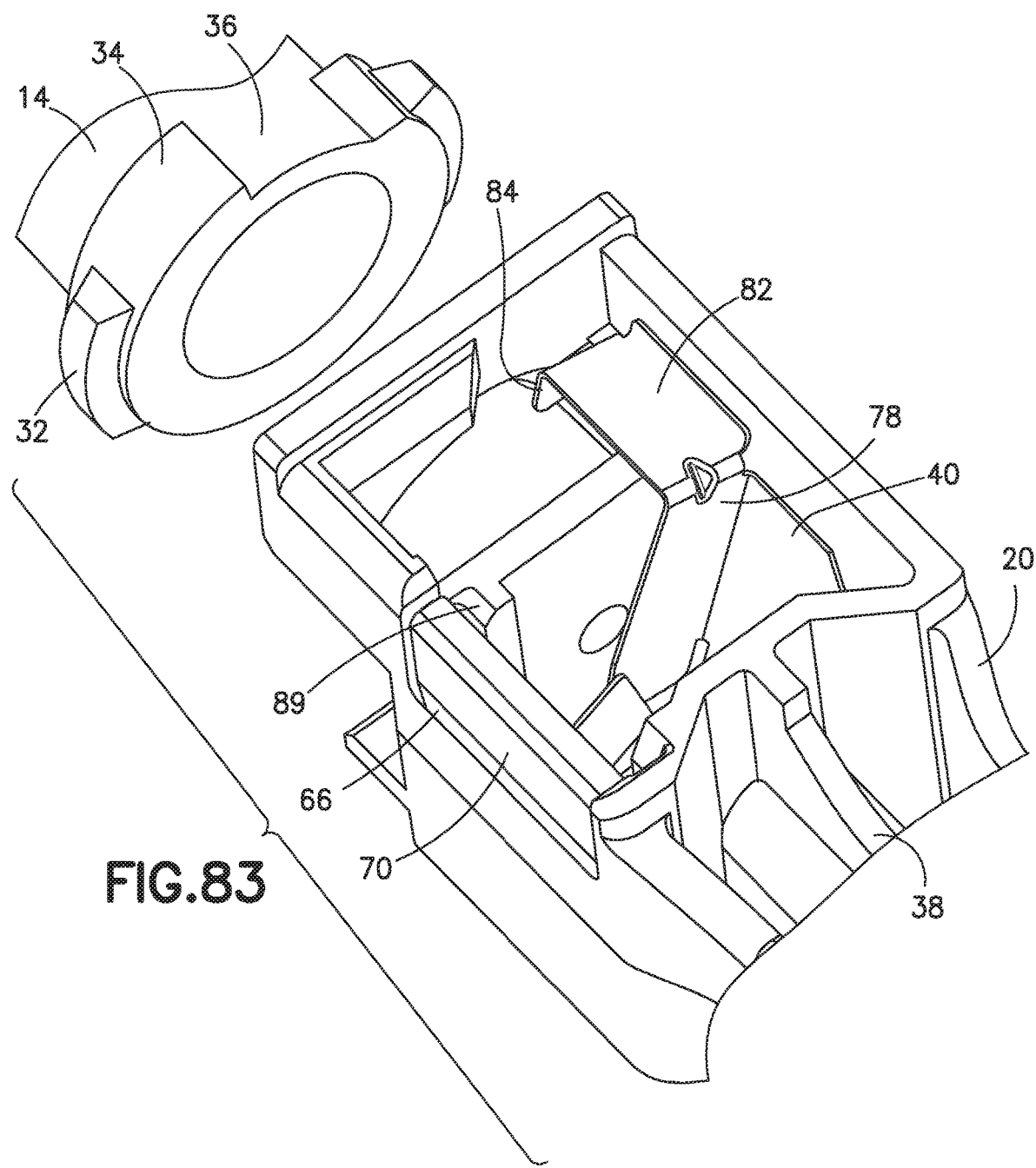
FIG. 83 illustrates the latch of the V-shaped metal clip disengaged from the catheter hub and separated.
Figure 84:
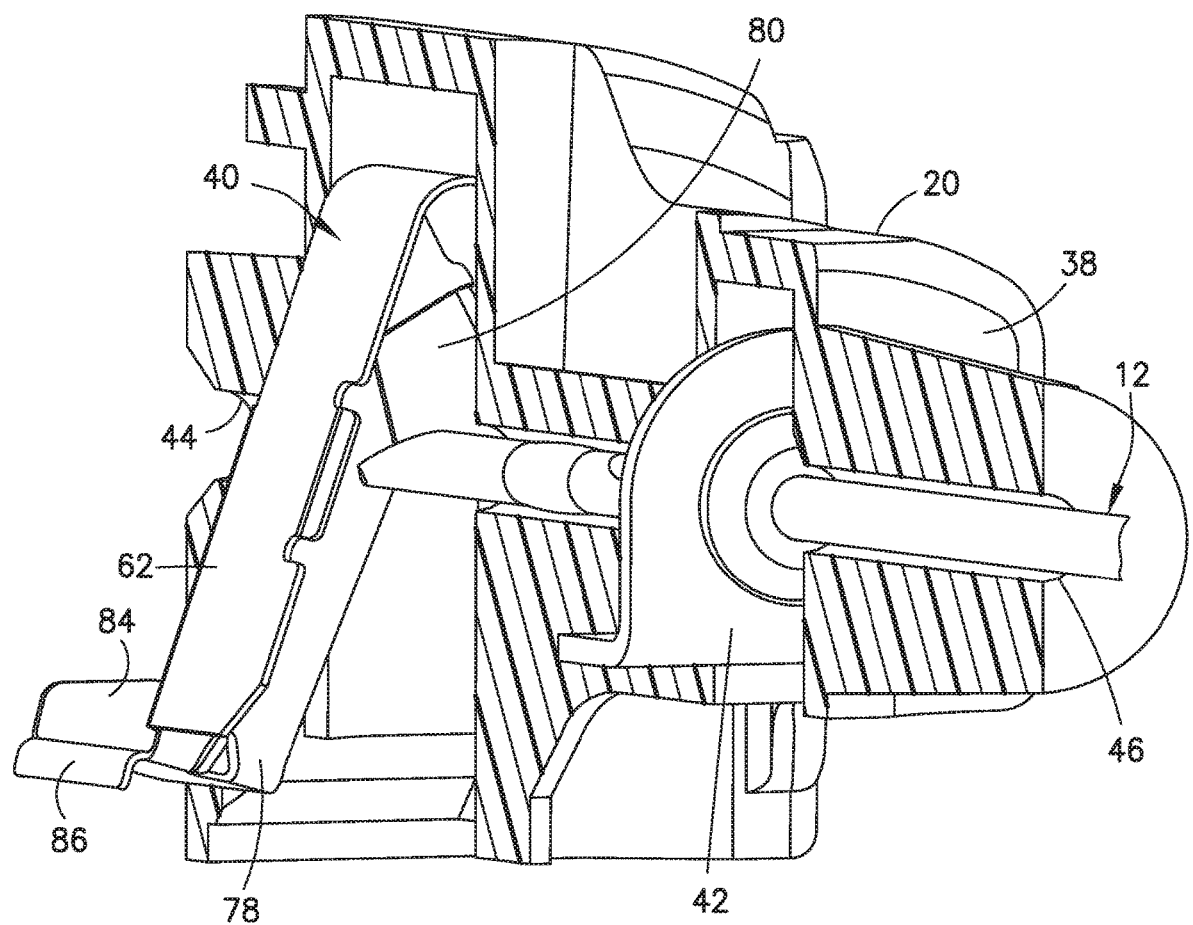
FIG. 84 illustrates a view of the V-shaped metal clip blocking the needle.
Figure 85:
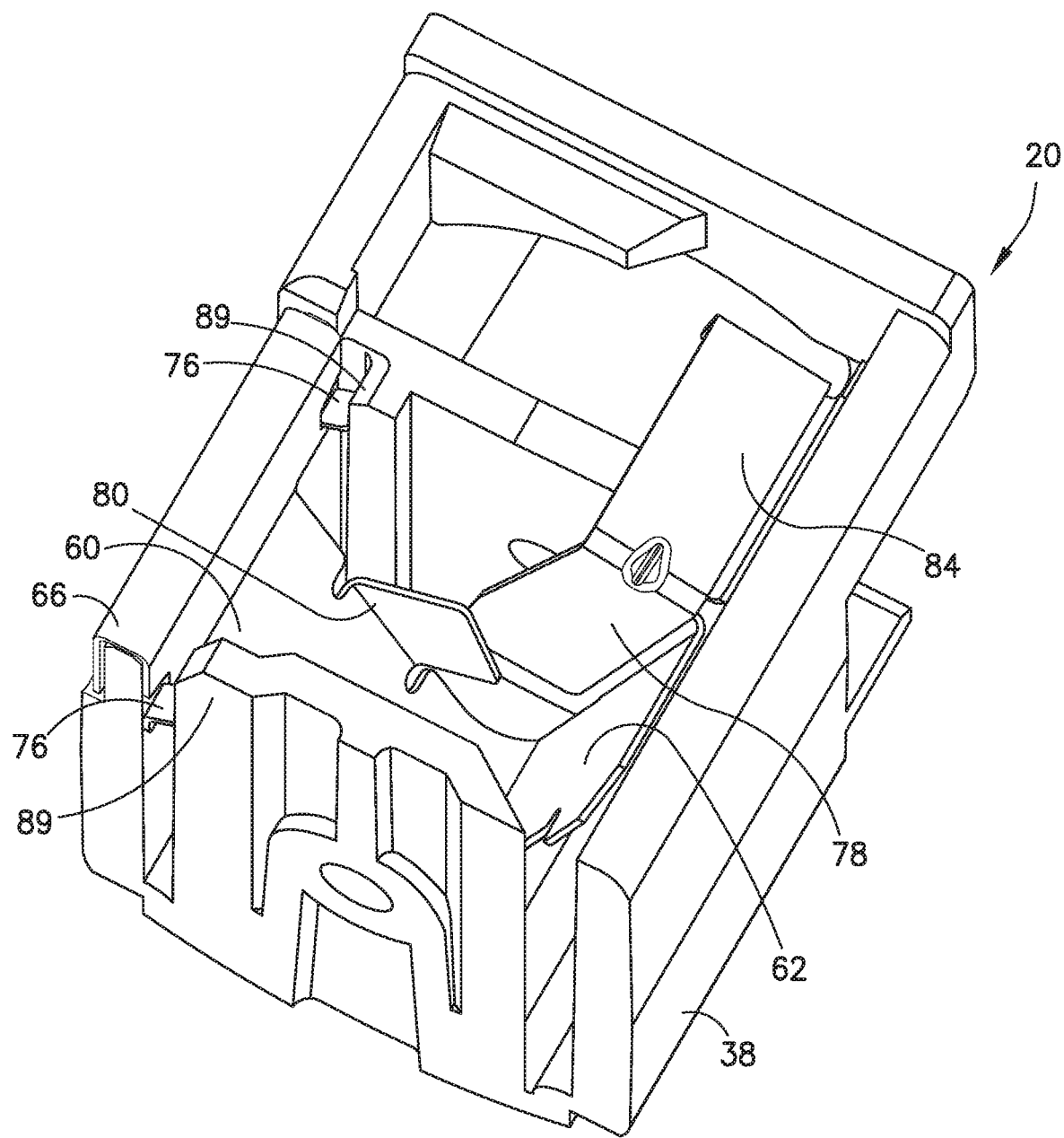
FIG. 85 illustrates a view of the V-shaped metal clip in the closed position.
Figure 86:
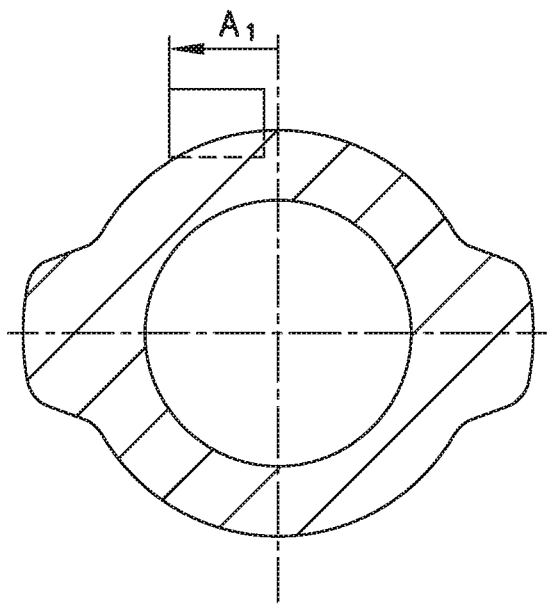
FIG. 86 illustrates a schematic view of the working envelope of the V-shaped metal clip and catheter hub collar without a notch.
Figure 87:
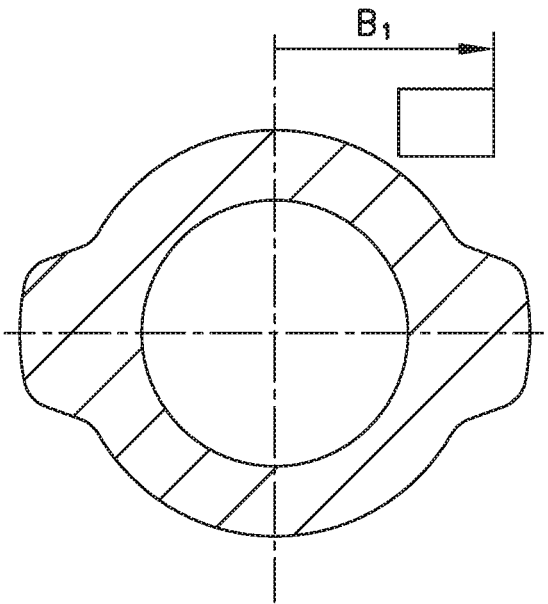
FIG. 87 illustrates a schematic view of the working envelope of the V-shaped metal clip and catheter hub collar without the notch.
Figure 88:
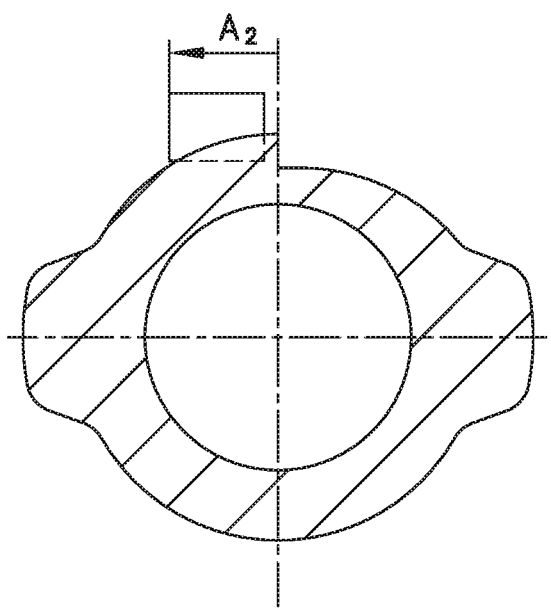
FIG. 88 illustrates a schematic view of the working envelope of the V-shaped metal clip and notched catheter hub collar.
Figure 89:
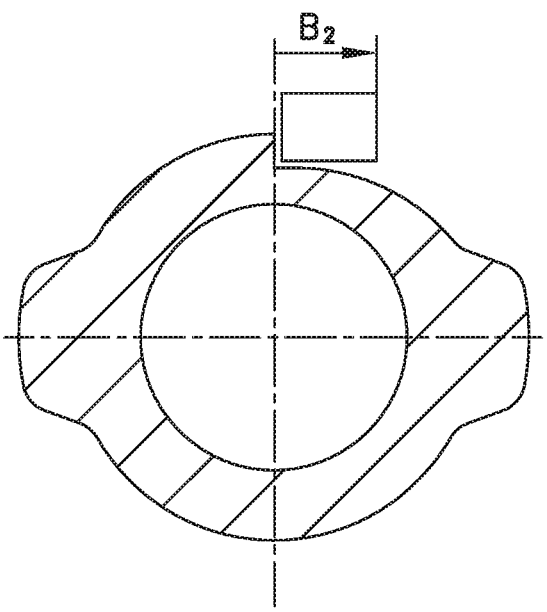
FIG. 89 illustrates a schematic view of the working envelope of the V-shaped metal clip and notched catheter hub collar.

FIGS. 77-85 depict the catheter assembly 10 of FIGS. 1-12 during operation. Initially, the needle shield 20 is connected to the catheter hub 14 and the introducer needle 12 passes through the catheter hub 14 and the needle shield 20. The nose 48 of the needle shield 20 (labeled in FIG. 30) may or may not extend into the catheter hub 14 when the needle 12 is in use (first position). The needle 12 cooperates with the clip 40 by biasing the clip 40 into a locked position via pressing the first and second arms 60, 62 toward one another. In the locked position, the latch 84 engages the collar 34, preventing removal of the needle shield 20 from the catheter hub 14, as best shown in FIG. 81. At the same time, in the locked position, the latch 84 is offset from the collar opening 36. The position of the latch 84 is off-center with respect to the needle 12. The clip 40 is also in an open position, allowing the needle 12 to traverse through the clip 40.

As the needle 12 is withdrawn from the catheter hub 14 and into the needle shield 20, the tip of the needle 12 clears the clip 40, and the clip 40 is allowed to resiliently expand, causing the second arm 62 to move away from the first arm 60. As the clip 40 expands laterally, the primary and secondary flags 78, 80 block the distal opening 44 of the outer housing 38 aperture, preventing the tip of the needle 12 from exiting the distal end of the outer housing 38.

Movement of the second leg 62 moves the latch 84 laterally from engagement with the collar 34 to a position aligned with the collar opening 36, allowing the needle shield 20 to be disengaged or unlocked from the catheter hub 14. The direction in which the latch 84 moves is lateral with respect to a centerline of the needle 12. The latch 84 movement is not radial toward or away from the needle 12. Moreover, as the latch 84 is adjusted, the latch 84 moves to a centered position and then ultimately moves off-center with respect to the needle 12. The off-center positions of the latch 84 in the first and second positions of the needle 12 are symmetrically opposite each other.

In the position when the flags 78, 80 block the needle 12, the clip 40 moves to a closed position. At the same time, the needle 12 enters into a second position that is retracted from the first needle position, which prevents further use of the needle 12. The first position, as described above, is understood as, for example, all positions of the needle 12 prior to entering the second position.

As the needle 12 is pulled further in the proximal direction, the shaft of the needle 12 slides through the needle shield 20 until the deformation 96 formed near the distal end of the needle 12 cooperates with and engages the washer 42, as shown in FIG. 80. The opening in the washer 42 is sized to allow passage of the needle shaft, but not the deformation 96. Thus, the washer 42 prevents the distal tip of the needle 12 and the deformation 96 from exiting the needle shield 20 when the needle 12 is in the second position. The combination of the washer 42 and the needle shield 20 enclose the distal tip of the needle 12 in this second position. Further proximal movement of the needle 12 results in the needle shield 20 being pulled away from the catheter hub 14.

The combination of the clip 40 and the washer 42 act as an exemplary needle tip protection mechanism. This needle tip protection mechanism encloses the distal needle tip and the deformation 96 and prevents these portions of the needle 12 from exiting the needle shield 20.

More information regarding needle tip protection mechanisms of the type used in this embodiment can be found in U.S. Pat. Nos. 6,749,588 and 7,604,616, and U.S. Patent Application Publication No. 2014/0364809, the contents of which are hereby incorporated by reference. The features described in this embodiment, including the needle protection features, can be used in combination with the features described throughout this application.

As depicted in FIGS. 86-89, the use of the clip 40 and the notched collar 34 allows for a smaller, more compact design. Without the collar opening 36, the latch 84 would have to move a distance B1 to clear the collar and allow disengagement of the needle shield 20. With the collar opening 36, the latch 84 does not have to clear the entire catheter hub 14 and only needs to move a distance B2 which is less than B1.

Figure 90:
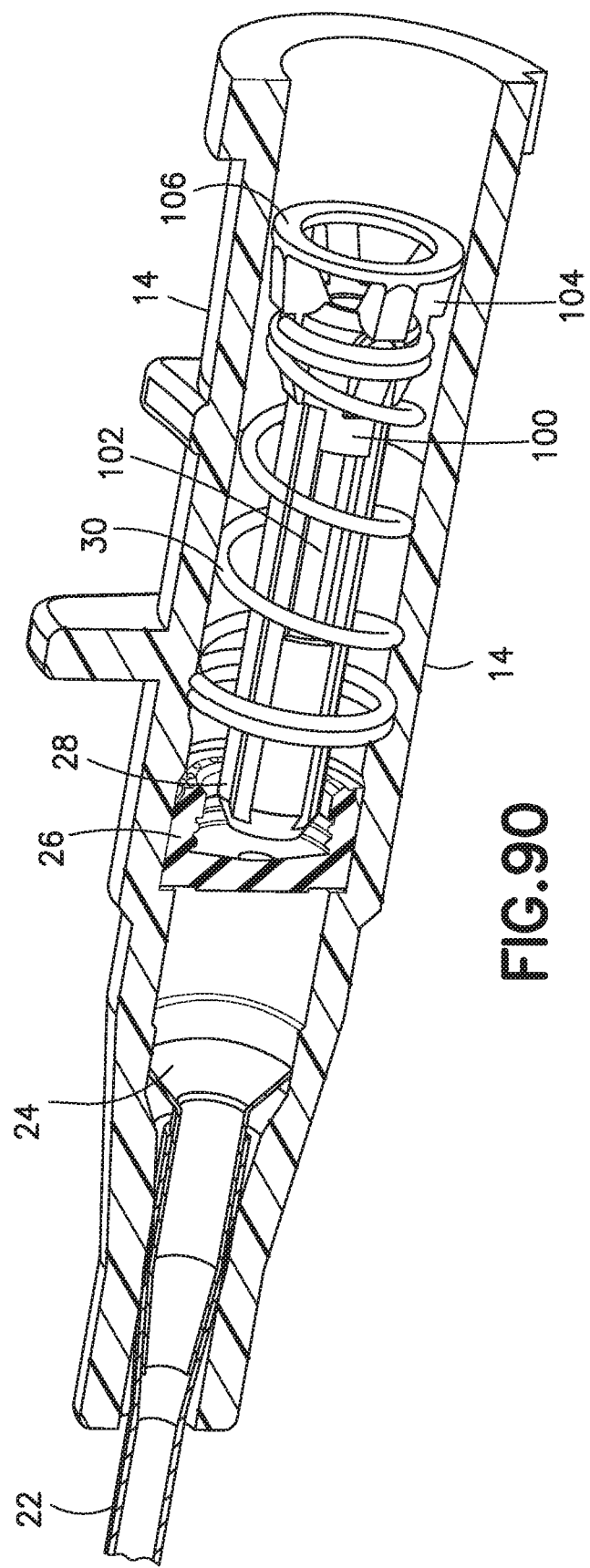
FIG. 90 illustrates the operation of the catheter hub valve actuator in a free state.
Figure 91:
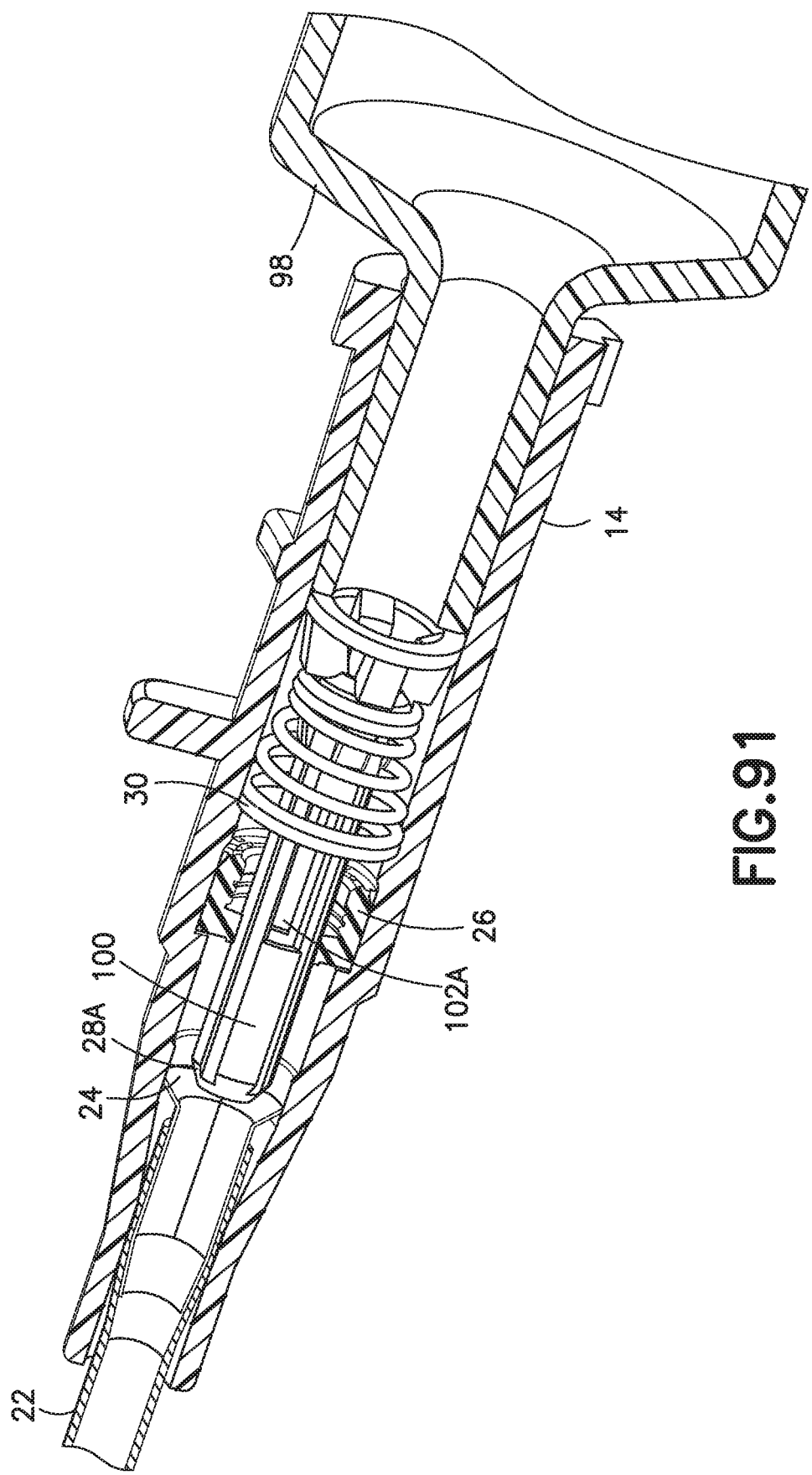
FIG. 91 illustrates the operation of the catheter hub valve actuator in a compressed state.

FIGS. 90 and 91 depict the use of the catheter valve actuator 28. The introducer needle 12 initially extends through the actuator 28, the septum 26, the wedge 24, and the catheter tube 22. After the introducer needle 12 and the catheter tube 22 are inserted into a patient, the needle 12 is withdrawn, closing the septum 26. As a male Luer connector 98 is inserted into the catheter hub 14, the Luer connector 98 abuts and moves the actuator 28 in the distal direction, compressing the biasing member 30. Further insertion of the Luer connector 98 moves the actuator 28 through the septum 26, opening the slits and allowing fluid to flow through the catheter hub 14.

When the Luer connector 98 is removed, the biasing member 30 moves the actuator 28 in the opposite direction, removing it from the septum 26, closing the slits, and preventing fluid from flowing therethrough. This allows the catheter to be reused while in the patient's vein, as opposed to a single-use catheter where the actuator would remain in the septum after a Luer connector 98 is removed. However, a single-use catheter can also be used with the needle shield 20 described herein.

The actuator 28 has an actuator barrel 100 surrounding an internal passage. The actuator barrel 100 is a substantially tubular member and the internal passage is substantially cylindrical. A first end of the actuator barrel 100 has a nose with a chamfered outer surface to engage the septum 26. The tubular member has one or more openings 102 to permit fluid flow through and around the actuator barrel 100. The actuator 28 includes a rear portion for engaging a male Luer connector.

In a first exemplary embodiment shown in FIG. 90, the actuator 28 includes first and second sets of openings 102 in the barrel with the first set of openings near the nose. Openings are also illustrated in the actuator 28 of FIGS. 79-80. The rear portion of the actuator 28 of FIG. 90 also includes a set of legs 104 extending from the barrel and connected to a ring 106. The features described in this embodiment can be used in combination with the features described throughout this application.

Figure 92:
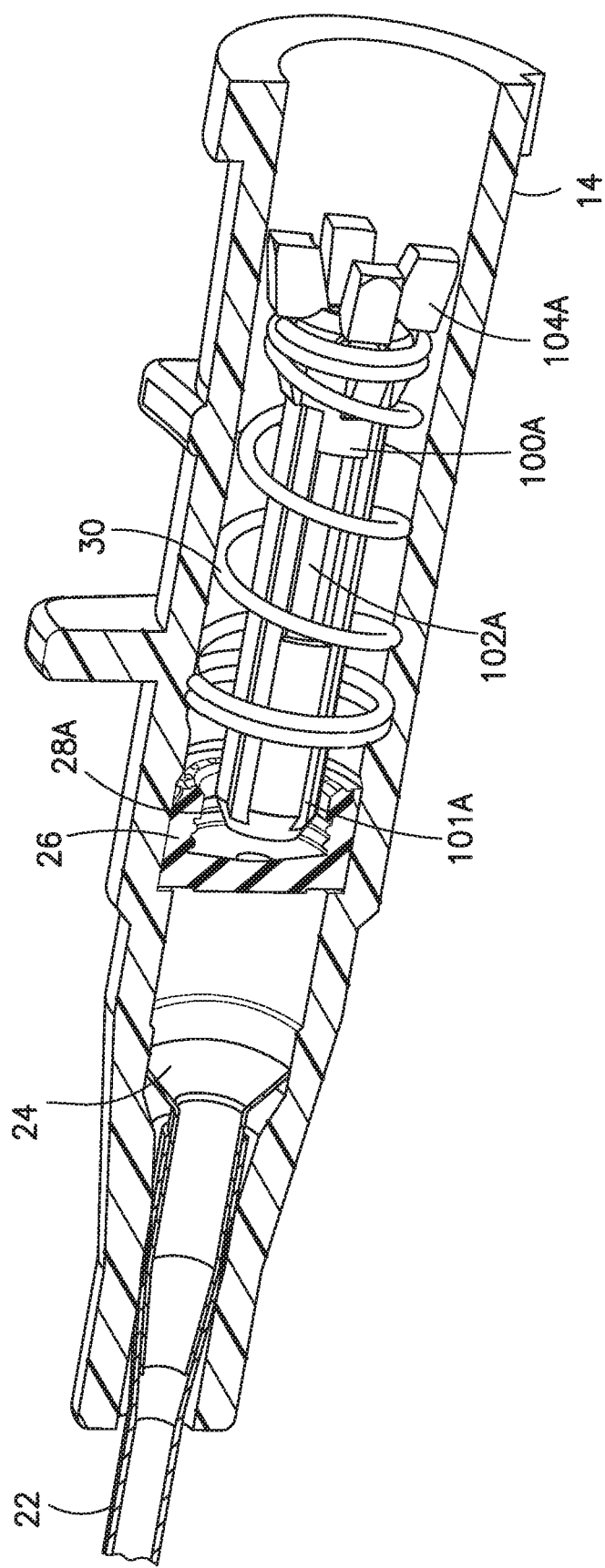
FIG. 92 illustrates the operation of a second embodiment of a catheter hub valve actuator in a free state.
Figure 93:
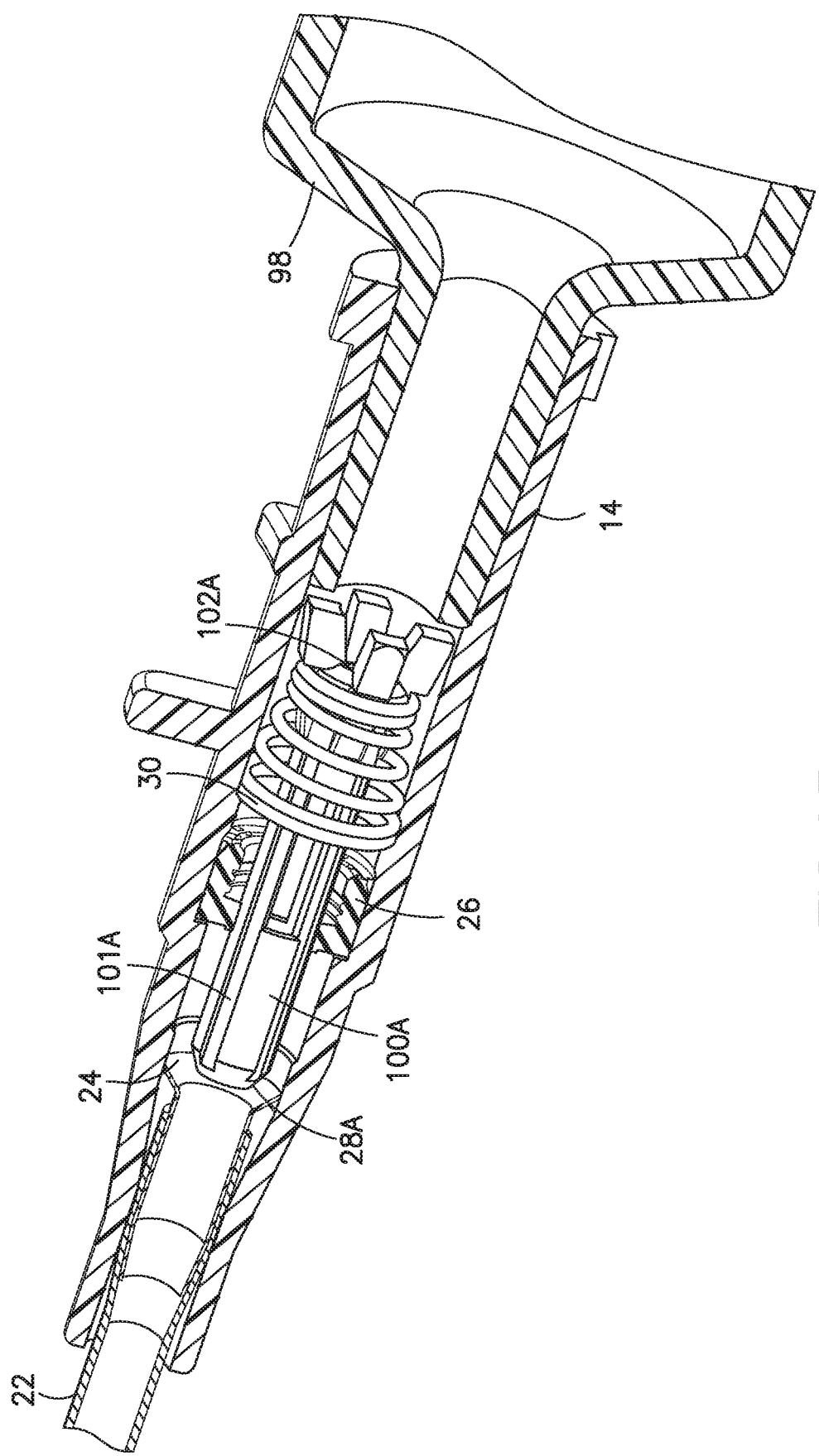
FIG. 93 illustrates the operation of the second embodiment of the catheter hub valve actuator in the compressed state.
Figure 94:
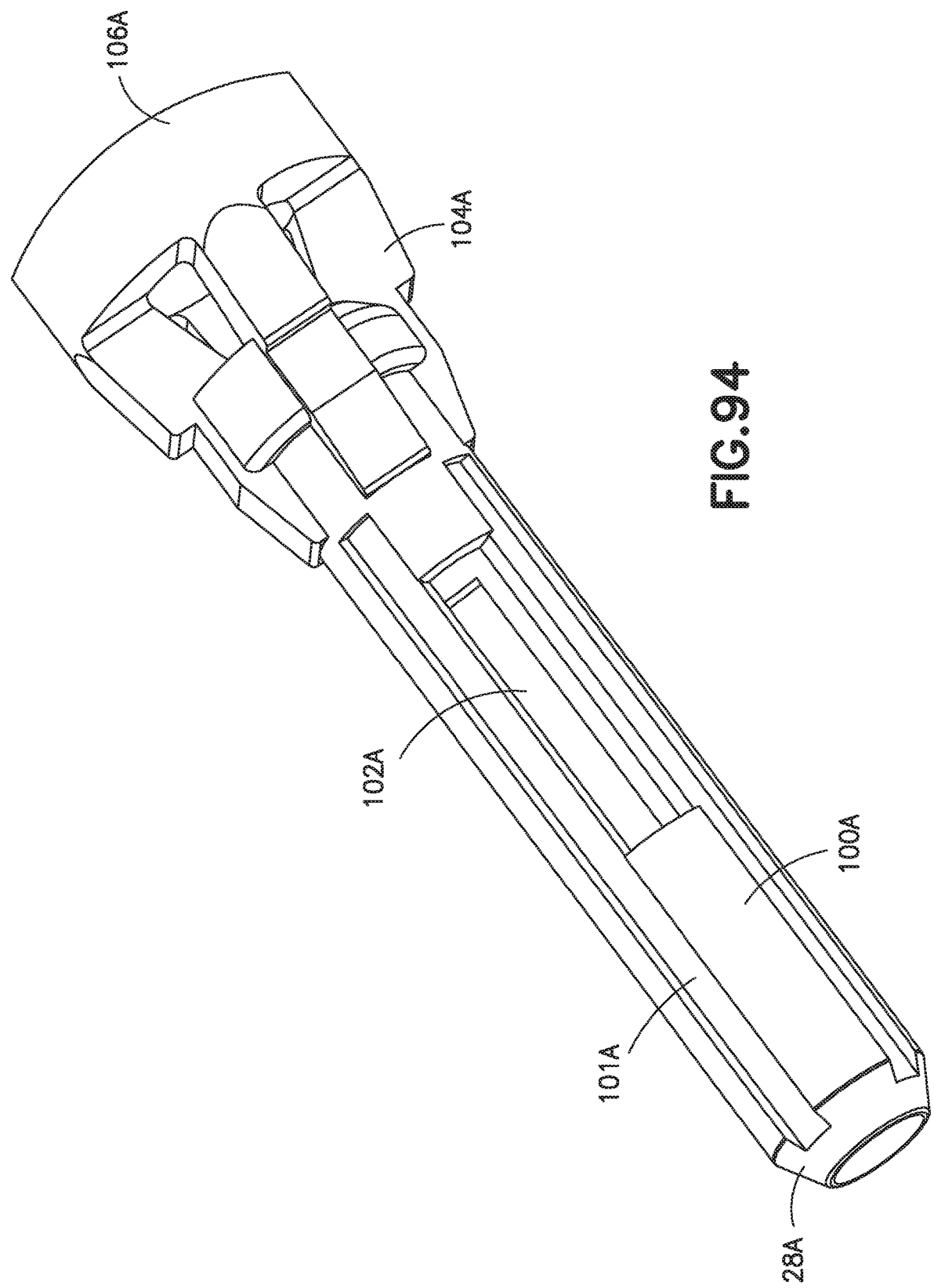
FIG. 94 illustrates another embodiment of the catheter hub valve actuator.
Figure 95:
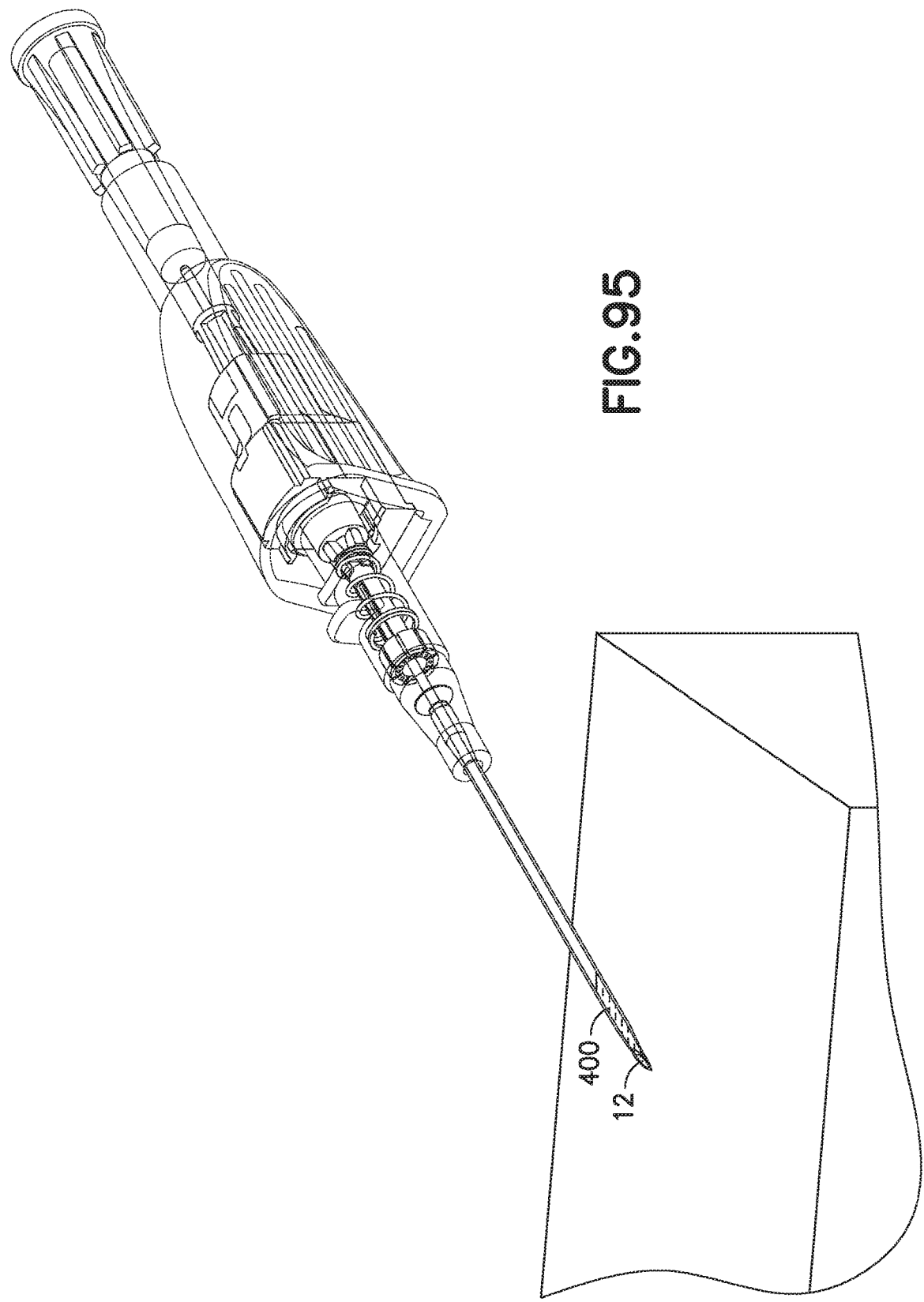
FIG. 95 illustrates an exemplary blood flashback feature of the catheter assembly.
Figure 96:
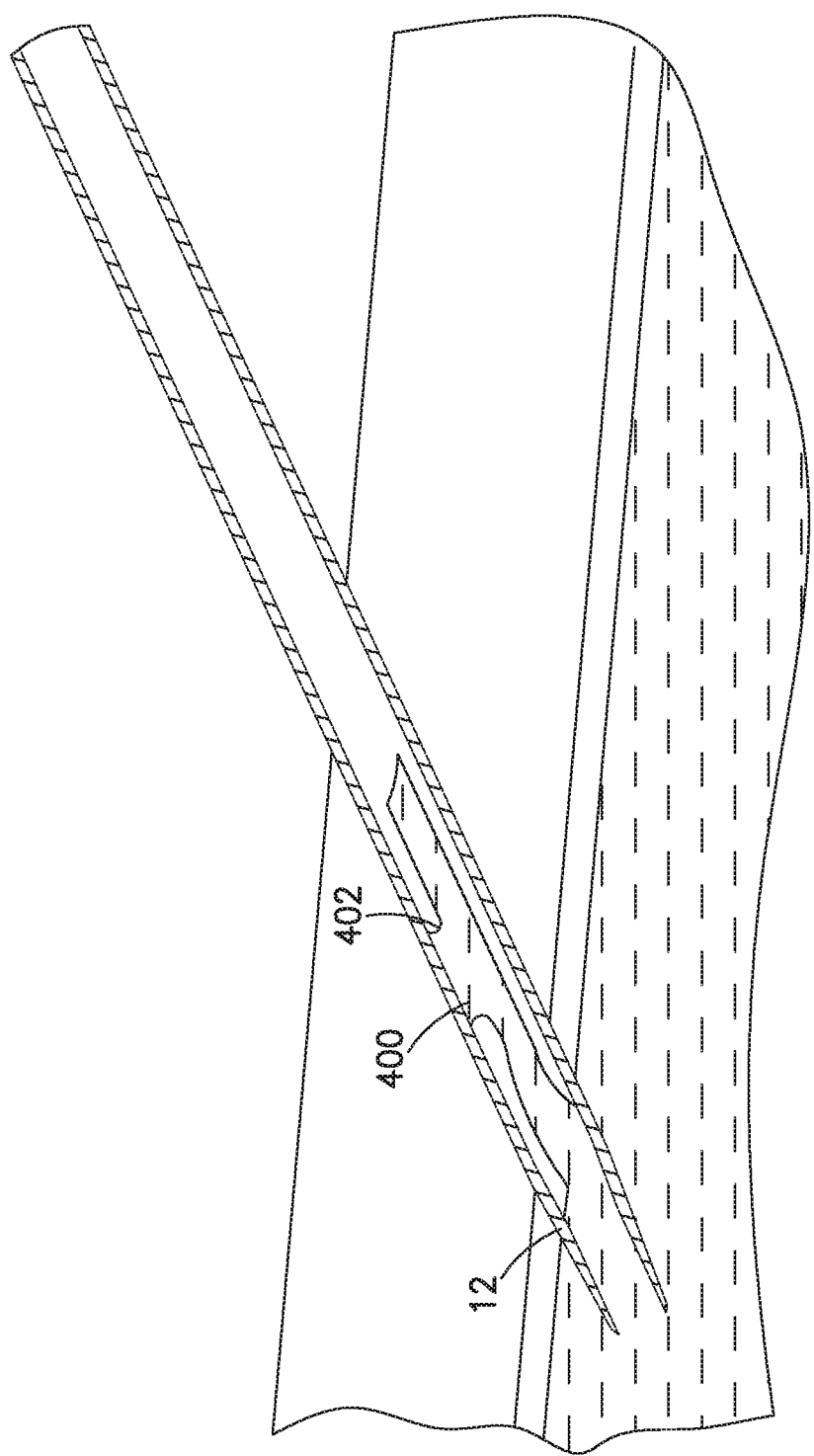
FIG. 96 illustrates the needle of the blood flashback feature of the catheter assembly of FIG. 95.
Figure 97:
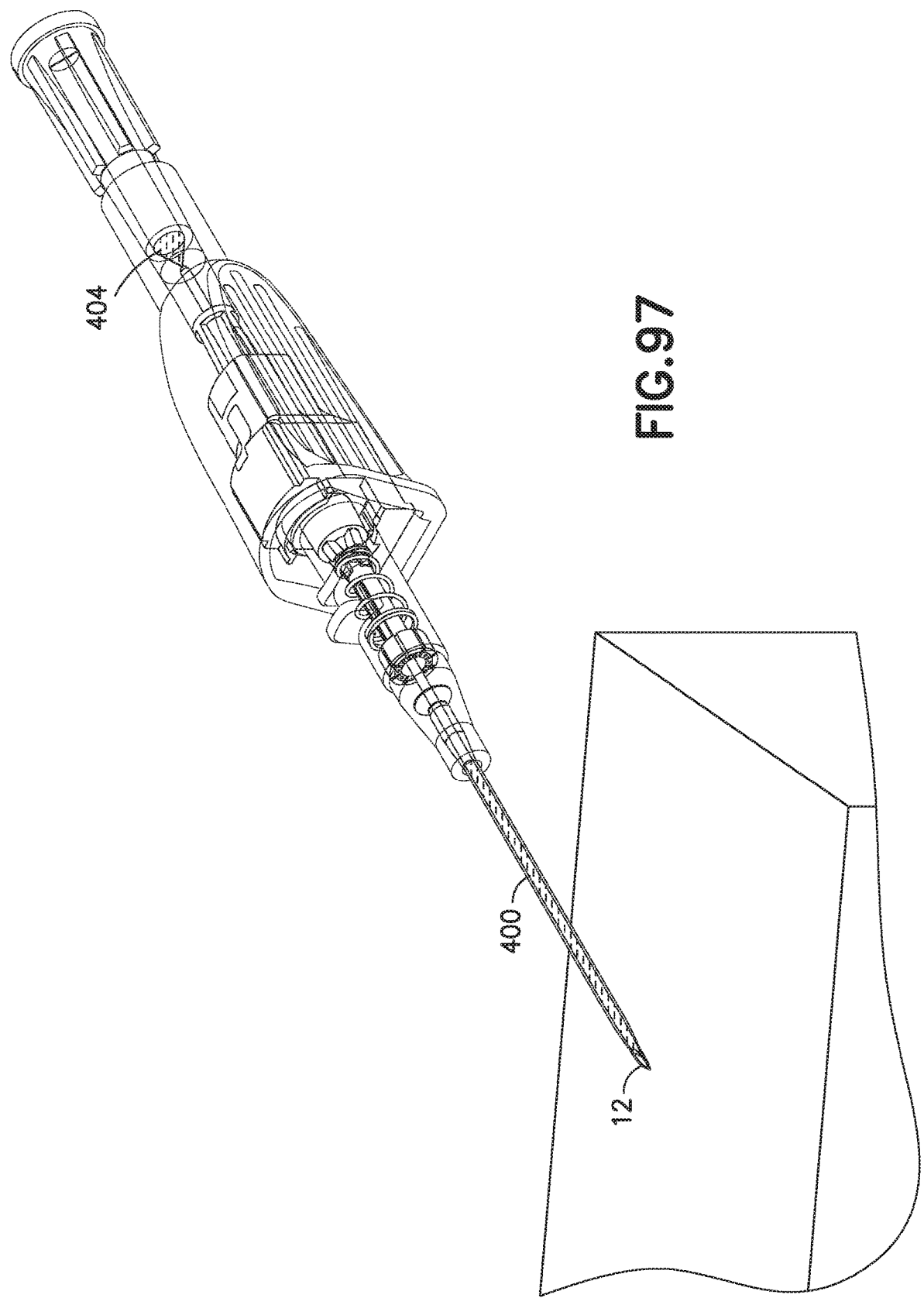
FIG. 97 illustrates a second exemplary blood flashback feature of the catheter assembly.
Figure 98:
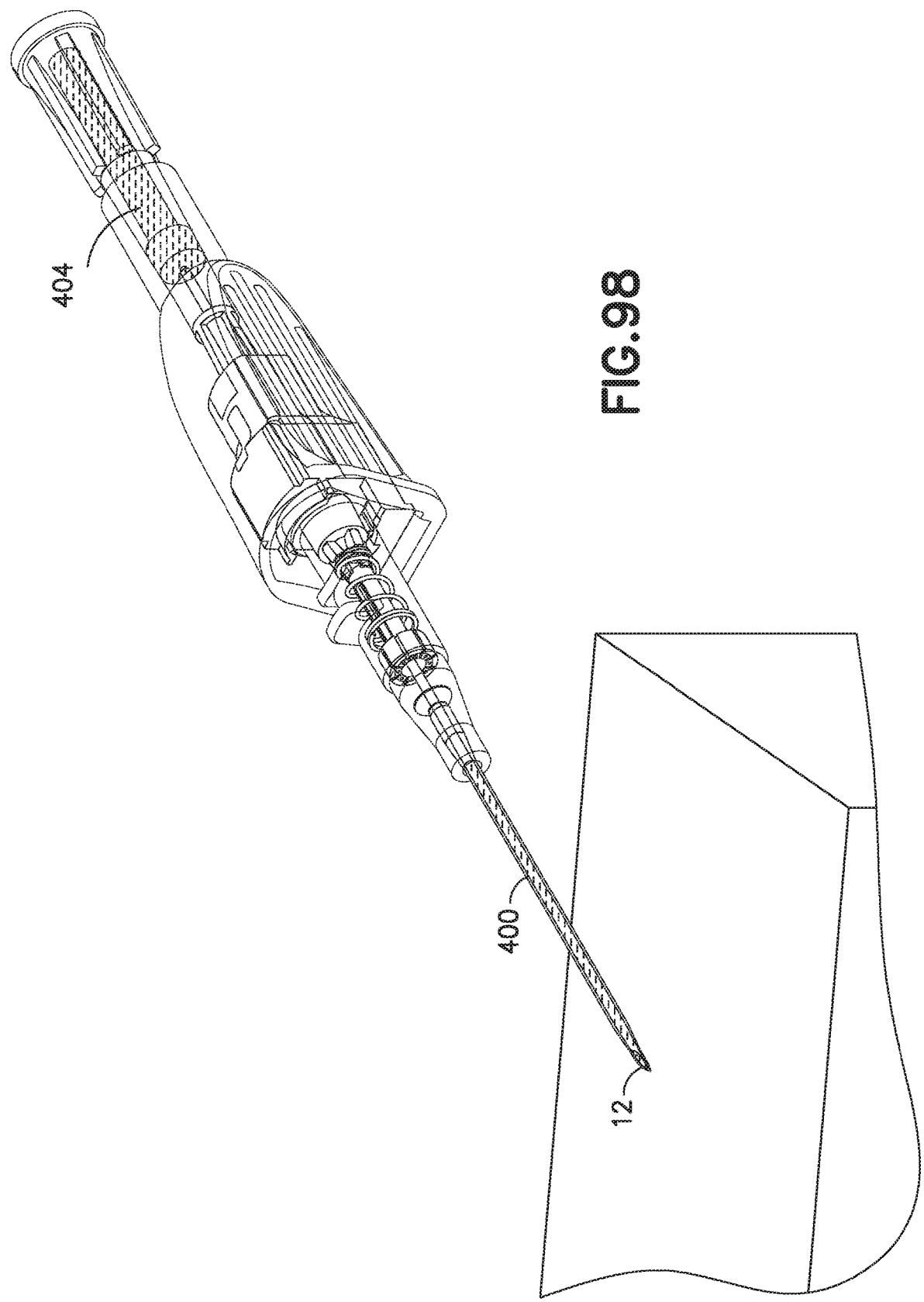
FIG. 98 illustrates the second exemplary blood flashback feature of the catheter assembly of FIG. 97 with blood flashback in two places.
Figure 99:
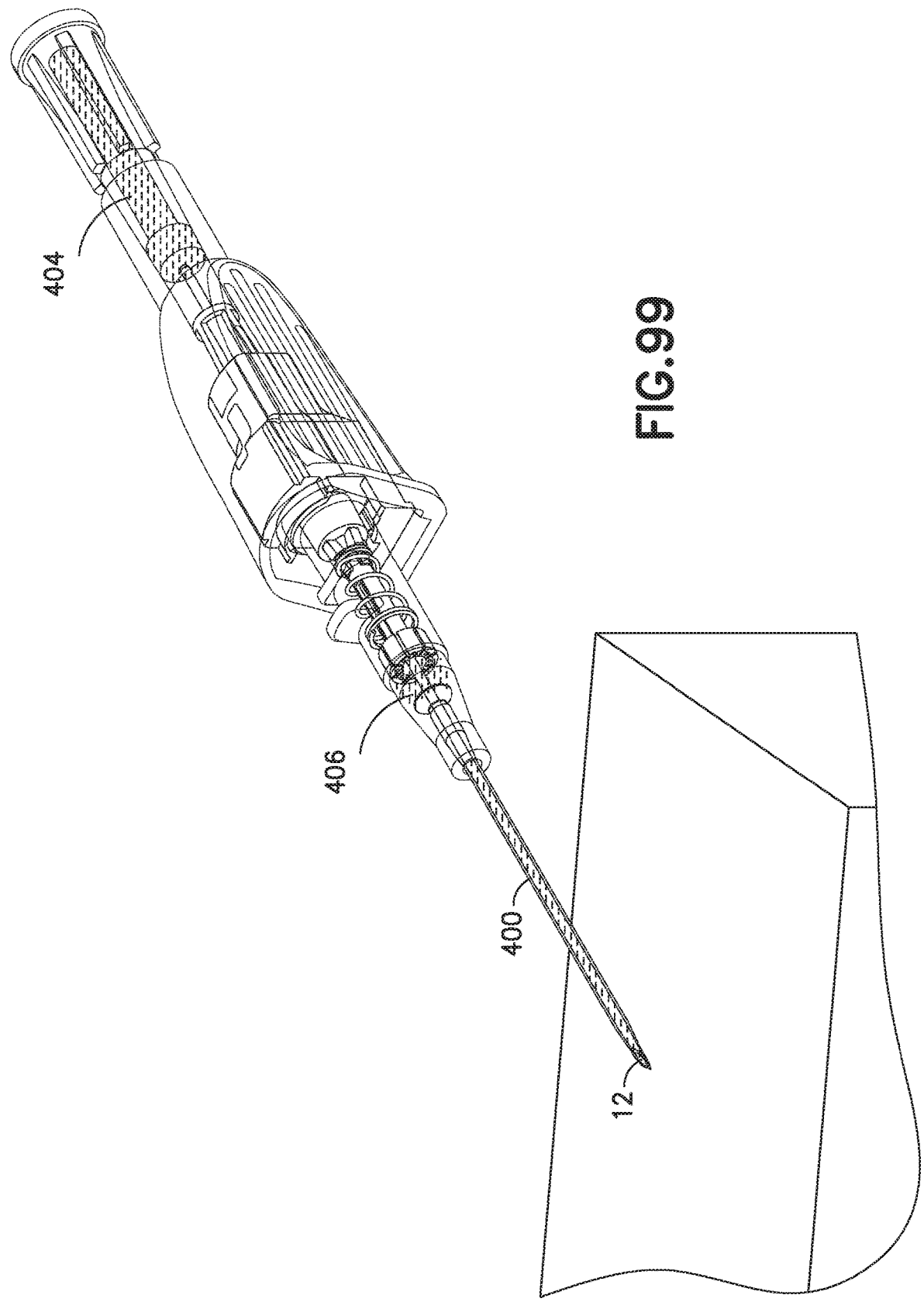
FIG. 99 illustrates a third exemplary blood flashback features of the catheter assembly with blood flashback in three places.

In a second exemplary embodiment shown in FIGS. 92-94, the actuator 28A includes a set of grooves 101A and a set of openings 102A. The grooves 101A extend from the nose toward the back of the actuator barrel 100A. The openings 102A are positioned towards the rear of the barrel 101A. When the actuator 28A extends through the septum 26, the grooves 101A channel fluid to the openings 102A which remain on the proximal side of the septum 26. The grooves 101A may be positioned on the side of the openings 102A or directly in line with the openings 102A. The rear portion of the actuator includes a set of legs 104A extending from the barrel. As illustrated in FIG. 94, a ring 106A may be connected to the legs 104A to engage a Luer connector 98 or the Luer connector 98 may directly engage the legs 104A as illustrated in FIGS. 92 and 93. The features described in this embodiment can be used in combination with the features described throughout this application.

In an exemplary embodiment, the biasing member 30 is a spring, for example a helical compression spring with a distal end and a proximal end. The spring may be made from metal, plastic, an elastomer, or another suitable resilient material. The distal end of the spring forms an interference fit with the inner surface of the catheter hub 14. The interference fit may be sufficient to retain the spring, even during loading. The proximal end of the spring connects to the actuator 28. The features described in this embodiment can be used in combination with the features described throughout this application.

FIGS. 95-99 depict various exemplary blood flashback features of the catheter assembly. Flashback is the visibility of blood that confirms the entry of the needle tip into the vein. Primary flashback 400 is seen through the catheter tubing as blood travels into the open distal end of the hollow needle 12, out a notch or opening 402 (also visible in FIG. 13) in the needle 12 near the needle tip, and up through the internal annular space between the needle 12 and the inside of the catheter tubing 22. The secondary flashback 404 is seen in the needle hub/grip 16 when it comes out of the back of the needle 12 and enters a flash chamber in the needle hub/grip. Air is vented by the plug in the back of the needle hub/grip 16 by a porous membrane or micro grooves. Tertiary flashback 406 is in the catheter hub 14 when the blood from the primary flashback 400 flows into it and stops at the blood control septum 26. Air is vented by micro grooves in the periphery of the blood control septum 26. The features described in this embodiment can be used in combination with the features described throughout this application.

Figure 100:
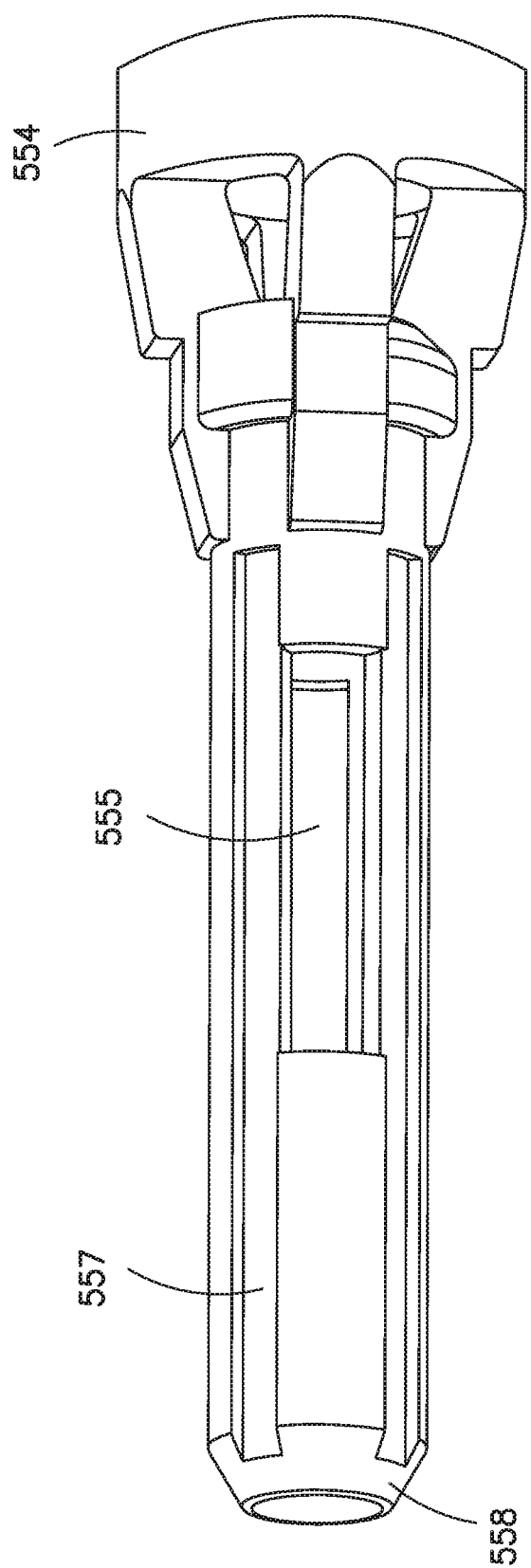
FIG. 100 illustrates a right side view of the exemplary embodiment of the actuator of FIG. 94.

FIG. 100 illustrates the actuator of FIG. 94 in further detail. The actuator 554 can be used in the catheter assemblies illustrated in FIG. 90-93. The actuator 554 includes a nose 558 that reduces friction when the actuator 554 penetrates into a septum 538 of a catheter hub assembly. The actuator 554 further includes openings 555 that extend through the actuator 554 in a direction perpendicular to a centerline of the actuator 554. For example, the actuator 554 can include two rectangular shaped openings 555, although more or less are contemplated.

The actuator 554 also includes a plurality of grooves 557 that extend axially along the distal portion of an outer surface of the actuator 554 in a plane parallel to the centerline of the actuator 554. For example, four grooves 557, substantially radially equidistant from each other, can be present along an external surface of the distal portion of the actuator 554, although more or less grooves 557 are contemplated. The grooves 557 can be of varying depths into the actuator 554. The grooves 557 are different from the openings 555 because the grooves 557 do not extend through the actuator 554.

The openings 555 and the grooves 557 advantageously provide increased area for the fluid to move inside the catheter hub assembly. The increased area advantageously allows for fluid flushing and to prevent coagulation of fluid in the proximal and distal ends of the septum. Additionally, the openings 555 and the plurality of grooves 557 advantageously minimize the stagnation of fluid and allow for greater mixing. The grooves 57 further prevent the septum from sealing on an outside surface of the actuator during operation. By not forming a sealing interface, the fluid is permitted to leak through the septum via the grooves 57 and provide additional flushing.

Figure 101A:
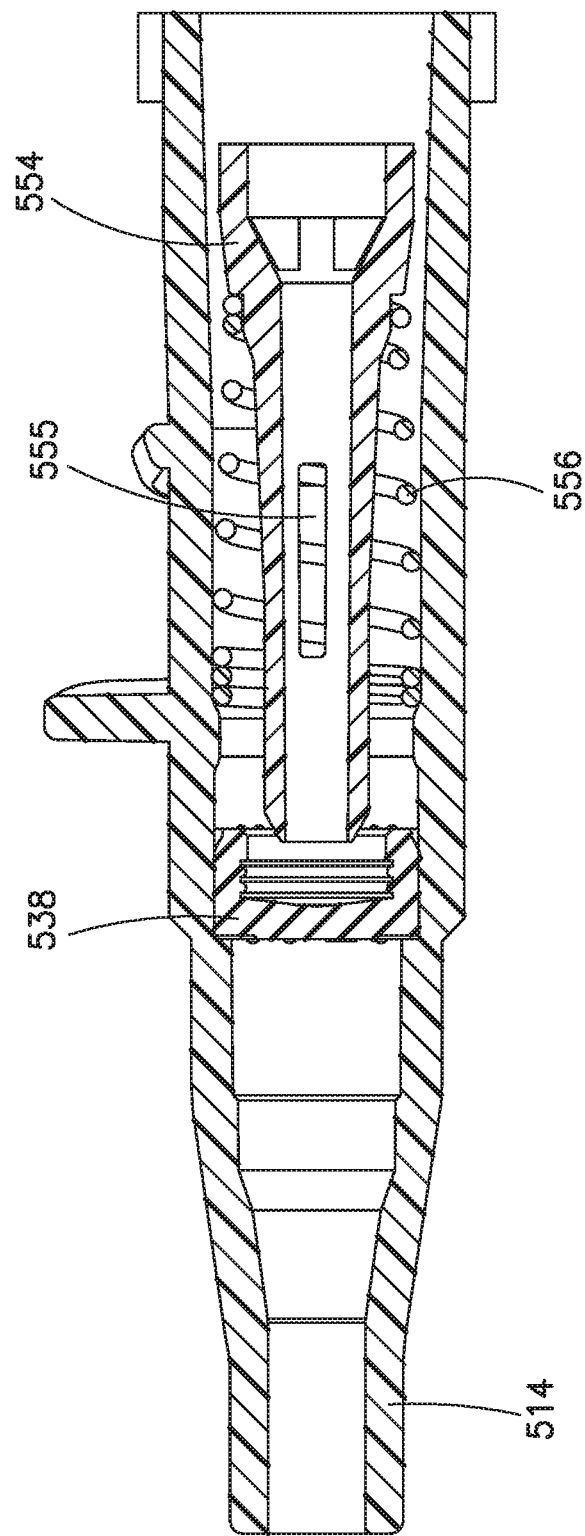
FIG. 101A illustrates a cross sectional view of the actuator of FIG. 100 in a catheter hub assembly.

FIG. 101A illustrates the actuator 554 of FIG. 100 in the catheter hub assembly. Similar to the embodiments described above, the catheter hub assembly further includes a catheter hub 514, a septum 538 and a biasing member 556. As illustrated, the openings 555 and the grooves 557 of the actuator 554 provide more area for fluid flow inside the catheter hub 514, thus achieving the advantages described above.

Figure 101B:
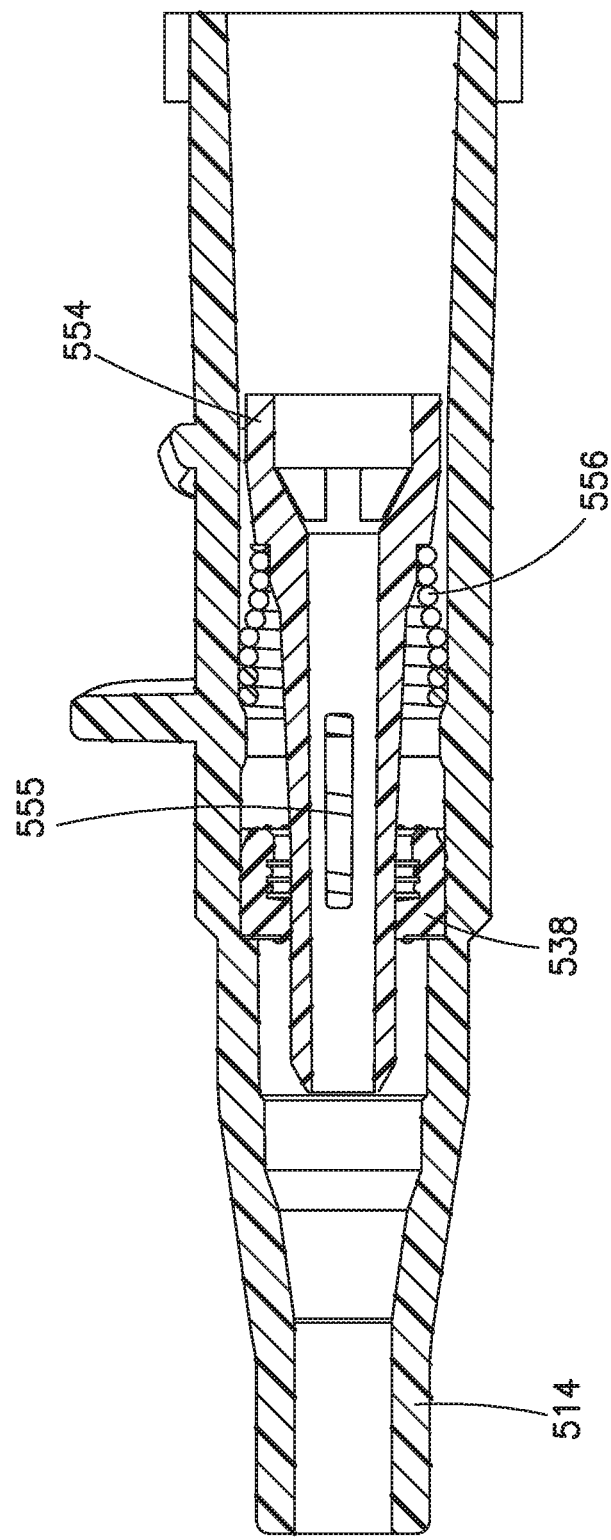
FIG. 101B illustrates the cross sectional view of the catheter hub assembly of FIG. 101A when penetrating a septum.
Figure 101C:
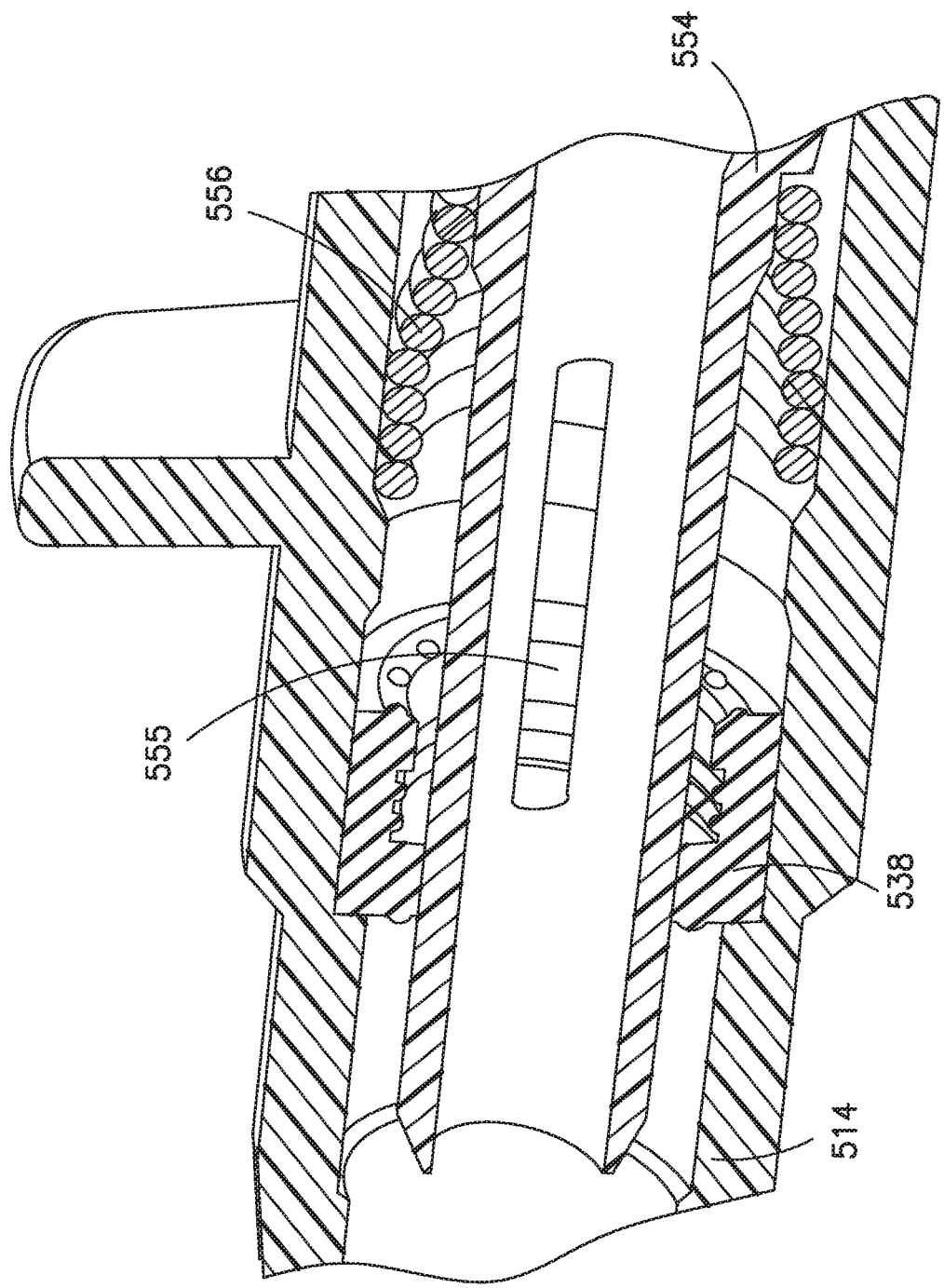
FIG. 101C illustrates a left perspective cross sectional view of the catheter hub assembly of FIG. 101A when penetrating a septum.

FIGS. 101B and 101C illustrate the catheter hub assembly when the biasing member 556 is compressed and the actuator 554 penetrates the septum 538. The catheter hub assembly may be configured such that the openings 555 and/or the grooves 557 of the actuator 554 optionally penetrates the septum 538. In this embodiment, the openings 555 in the actuator 554 do not penetrate the septum 538. However, the grooves 557 in the actuator 554 penetrate the septum 538. This configuration allows for increased fluid flow from the proximal end to the distal end of the septum 38 through the grooves 557, in addition to the advantages described above. After operation of the catheter assembly is complete, the actuator 554 is retracted from the septum 538 via the force exerted by the biasing member 556. The catheter assembly is configured for multiple uses upon depression of the actuator 554. The features described in this embodiment, including the actuator, can be used in combination with the features described throughout this application.

Figure 102A:
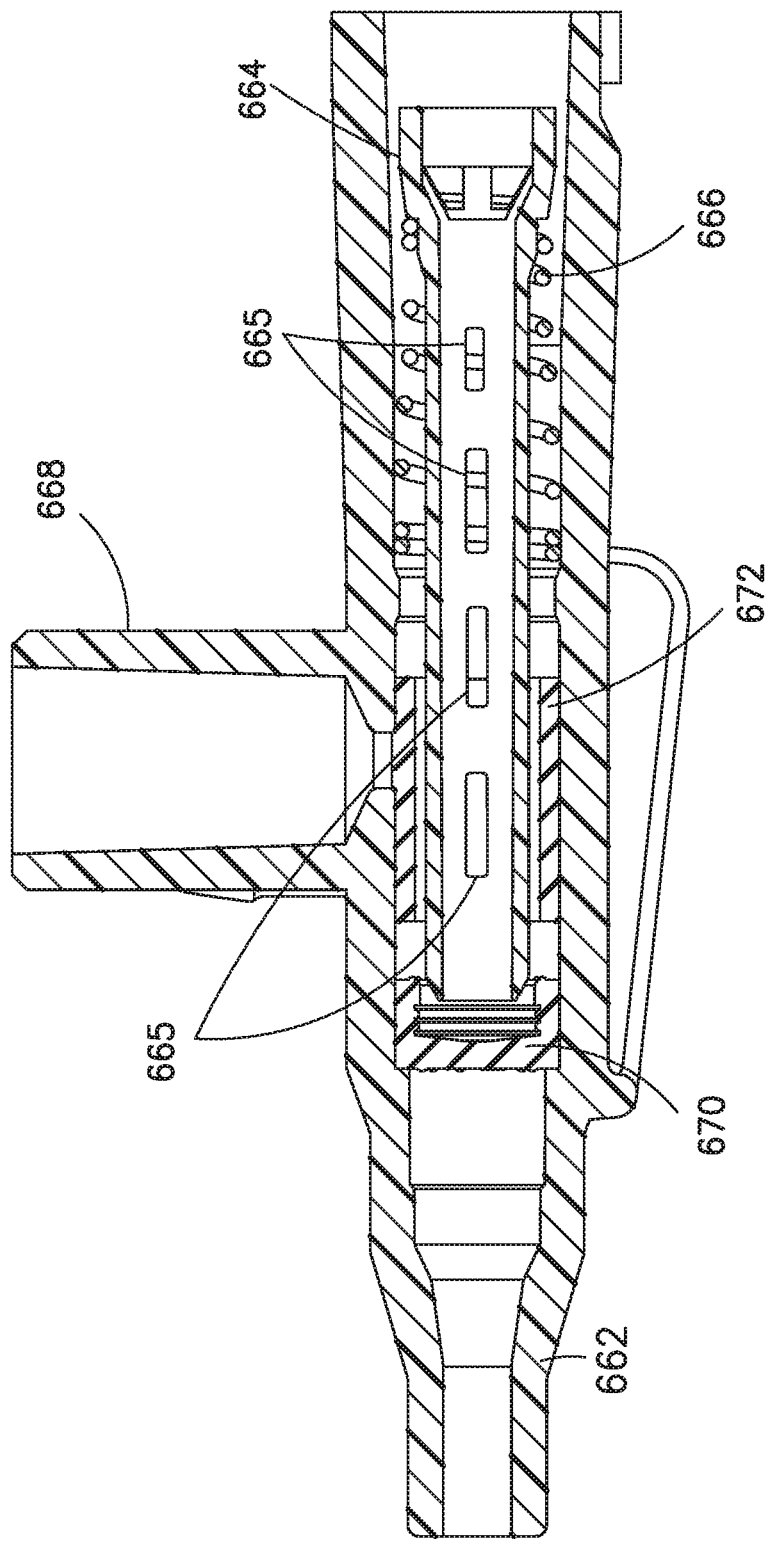
FIG. 102A illustrates a cross sectional view of another exemplary embodiment of a catheter hub assembly.

FIG. 102A illustrates another embodiment of an actuator 664 in a catheter hub assembly. The catheter hub assembly includes a catheter hub 662 having a side port 668. The side port 668 provides secondary access to the fluid flow in the catheter hub 662. The intersection of the main bore of the catheter hub 662 and the side port 668 includes a sleeve 672. The sleeve 672 provides selective fluid communication between the side port 668 and the catheter hub 662. Specifically, when sufficient fluid pressure is applied through the side port 168, the sleeve 672 compresses. The compression of the sleeve 672 allows for fluid to enter the catheter hub 662. The catheter hub assembly further includes a septum 670 and a biasing member 666 that provides tension to the actuator 664.

The actuator 664 includes a plurality of openings 665 that extend through the actuator 664 in a similar manner as described above. The actuator 664 includes two rows of four openings 665 having different sizes and similar spacing, although various quantities, sizes and spacing of the openings 665 are contemplated. As illustrated, the openings 665 provide more area for fluid flow inside the catheter hub 662, thus achieving similar advantages described above with respect to FIGS. 101-101C.

Figure 102B:
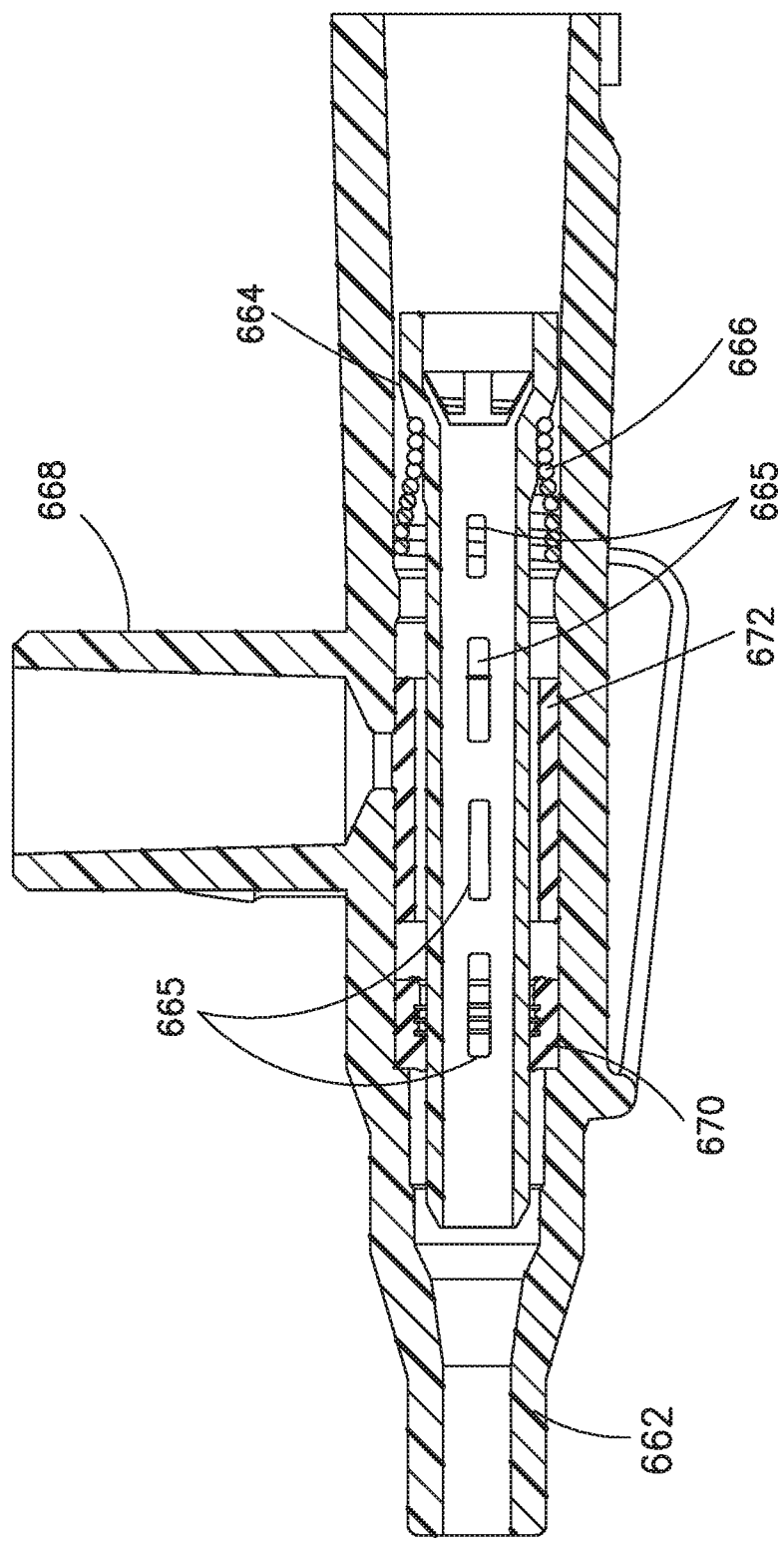
FIG. 102B illustrates the cross sectional view of the catheter hub assembly of FIG. 102A when penetrating a septum.
Figure 102C:
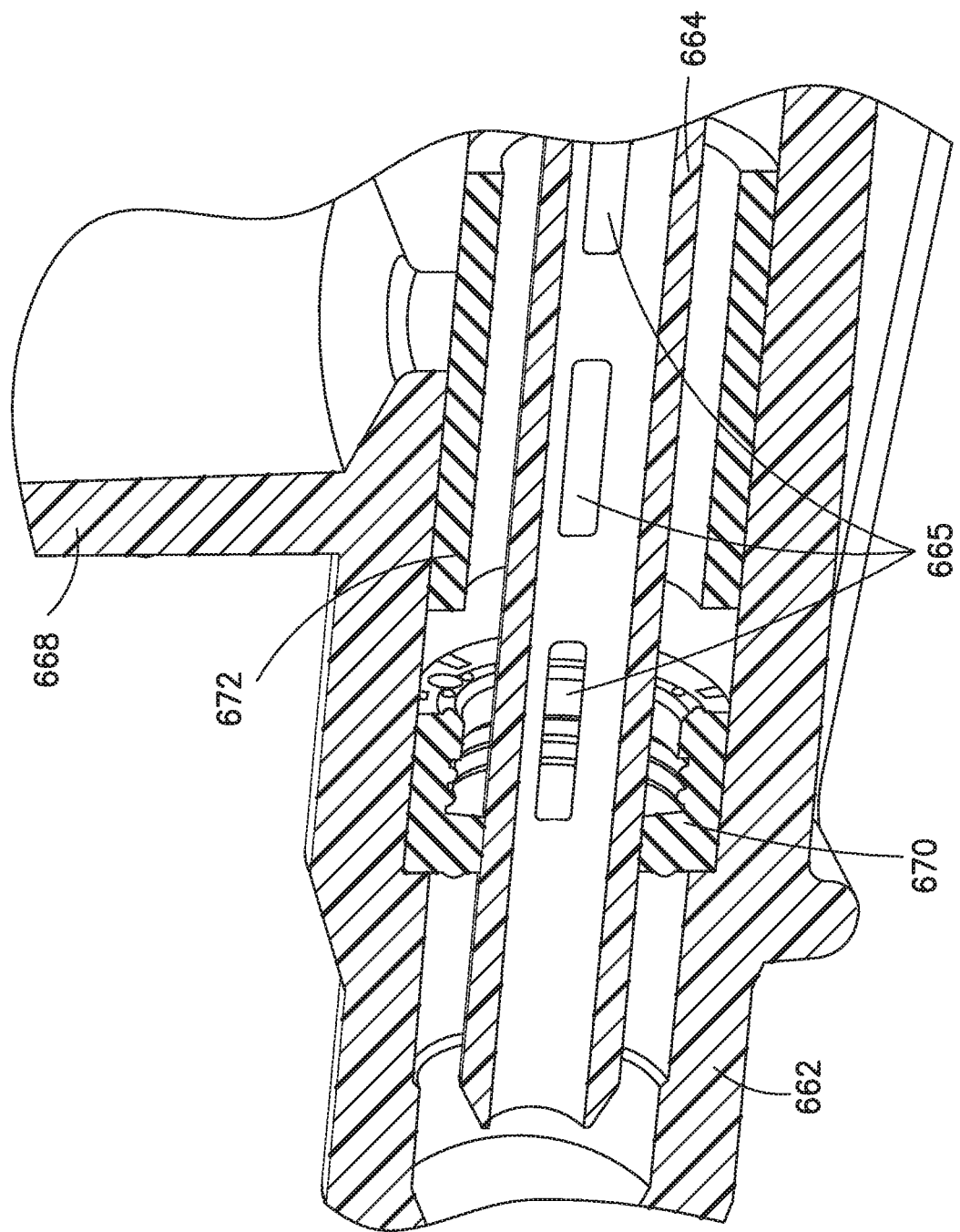
FIG. 102C illustrates a left perspective cross sectional view of the catheter hub assembly of FIG. 102A when penetrating a septum.

FIGS. 102B and 102C illustrate the catheter hub assembly when the actuator 664 penetrates the septum 670 and compresses the biasing member 666. The catheter hub assembly is configured such that the openings 665 of the actuator 664 optionally penetrate the septum 670. In this embodiment, the openings 665 in the actuator 664 do not penetrate the septum 670. This configuration allows for increased fluid flow between the side port 668 and the catheter hub 662 at the proximal end of the septum 670, in addition to the advantages described above. If the openings 665 in the actuator 664 penetrate the septum 670, increased mixing of fluid would also take place at a distal end of the septum 670.

When operation of the catheter assembly is complete, the actuator 664 is retracted from the septum 670 via the force exerted by the biasing member 666. The catheter assembly is configured for multiple uses upon depression of the actuator 664. The features described in this embodiment, such as the actuator, can be used in combination with the features described throughout this application.

In another exemplary embodiment, the collar of the catheter hub as described above can be replaced by any other structure that defines a notch. For example, the collar may be a groove or a recess in the catheter hub. Accordingly, the groove in the catheter hub can be used to engage and disengage a clip in a similar manner as described above. The features described in this embodiment can be used in combination with the features described throughout this application.

The foregoing detailed description of the certain exemplary embodiments has been provided for the purpose of explaining the principles of the invention and its practical application, thereby enabling others skilled in the art to understand the invention for various embodiments and with various modifications as are suited to the particular use contemplated. This description is not necessarily intended to be exhaustive or to limit the invention to the exemplary embodiments disclosed. Any of the embodiments and/or elements disclosed herein may be combined with one another to form various additional embodiments not specifically disclosed. Accordingly, additional embodiments are possible and are intended to be encompassed within this specification and the scope of the appended claims. The specification describes specific examples to accomplish a more general goal that may be accomplished in another way.

As used in this application, the terms "front," "rear," "upper," "lower," "upwardly," "downwardly," and other orientational descriptors are intended to facilitate the description of the exemplary embodiments of the present invention, and are not intended to limit the structure of the exemplary embodiments of the present invention to any particular position or orientation. Terms of degree, such as "substantially" or "approximately" are understood by those of ordinary skill to refer to reasonable ranges outside of the given value, for example, general tolerances associated with manufacturing, assembly, and use of the described embodiments.

The invention claimed is:
1. A catheter assembly comprising:
   a catheter extending in an axial direction;
   a catheter hub attached to the catheter, the catheter hub having a collar, the collar including a notch that extends in said axial direction;

a needle having a sharp distal tip and disposed in the catheter;

a needle shield connected to the catheter hub when the needle is in a first position; and a clip disposed in the needle shield that cooperates with the needle, wherein the clip engages the collar of the catheter hub in the first position of the needle, the clip disengages the collar of the catheter hub through the notch when the needle is retracted to a second position to enclose at least a portion of the needle; and a centerline of the notch is parallel to a centerline of the catheter hub.

2. The catheter assembly of claim 1, wherein a portion of the collar has an outer diameter greater than an outer diameter of a portion of the catheter hub adjacent to the collar.

3. The catheter assembly of claim 1, wherein the notch of the collar has an outer diameter substantially equal to or greater than an outer diameter of a portion of the catheter hub adjacent to the collar.

4. The catheter assembly of claim 1, wherein the collar includes external Luer threads.

5. The catheter assembly of claim 1, wherein the first position of the needle biases the clip into an open position during needle use.

6. The catheter assembly of claim 1, wherein the second position of the needle allows the clip to move to a closed position to block the distal tip of the needle when the needle is retracted after needle use.

7. The catheter assembly of claim 6, wherein the clip includes one or more flags that block the distal tip of the needle in the second position.

8. The catheter assembly of claim 1, further comprising a washer disposed in the needle shield that cooperates with the needle, wherein the needle further includes a deformation; and the washer prevents the distal tip of the needle and the deformation from exiting the needle shield when the needle is in the second position.

9. The catheter assembly of claim 8, wherein the clip and the washer enclose the distal tip of the needle when the needle is in the second position.

10. The catheter assembly of claim 1, wherein the clip includes a spade that attaches the clip to the needle shield, and an outer surface of the spade is exposed to an outside of the catheter assembly.

11. The catheter assembly of claim 10, wherein the spade includes one or more barbs, and the one or more barbs engage an inner surface of the needle shield.

12. The catheter assembly of claim 1, wherein the collar is disposed on a proximal end of the catheter hub, and the clip includes a latch that is configured to engage and disengage the collar and the needle shield.

13. The catheter assembly of claim 12, wherein the clip includes two legs, and the latch is disposed between the two legs.

14. The catheter assembly of claim 12, wherein the latch is aligned with the notch to disengage the collar when the needle is in the second position.

15. The catheter assembly of claim 12, wherein the latch moves laterally to disengage the collar.

16. The catheter assembly of claim 12, wherein the latch is off-center with respect to the needle at each of the engaged and disengaged position.

17. A catheter assembly comprising:

a catheter extending in an axial direction;

a catheter hub attached to the catheter, the catheter hub having a collar disposed on a proximal end of the catheter hub, the collar including a notch that extends in said axial direction;

a needle having a sharp distal tip and disposed in the catheter;

a needle shield connected to the catheter hub when the needle is in a first position; and a clip disposed in the needle shield that cooperates with the needle, wherein the clip includes a latch that is configured to engage and disengage the collar and the needle shield;

the clip engages the collar of the catheter hub in the first position of the needle, and the latch is offset from the notch to engage the collar in said first position; and the clip disengages the collar of the catheter hub through the notch when the needle is retracted to a second position to enclose at least a portion of the needle.

18. A catheter assembly comprising:

a catheter;

a needle having a sharp distal tip and disposed in the catheter, the sharp distal tip extending through the catheter in a first needle position;

a catheter hub attached to the catheter;

a needle shield configured to be connected to the catheter hub; and a clip disposed in the needle shield that cooperates with the needle, the sharp distal tip being enclosed by the clip in the needle shield in a second needle position, the clip including a spade that connects the clip to the needle shield in the first position and in the second position, wherein an outer surface of the spade is exposed to an outside of the catheter assembly.

19. The catheter assembly of claim 18, wherein the spade includes one or more barbs, and the one or more barbs engage an inner surface of the needle shield.

20. A method of operating a catheter assembly comprising:

disposing a needle having a sharp distal tip in a catheter;

biasing a clip when the needle is in use in a first position;

removing the needle from a catheter hub having a notch;

releasing the clip when the needle is in a second position to enclose at least a portion of the needle; and disengaging the clip from the catheter hub by moving a portion of the clip axially through the notch; wherein a centerline of the notch is parallel to a centerline of the catheter hub.

21. The method of claim 20, further comprising engaging the clip and the catheter hub when the needle is in the first position.

22. The method of claim 20, further comprising connecting the catheter hub and a needle shield when the clip engages the catheter hub; and disconnecting the catheter hub and the needle shield when the clip disengages the catheter hub, wherein the clip is disposed in the needle shield.

23. The method of claim 20, wherein the catheter hub includes a collar, the collar including the notch.

* * * * *